(12) United States Patent
Boger

(10) Patent No.: US 6,262,271 B1
(45) Date of Patent: Jul. 17, 2001

(54) ISO-CBI AND ISO-CI ANALOGS OF CC-1065 AND THE DUOCARMYCINS

(75) Inventor: Dale L. Boger, La Jolla, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 09/529,345

(22) PCT Filed: Oct. 14, 1998

(86) PCT No.: PCT/US98/21749

§ 371 Date: Apr. 12, 2000

§ 102(e) Date: Apr. 12, 2000

(87) PCT Pub. No.: WO99/19298

PCT Pub. Date: May 22, 1999

Related U.S. Application Data

(60) Provisional application No. 60/061,892, filed on Oct. 14, 1997.

(51) Int. Cl.[7] ............... C07D 209/04; C07D 209/56; C07D 401/14; C07D 403/06; C07D 403/14

(52) U.S. Cl. ............... 546/201; 548/217; 548/305.1; 548/306.1; 548/420; 548/427; 548/449; 548/491; 549/458

(58) Field of Search .................. 548/420, 427, 548/449, 491; 546/201

(56) References Cited

U.S. PATENT DOCUMENTS 5,475,092 * 12/1995 Chari et al. .................. 530/391.7

OTHER PUBLICATIONS

Sundberg, et al., "Synthesis and Intramolecular Photoaddition of an Indole Quinonediazide", *Tetrahedron Lett.* 24: 4773–4776 (1983).

Boger, et al., "Total Synthesis and Evaluation of (±)-N-(tert-Butyloxycarbonyl)-CBI, (±)-CBI-CDPI$_1$, and (±)-CBI-CDPI$_2$: CC-1065 Functional Agents Incorporating the Equivalent 1,2,9,9a-Tetrahydrocycloprop[1,2-c]benz[1,2-e]indol-4-one (CBI) Left-Hand Subunit", *J. Am. Chem. Soc.* 111: 6461–6463 (1989).

Boger, et al., "Synthesis and Evaluation of Aborted and Extended CC-1065 Functional Analogues: (+)- and (−)-CPI-PDE-I$_1$, (+)- and (−)-CPI-CDPI$_1$, and (±)-, (+)-, and (−)-CPI-CDPI$_3$. Preparation of Key Partial Structures and Definition of an Additional Functional Role of the CC-1065 Central and Right-Hand Subunits", *J. Am. Chem. Soc.* 112: 4623–4632 (1990).

Boger, et al., "Synthesis of N-(Phenylsulfonyl)-CI, N-(tert-Butyloxy)carbonyl)-CI, CI-CDPI$_1$, and CI-CDPI$_2$: CC-1065 Functional Analogues Incorporating the Parent 1,2,7,7a-Tetrahydrocycloprop[1,2-c]indol-4-one (CI) Left-Hand Subunit", *J. Am. Chem. Soc.* 112: 5230–5240 (1990).

Boger, et al., "Synthesis of N-(tert-Butyloxycarbonyl)-CBI, CBI, CBI-CDPI$_1$, and CBI-CDPI$_2$: Enhanced Functional Analogues of CC-1065 Incorporating the 1,2,9,9a-Tetrahydrocylcopropa[c]benz[e]indol-4-one (CBI) Left-Hand Subunit", *J. Org. Chem.* 55: 5823–5832 (1990).

(List continued on next page.)

*Primary Examiner*—Jane C. Oswecki
(74) *Attorney, Agent, or Firm*—Donald G. Lewis

(57) ABSTRACT

A series of bioactive analogs of (+)-CC-1065 (1) and the duocarmycins 2 and 3 are synthesized. The bioactive analogs include either iso-CI or iso-CBI (6 and 7) as a DNA alkylation subunit. Conjugated to the DNA alkylating subunits are a variety of DNA binding subunits. The bioactive analogs maintain their DNA selectivity and display enhanced reactivity.

22 Claims, 14 Drawing Sheets

(+)-CC-1065
1

(+)-Duocarmycin A
2

(+)-Duocarmycin SA
3

OTHER PUBLICATIONS

Boger, et al., "A Demonstration of the Intrinsic Importance of Stabilizing Hydrophobic Binding and Non–Covalent Van der Waals Contacts Dominant in the Non–Covalent CC–1065/B–DNA Binding", Chem.–Biol. Interactions 73: 29–52 (1990).

Boger, et al., "Demonstration of a pronounced effect of noncovalent binding selectivity on the (+)–CC–1065 DNA alkylation and identification of the pharmacophore of the alkylation subunit", Proc. Natl. Acad. Sci. USA 88: 1431–1435 (1991).

Boger, et al., "Synthesis and Preliminary Evaluation of (+)–CBI–Indole$_2$: An Enhanced Functional Analog of (+)–CC–1065", Bioorg. Med. Chem. Lett. 1: 115–120 (1991).

Boger, et al., "(+)–CC–1065 DNA Alkylation: Key Studies Demonstrating a Noncovalent Binding Selectivity Contribution to the Alkylation Selectivity", J. Am. Chem. Soc. 113: 3980–3983 (1991).

Sundberg, et al., "Synthesis of Cycloprop[c]indol–5–ones from 4–Diazo–3–[N–(2–propenyl)amido] cyclohexadien–1–ones. Exploration of Copper(I) and Copper(II) Complexes as Catalysts", J. Org. Chem. 56: 3048–3054 (1991).

Boger, et al., "CC–1065 Partial Structures: Enhancement of Noncovalent Affinity for DNA Minor Groove Binding through Introduction of Stabilizing Electrostatic Interactions", J. Org. Chem. 57: 1277–1284 (1992).

Boger, et al., "An Improved Synthesis of 1,2,9,9a–Tetrahydrocyclopropa[c]benz[e]indol–4–one (CBI): A Simplified Analogue of the CC–1065 Alkylation Subunit", J. Org. Chem. 57: 2873–2876 (1992).

Boger, et al., "DNA Alkylation Properties of Enhanced Functional Analogs of CC–1065 Incorporating the 1,2,9, 9a–Tetrahydrocyclopropa[1,2–c]–benz[1,2–e]indol–4–one (CBI) Alkylation Subunit", J. Am. Chem. Soc. 114: 5487–5496 (1992).

Yamamoto, et al., "Concerted DNA Recognition and Novel Site–Specific Alkylation by Duocarmycin A with Distamycin A", Biochem. 32: 1059–1066 (1993).

Sugiyama, et al., "A Novel Guanine N3 Alkylation by Antitumor Antibiotic Duocarmycin A", Tetrahedron Lett. 34: 2179–2182 (1993).

Boger, et al., "Reversibility of the Duocarmycin A and SA DNA Alkylation Reaction", J. Am. Chem. Soc. 115: 9872–9873 (1993).

Boger, et al., "Molecular Basis for Sequence Selective DNA Alkylation by (+)– and ent–(–)–CC–1065 and Related Agents: Alkylation Site Models that Accomodate the Offset AT–rich Adenine N3 Alkylation Selectivity", Bioorg. Med. Chem. 2: 115–135 (1994).

Boger, et al., "(+)– and ent–(–)–Duocarmycin SA and (+)– and ent–(–)–N–BOC–DSA DNA Alkylation Properties. Alkylation Site Models That Accomodate the Offset AT–Rich Adenine N3 Alkylation Selectivity of the Enantiomeric Agents", J. Am. Chem. Soc. 116: 1635–1656 (1994).

Asai, et al., "A Novel Property of Duocarmycin and Its Analogues for Covalent Reaction with DNA", J. Am. Chem. Soc. 116: 4171–4177 (1994).

Warpehoski, et al., "Acid–Dependent Electrophilicity of Cyclopropylpyrroloindoles. Nature's Masking Strategy for a Potent DNA Alkylator", J. Am. Chem. Soc. 116: 7573–7580 (1994).

Boger, et al., "CBI–TMI: Synthesis and Evaluation of a Key Analog of the Duocarmycins. Validation of a Direct Relationship between Chemical Solvolytic Stability and Cytotoxic Potency and Confirmation of the Structural Features Responsible for the Distinguishing Behavior of Enantiomeric Pairs of Agents", J. Am. Chem. Soc. 116: 7996–8006 (1994).

Boger, et al., "Design, Synthesis, and Evaluation of CC–1065 and Duocarmycin Analogs Incorporating the 2,3, 10,10a–Tetrahydro–1H–cyclopropa–[d]benzo[f] quinol–5–one (CBQ) Alkylation Subunit: Identification and Structural Origin of Subtle Stereolectronic Features That Govern Reactivity and Regioselectivity", J. Am. Chem. Soc. 116: 11335–11348 (1994).

Boger, et al., "1,2,9,9a–Tetrahydrocyclopropa[c]benz[e] indol–4–one (CBI): An Enhanced and Simplified Analog of the CC–1065 and Duocarmycin Alkylation Subunits", J. Org. Chem. 60: 1271–1275 (1995).

Boger, et al., "Second Definitive Test of Proposed Models for the Origin of the CC–1065 and Duocarmycin DNA Alkylation Selectivity", J. Am. Chem. Soc. 117: 1443–1444 (1995).

Thompson, et al., "Monoalkylation and Cross–Linking of DNA by Cyclopropapyrroloindoles Entraps Bent and Straight Forms of A–Tracts", J. Am. Chem. Soc. 117: 2371–2372 (1995).

Warpehoski, et al., "Enzyme–like Rate Acceleration in the DNA Minor Groove. Cyclopropylpyrroloindoles as Mechanism–Based Inactivators of DNA", J. Am. Chem. Soc. 117: 2951–2952 (1995).

Boger, et al., "DNA Alkylation Properties of CC–1065 and Duocarmycin Analogs Incorporating the 2,3,10,10a–Tetrahydrocyclopropa[d]benzo[f]–quinol–5–one Alkylation Subunit: Identification of Subtle Structural Features That Contribute to the Regioselectivity of the Adenine N3 Alkylation Reaction", J. Am. Chem. Soc. 117: 11647–11655 (1995).

Lin, et al., "Solution Structure of the Covalent Duocarmycin A–DNA Duplex Complex", J. Mol. Biol. 248: 162–179 (1995).

Boger, et al., "CC–1065 CBI Analogs: an Example of Enhancement of DNA Alkylation Efficiency Through Introduction of Stabilizing Electrostatic Interactions", Bioorg. Med. Chem. 3: 611–621 (1995).

Boger, et al., "CC–1065 and the Duocarmycins: Understanding their Biological Function through Mechanistic Studies", Angew. Chem. Int. Ed. Engl. 35: 1439–1474 (1996).

Boger, et al., "Demonstration and Definition of the Noncovalent Binding Selectivity of Agents Related to CC–1065 by an Affinity Cleavage Agent Noncovalent Binding Coincidental with Alkylation", Bioorg. Med. Chem. 4: 859–867 (1996).

Boger, et al., "A Comparative Study of the Solvolysis Reactivity, Regioselectivity, and Stereochemistry of the Duocarmycin A and SA Alkylation Subunits", Bioorg. Med. Chem. Lett. 6: 1955–1960 (1996).

Boger, et al., "Total Synthesis of (+)–Duocarmycin A, epi–(+)–Duocarmycin A and Their Unnatural Enantiomers: Assessment of Chemical and Biological Properties", J. Am. Chem. Soc. 119: 311–325 (1997).

Park, et al., "Covalent Modification of N3 of Guanine by (+)–CC–1065 Results in Protonation of the Cross–Strand Cytosine", J. Am. Chem. Soc. 119: 629–630 (1997).

Boger, et al., "Duocarmycin SA Shortened, Simplified, and Extended Agents: A Systematic Examination of the Role of the DNA Binding Subunit", *J. Am. Chem. Soc. 119*: 4977–4986 (1997).

Boger, et al., "Reversed and Sandwiched Analogs of Duocarmycin SA: Establishment of the Origin of the Sequence-Selective Alkylation of DNA and New Insights into the Source of Catalysis", *J. Am. Chem. Soc. 119*: 4987–4998 (1997).

Boger, et al., "CC–1065 and the Duocarmycins: Synthetic Studies", *Chem. Rev. 97*: 787–828 (1997).

Boger, et al., "Synthesis and Evaluation of CC–1065 and Duocarmycin Analogs Incorporating the 1,2,3,4,11,11a–Hexahydrocyclopropa[c]naphtho–[2,1–b] azepin–6–one (CNA) Alkylation Subunit: Structural Features that Govern Reactivity and Reaction Regioselectivity", *J. Org. Chem. 62*: 5849–5863 (1997).

Boger, et al., "Synthesis and Evaluation of CC–1065 and Duocarmycin Analogues Incorporating the Iso–CI and Iso–CBI Alkylation Subunits: Impact of Relocation of the C–4 Carbonyl", *J. Org. Chem. 62*: 8875–8891 (1997).

Boger, et al., "Catalysis of the CC–1065 and Duocarmycin DNA Alkylation Reaction: DNA Binding Induced Conformational Change in the Agent Results in Activation", *Bioorg. Med. Chem. 5*: 263–276 (1997).

Eis, et al., "High Resolution Solution Structure of a DNA Duplex Alkylated by the Antitumor Agent Duocarmycin SA", *J. Mol. Biol. 272*: 237–252 (1997).

* cited by examiner

ISO-CBI AND ISO-CI ANALOGS OF CC-1065 AND THE DUOCARMYCINS

This application claims benefit of provisional application No. 60/061,892 filed Oct. 14, 1997 which is a 371 of of PCT/US98/21749 filed Oct. 14, 1998.

This invention was made with government support under Contract No. CA55276 by the National Institutes of Health. The government has certain rights in the invention.

FIELD OF INVENTION

The invention relates to antitumor antibiotics. More particularly, the invention relates to analogs of CC-1065 and the duocarmycins having DNA alkylation and antitumor antibiotic activities.

BACKGROUND (+)-CC-1065 (1) and the duocarmycins 2 and 3, illustrated in FIG. 1, are natural products having antitumor antibiotic activity through the alkylation of DNA. (Hanka, L. J., et al. *J. Antibiot.* 1978, 31, 1211; Yasuzawa, T., et al., *Chem. Pharm. Bull.* 1995, 43, 378; and Takahashi, I., et al., *J. Antibiot.* 1991, 44, 1045.) Prior studies have shown that the natural products can withstand and may benefit from significant structural modifications to the alkylation subunit and that the resulting agents retain their ability to participate in the characteristic sequence-selective DNA alkylation reaction. (Boger, D. L., et al., *Chem. Rev.* 1997, 97, 787.) These structural modifications, and the definition of their effects have served to advance the understanding of the origin of the catalysis of the DNA alkylation reaction by 1–3. (Harper, D. E. *J. Am. Chem. Soc.* 1994, 116, 7573; and Warpehoski, M. A., et al., *J. Am. Chem. Soc.* 1995, 117, 2951.)

These structural modifications have also served to advance the understanding of the origin of the DNA sequence selectivity of 1–3. (Warpehoski, M. A. In *Advances in DNA Sequence Specific Agents;* Hurley, L. H., Ed.; JAI: Greenwich, Conn., 1992; Vol. 1, p 217; Hurley, L. H. and Draves, P. In *Molecular Aspects of Anticancer Drug-DNA Interactions;* Neidle, S. and Waring, M., Eds.; CRC: Ann Arbor, 1993; Vol. 1, p 89; and Aristoff, P. A. In *Advances in Medicinal Chemistry;* JAI: Greenwich, Conn., 1993; Vol. 2, p 67). Two models have been proposed to explain the mechanism of the DNA sequence selectivity of 1–3. One model proposed by Boger states that the DNA sequence selectivity of 1–3 is determined by the AT-rich noncovalent binding selectivity of these agents and their steric accessibility to the adenine N3 alkylation site. (Boger, D. L., et al., *Angew. Chem., Int. Ed. Engl.* 1996, 35, 1439; and Boger, D. L., et al., *Biorg. Med. Chem.* 1997, 5, 263.) This noncovalent binding model accommodates and explains the reverse and offset 5 or 3.5 base-pair AT-rich adenine N3 alkylation selectivities of the natural and unnatural enantiomers of 1 (Boger, D. L., et al., *J. Am. Chem. Soc.* 1990, 112, 4623; and Boger, D. L., et al, *Bioorg. Med. Chem.* 1994, 2, 115) and the natural and unnatural enantiomers of 2–3. (Boger, D. L., et al., *J. Am. Chem. Soc.* 1993, 115, 9872; and Boger, D. L., et al., *J. Am. Chem. Soc.* 1994, 116, 1635.) This noncovalent binding model also requires that simple derivatives of the alkylation subunits exhibit alkylation selectivities distinct from the natural products. It also offers an explanation for the identical alkylation selectivities of both enantiomers of such simple derivatives (5'-A<u>A</u>>5'-T<u>A</u>), and the more extended AT-rich selectivity of the advanced analogs of 1–3 corresponds nicely to the length of the agent and the size of the required binding region surrounding the alkylation site. This model is further supported by the demonstrated AT-rich noncovalent binding of these agents. (Boger, D. L., et al., *Chem.-Biol. Interactions* 1990, 73, 29; and Boger, D. L., et al., *J. Org. Chem.* 1992, 57, 1277.) The model is also supported by the correspondence between the observed preferential noncovalent binding and the observed DNA alkylation of these agents. (Boger, D. L, et al., *Bioorg. Med. Chem.* 1996, 4, 859.) Also the observation that the characteristic DNA alkylation selectivity of these agents does not require the presence of the C-4 carbonyl or even the activated cyclopropane provides further support for the model, (Boger, D. L.et al., *J. Am. Chem. Soc.* 1991, 113, 3980.; and Boger, D. L., et al. *Proc. Natl. Acad Sci. U.S.A.* 1991, 88, 1431.) The accuracy of this model is further demonstration of the complete switch in the inherent enantiomeric DNA alkylation selectivity that accompanied the reversal of the orientation of the DNA binding subunits with reversed versus extended analogs of the duocarmycins. (Boger, D. L., et al.,. *J. Am. Chem. Soc.* 1997, 119, 4977; Boger, D. L., et al., *J. Am. Chem. Soc.* 1997, 119, 4987; and Boger, D. L., et al., *J. Am. Chem. Soc.* 1995, 117, 1443.)

The above AT-rich noncovalent binding model contrasts with an alternative proposal in which a sequence-dependent backbone phosphate protonation of the C-4 carbonyl activates the agent for DNA alkylation and controls the sequence selectivity. (Hurley, L. H. *J. Am. Chem. Soc.* 1995, 117, 2371.)

Structural studies of DNA-agent adducts, [17-19] the C-4 carbonyl of the natural products projects out of the minor groove lying on the outer face of the complexes potentially accessible to the phosphate backbone. (Lin, C. H., et al., *J. Mol. Biol.* 1995, 248, 162.; and Smith, J. A., et al., *J. Mol. Biol.* 1997, 272, 237.) However, the relative importance of the C-4 carbonyl positioning to the properties of these agents has not been determined.

What is needed is a series of analogs of (+)-CC-1065 (1) and the duocarmycins 2 and 3 which exploit the AT-rich noncovalent binding model and which retain their DNA binding and alkylating activity and selectivity. What is needed is series of analogs of (+)-CC-1065 (1) and the duocarmycins 2 and 3 which incorporate of iso-CI and iso-CBI (6 and 7). Iso-CI and iso-CBI (6 and 7) are analogs of the CI and CBI alkylation subunits 4 and 5 wherein the key C-4 carbonyl is isomerically relocated to the C-6 or C-8 positions, now ortho to the cyclopropane, as illustrated in FIG. 2. If the AT-rich noncovalent binding model is correct, the relocated carbonyls of iso-CI and iso-CBI (6 and 7) would project into the minor groove inaccessible to the phosphate backbone if participating in an analogous adenine N3 alkylation reaction.

SUMMARY

A series of bioactive analogs of (+)-CC-1065 (1) and the duocarmycins 2 and 3 are synthesized. Each of the analogs includes iso-CI or iso-CBI (6 and 7) as a DNA alkylation subunit. The novel DNA alkylation subunits are then conjugated to known DNA binding subunits to form bioactive analogs of (+)-CC-1065 (1) and the duocannycins 2 and 3. Preferred DNA binding subunits are disclosed herein and in U.S. patent application Ser. No. 09/051,264, incorporated herein by reference.

2-(tert-Butyloxycarbonyl)-1,2,9,9a-tetrahydrocyclopropa[c]benzo[f]indol-8-one (31, N-BOC-iso-CBI) and 1-(tert-butyloxycarbonyl)-4-hydroxy-3-[[(methanesulfonyl)oxy]methyl]-2,3-dihydroindole (19, seco-N-BOC-iso-CI)

serve as preconjugate forms to the DNA alkylating subunits, i.e., iso-CI or iso-CBI (6 and 7). The approach for synthesizing compounds 31 and 19 was based on a directed ortho metallation of an appropriately functionalized benzene (13) or naphthalene (24) precursor to regiospecifically install iodine at the C-2 position. Conversion of these respective intermediates to the dihydroindole skeleton utilized an established 5-exo-trig aryl radical cyclization onto an unactivated alkene with subsequent TEMPO trap or the more recent 5-exo-trig aryl radical cyclization onto a vinyl chloride for direct synthesis of the immediate precursors. Closure of the activated cyclopropane to complete the iso-CBI nucleus was accomplished by a selective ortho spirocyclization.

Resolution and synthesis of a full set of natural product analogs and subsequent evaluation of their DNA alkylation properties revealed that the iso-CBI analogs react at comparable rates and retain the identical and characteristic sequence selectivity of CC-1065 and the duocarmycins. This observation is inconsistent with the prior art proposal that a sequence-dependent C-4 carbonyl protonation by strategically located DNA backbone phosphates controls the DNA alkylation selectivity but is consistent with the proposal that it is determined by the AT-rich noncovalent binding selectivity of the agents and the steric accessibility of the N3 alkylation site.

Solvolysis studies indicate that the iso-CBI-based agents have a stability comparable to that of CC-1065 and duocarmycin A and a greater reactivity than duocarmycin SA (6–7x). Solvolysis studies indicate also indicate that the iso-CBI-based agents are more reactive than the corresponding CBI-based agents (5x).

Confirmation that the DNA alkylation reaction is derived from adenine N3 addition to the least substituted carbon of the activated cyclopropane and its quantitation (95%) was established by isolation and characterization of the depurination adenine N3 adduct. Consistent with past studies and in spite of the deep-seated structural change in the alkylation subunit, the agents were found to exhibit potent cytotoxic activity that correlates with their inherent reactivity.

One aspect of the invention is directed to DNA alkylating compounds having a DNA alkylating subunit covalently linked to a DNA binding subunit. The DNA alkylating compound is represented by the following structure:

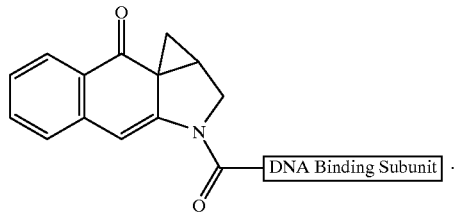

A preferred DNA binding subunit is a radical represented by the following structure:

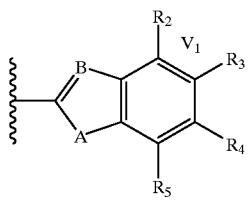

In the above structure, A is selected from the group consisting of NH and O. B is selected from the group consisting of C and N. $R_2$ is selected from the group consisting of hydrogen, hydroxyl, O-alkyl (C1–C6), N-alkyl (C1–C6)$_3$ and a first N-substituted pyrrolidine ring. $R_3$ is selected from the group consisting of hydrogen, hydroxyl, O-alkyl (C1–C6), N-alkyl (C1–C6)$_3$, the first N-substituted pyrrolidine ring. $R_4$ is selected from the group consisting of hydrogen, hydroxyl, O-alkyl (C1–C6), and N-alkyl (C1–C6)$_3$. $R_5$ is selected from the group consisting of hydrogen, hydroxyl, O-alkyl (C1–C6), and N-alkyl (C1–C6)$_3$. $V_1$ represents a first vinylene group between $R_2$ and $R_3$. However, there are various provisos. If $R_2$ participates in the first N-substituted pyrrolidine ring, then $R_3$ also particulates in the first N-substituted pyrrolidine ring. If $R_3$ participates in the first N-substituted pyrrolidine ring, then $R_2$ also particlates in the first N-substituted pyrrolidine ring. If $R_2$ and $R_3$ participate in the first N-substituted pyrrolidine ring, then $R_4$ and $R_5$ are hydrogen. If $R_2$ is hydrogen, then $R_4$ and R are hydrogen and $R_3$ is N-alkyl (C1–C6)$_3$. The first N-substituted pyrrolidine ring is fused to the first vinylene group between $R_2$ and $R_3$ and is represented by the following structure:

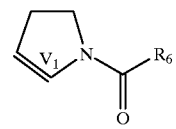

In the above structure $V_1$ represents the first vinylene group between $R_2$ and $R_3$. $R_6$ is selected from the group consisting of —$CH_2CH_3$ (alkyl), —$NHCH_3$ (—N-alkyl), —$OCH_3$ (O-alkyl), —$NH_2$, —$NHNH_2$, —$NHNHCO_2{'Bu}$, and a radical represented by the following structure:

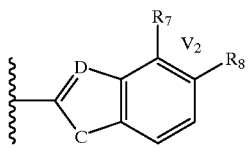

In the above structure, C is selected from the group consisting of NH and O. D is selected from the group consisting of C and N. $R_7$ is selected from the group consisting of hydrogen, hydroxyl, O-alkyl (C1–C6), N-alkyl (C1–C6)$_3$, and a second N-substituted pyrrolidine ring. $R_8$ is selected from the group consisting of hydrogen, hydroxyl, O-alkyl (C1–C6), N-alkyl (C1–C6)$_3$, the second N-substituted pyrrolidine ring. $V_2$ represents the second vinylene group between $R_7$ and $R_8$. However, the following provisos pertain. If $R_7$ participates in the N-substituted pyrrolidine ring, then $R_8$ also particlates in the N-substituted pyrrolidine ring. If $R_8$ participates in the N-substituted pyrrolidine ring only if $R_7$ also particlates in the N-substituted pyrrolidine ring. The second N-substituted pyrrolidine ring is fused to the second vinylene group between $R_7$ and $R_8$ and is represented by the following structure:

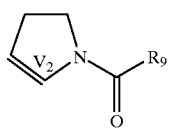

In the above sturucture, $V_2$ represents the second vinylene group between $R_7$ and $R_8$. $R_9$ is selected from the group consisting of —$CH_2CH_3$ (alkyl), —$NHCH_3$ (—N-alkyl), —$OCH_3$ (O-alkyl), —$NH_2$, —$NHNH_2$, and —$NHNHCO_2{}^tBu$.

Preferred examples include DNA alkylating compounds represented by the following structures:

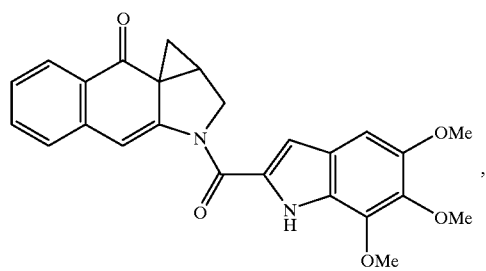

,

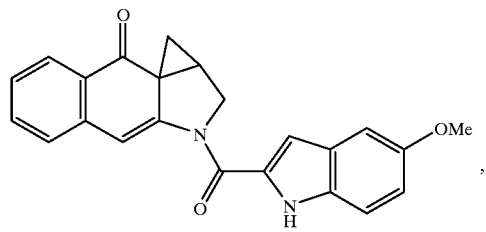

,

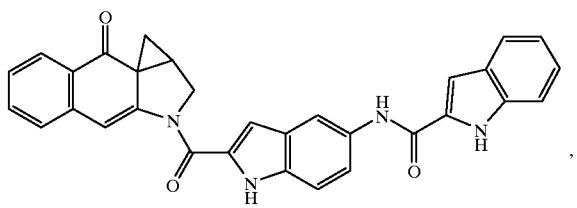

,

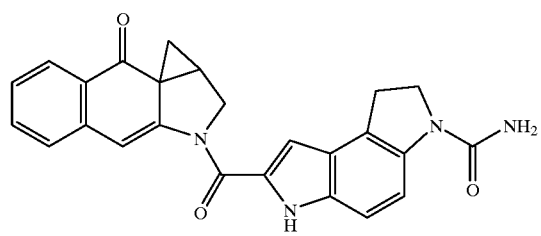

and

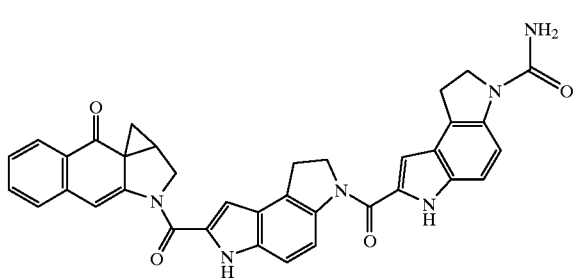

Another aspect of the invention is directed to DNA alkylating compounds represented by the following structure:

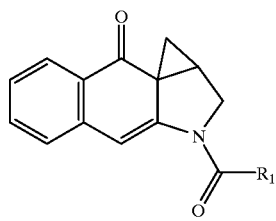

In the above structure, $R_1$ is selected from the group consisting of —C1–C6 alkyl, —$NHCH_3$ (—N-alkyl), —$OCH_3$ (O-alkyl), —$NH_2$, —$NHNH_2$, —$NHNHCO_2{}^tBu$, and a radical represented by the following structure:

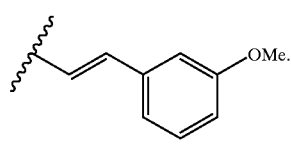

A preferred embodiment of this aspeact of the invention is represented by the following structure:

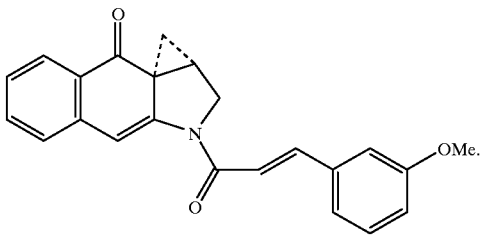

Further aspeacts of the invention are directed to chemical intermediate represented by the following structures:

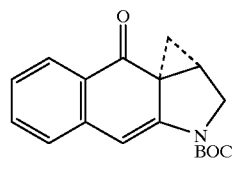

and

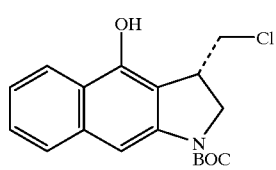

Another aspect of the invention is directed to DNA alkylating compounds having a DNA alkylating subunit covalently linked to a DNA binding subunit covalently linked said DNA alkylating subunit, wherein the DNA alkylating compound being represented by the following structure:

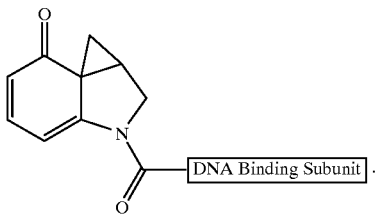

Preferred DNA binding subunit are as described above for the iso-CBI compounds. Preferred examples of this aspect of the invention include DNA alkylating compounds represented by the following structures:

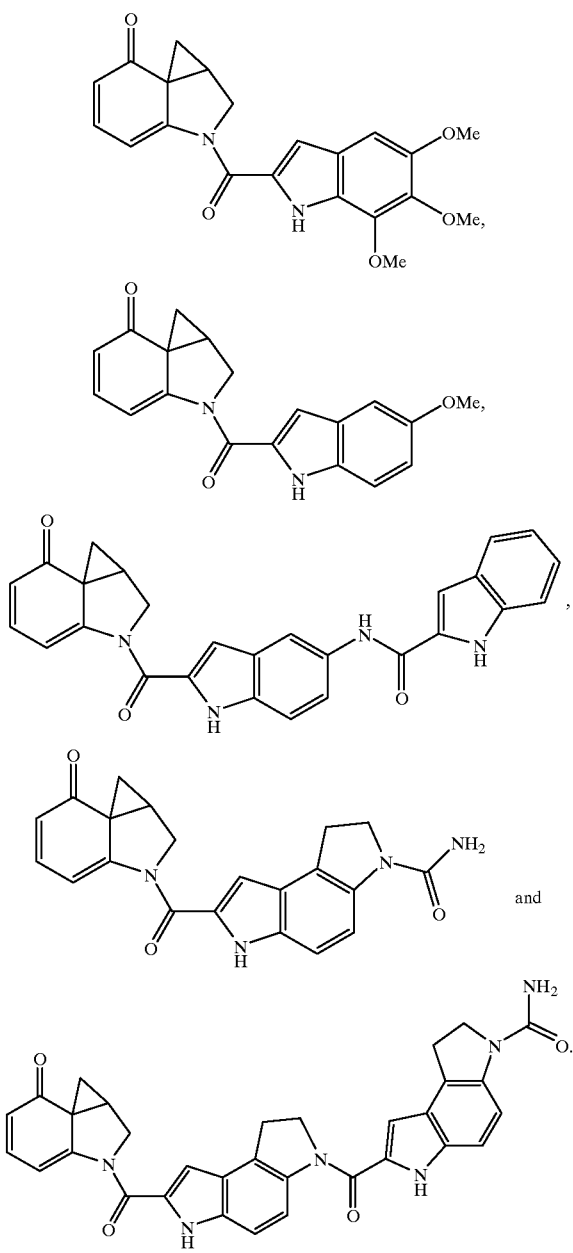

Another aspect of the invention is directed to DNA alkylating compounds represented by the following structure:

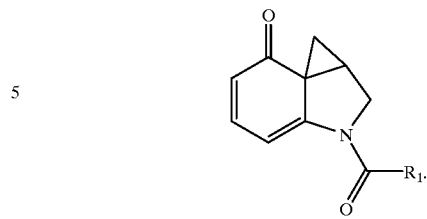

In the above structure $R_1$ is selected from the group consisting of —C1–C6 alkyl, —NHCH$_3$ (—N-alkyl), —OCH$_3$ (O-alkyl), —NH$_2$, —NHNH$_2$, —NHNHCO$_2$$^t$Bu, and a radical represented by the following structure:

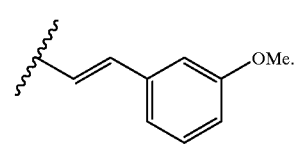

An example of this preferred embodiment is represented by the following structure:

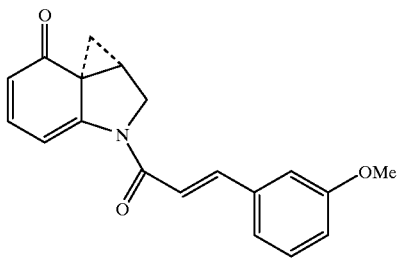

An other aspect of the invention is directed to chemical intermediates represented by the following structures:

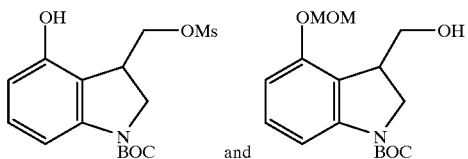

DETAILED DESCRIPTION

Figure 1:
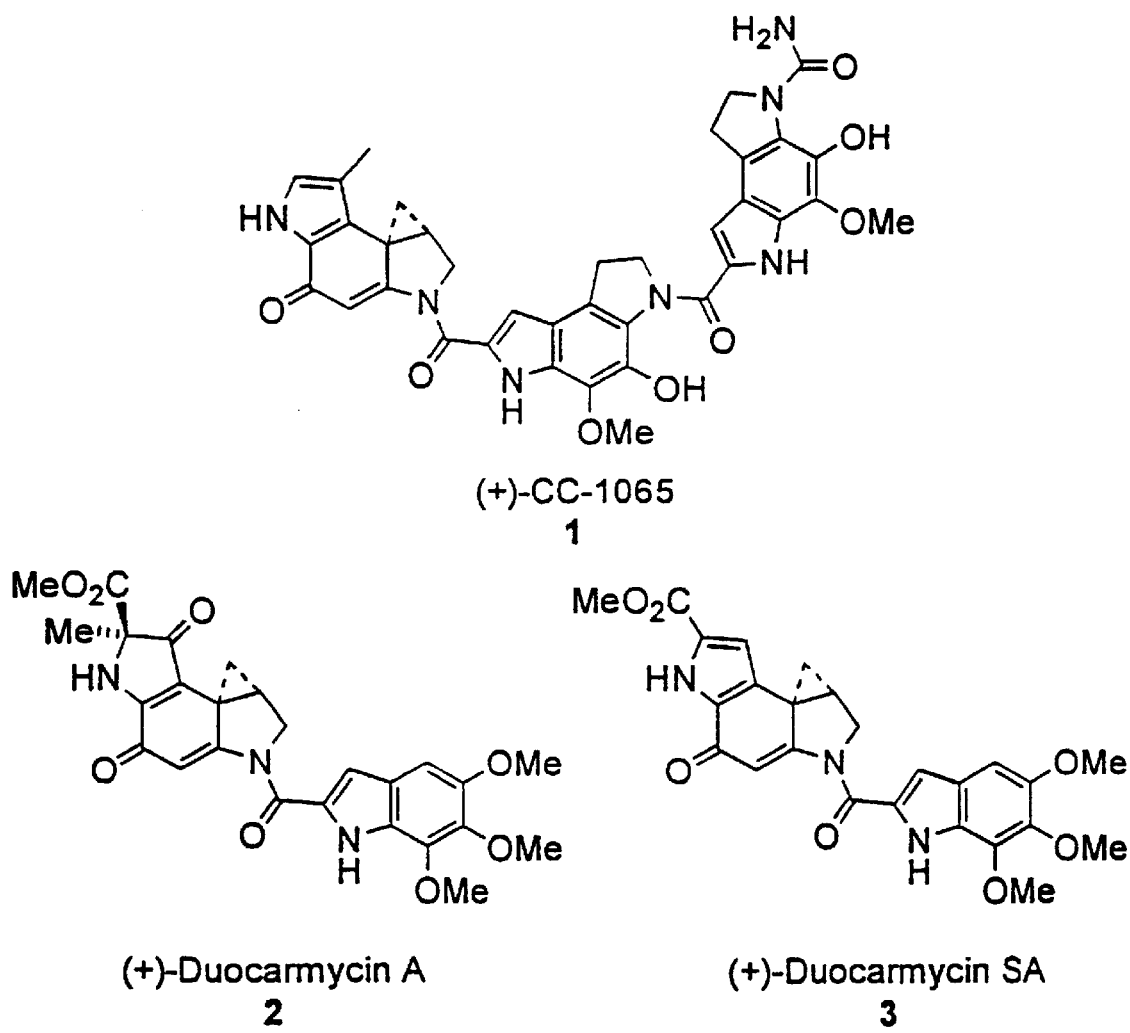
FIG. 1 illustrates (+)-CC-1065 (1) and the duocarmycins 2 and 3, the unmodified natural products.
Figure 2A:
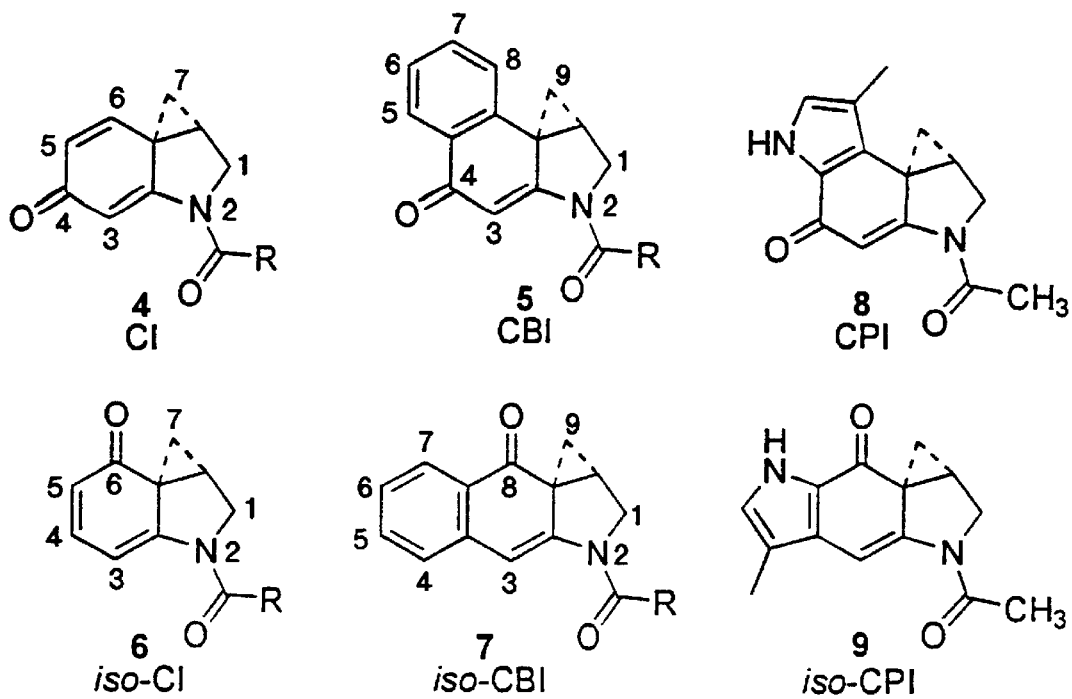
FIG. 2A illustsrates prior art DNA alkylation agents CI, CBI and CPI and novel analog DNA alkylation agents iso-CI, iso-CBI and iso-CPI.
Figure 2B:
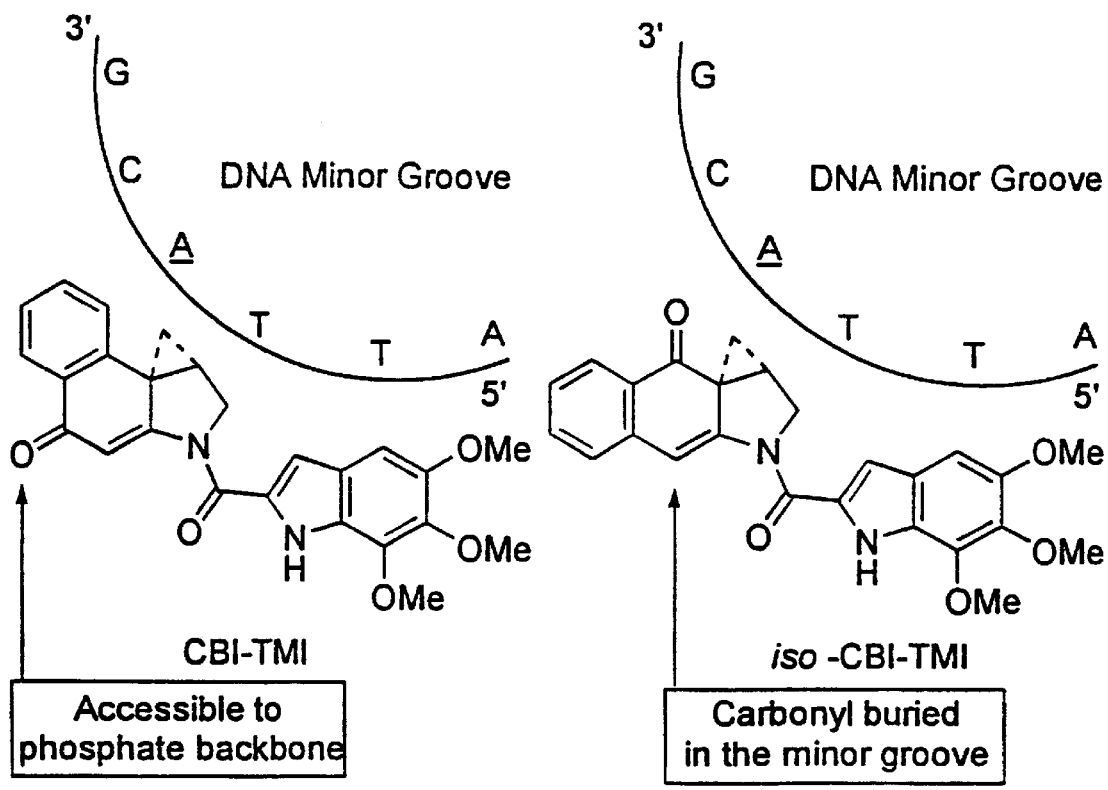
FIG. 2B illustsrate the interactions of CBI-TMI and iso-CBI-TMI with the minor groove of DNA.

Sundberg and co-workers report the first synthesis of agents isomeric to the natural products. (Sundberg, R. J., et al., *Tetrahedron Lett.* 1983, 24, 4773; and Sundberg, R. J., et al., *J. Org. Chem.,* 1991, 56, 3048.) An agent isomeric with the alkylation subunit of CC-1065 was prepared employing an intramolecular

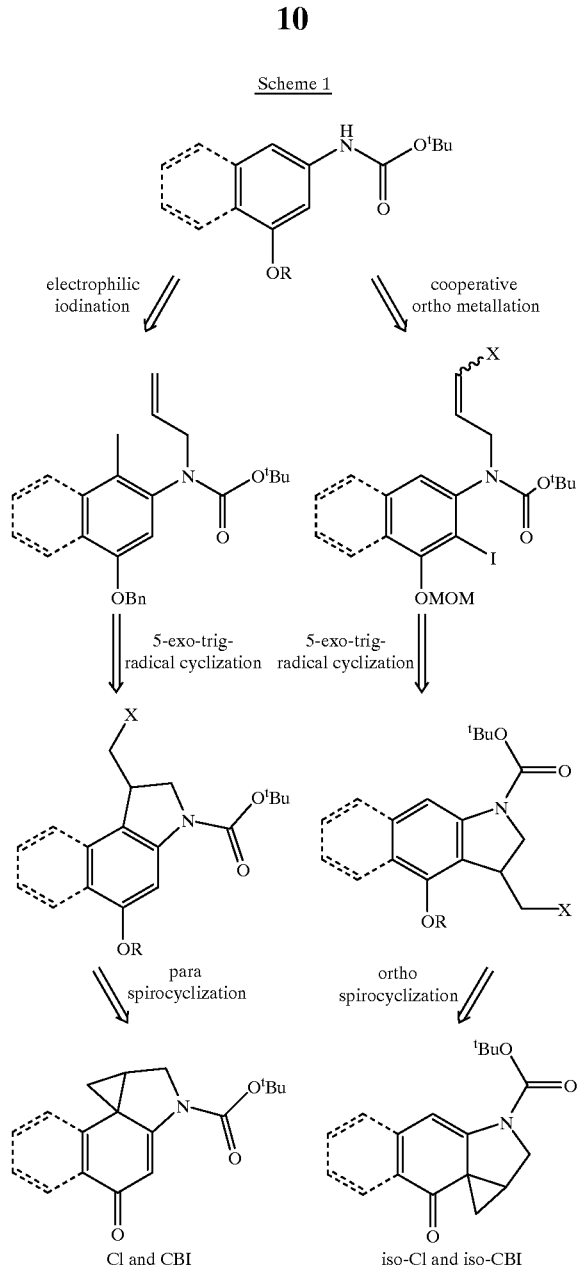

Scheme 1 carbene insertion of an o-quinonediazide onto a tethered alkene. Presumably because of the perceived unique character of the authentic alkylation subunit at the time of the work, its chemical behavior, biological characteristics, and DNA alkylation properties were not examined.

As illustrated above in Scheme 1, an alternative route was subsequently devised for the synthesis of the isomeric CI analogs (Boger, D. L., et al., *J. Am. Chem. Soc.* 1990, 112, 5230.) and for CBI analogs. (Boger, D. L., et al., *J. Org. Chem.* 1995, 60, 1271; Boger, D. L. et al., *J. Org. Chem.* 1992, 57, 2873; Boger, D. L., et al., *J. Am. Chem. Soc.* 1989, 111, 6461; Boger, D. L., et al., *J. Org. Chem.* 1990, 55, 5823; Boger, D. L., et al., *Tetrahedron Lett.* 1990, 31, 793; Boger, D. L., et al., *Bioorg. Med. Chem. Lett.* 1991, 1, 55; Boger, D. L., et al., *Bioorg. Med. Chem. Lett.* 1991, 1, 115; Boger, D. L., et al., *J. Am. Chem. Soc.* 1992, 114, 5487; and Boger, D. L., et al., *Bioorg. Med Chem.* 1995, 3, 611.) The strategy is complementary to our synthesis of CBI in which the dihydroindole skeleton was constructed by a 5-exo-trig radical cyclization of an aryl radical onto a tethered alkene and its extension to the isomeric analogs required C2 versus C4 regiocontrol in the key aromatic halogenation step. In the synthesis of CI and CBI, a regioselective electrophilic halogenation served to install iodine or bromine para to the This approach was first examined with iso-CI employing the commercially available 3-nitrophenol (10), Scheme 2. Protection of the phenol as the MOM ether 11 (NaH, MOMCl, Bu$_4$NI, 89%), reduction of the nitro group with

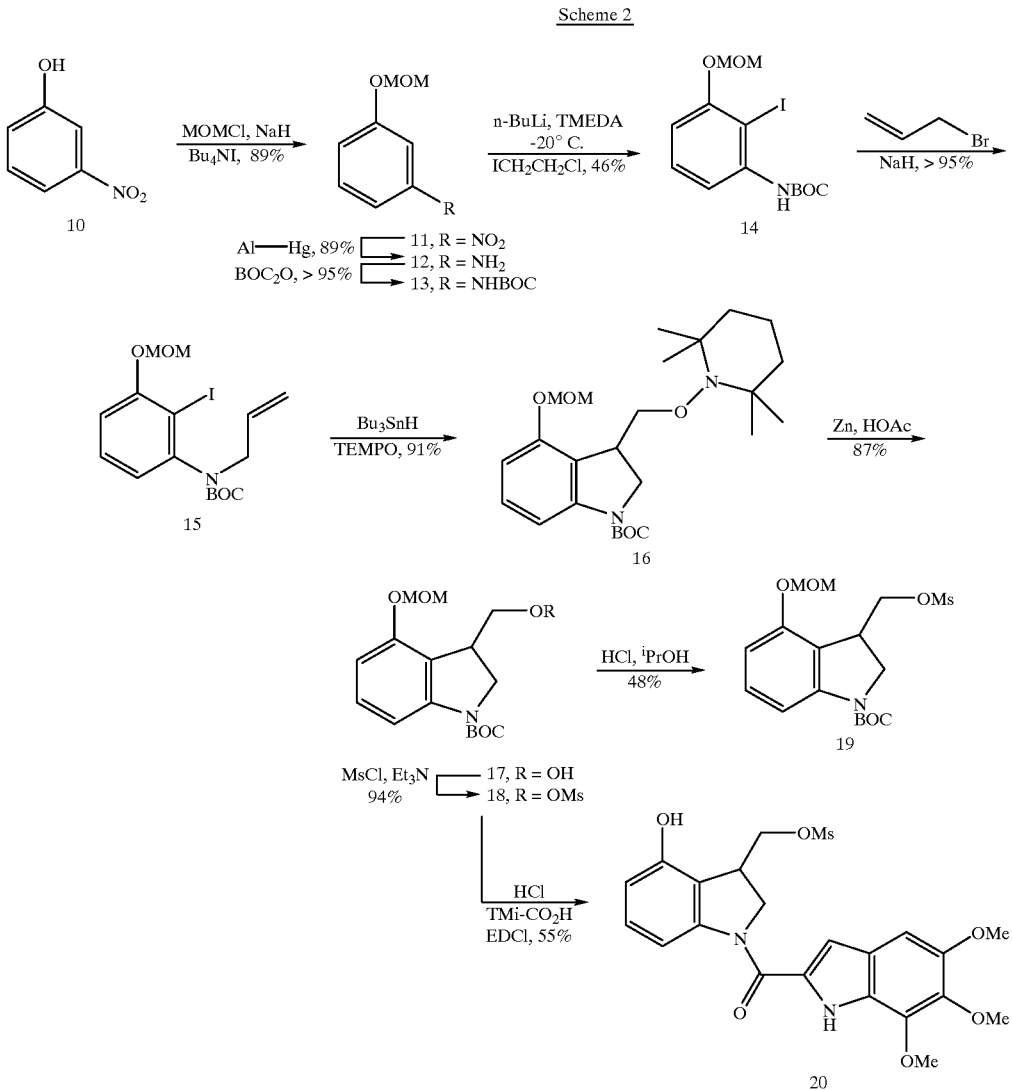

phenol ether. For the isomeric agents, an ortho halogenation protocol was required and a cooperative directed ortho metallation[23] was implemented to install the C2 halide. (Snieckus, V. *Chem. Rev.* 1990, 90, 879.) Its adoption required two easily removed cooperative directing metallation groups: OMOM (Winkle, M. R., et al., *J. Org. Chem.* 1982, 47, 2101) and NHBOC. (Muchkowski, J. M., et al., *J. Org. Chem.* 1980, 45, 4798.) In addition, the Winstein para Ar-3' spirocyclization (Baird, R., et al., *J. Am. Chem. Soc.* 1963, 85, 567; 1962, 84, 788; 1957, 79, 756.) utilized to close the cyclopropane in the CI and CBI synthesis, is now replaced by an ortho spirocyclization requiring C-alkylation with cyclopropane formation (Brown, R. F. C., ete al., *Tetrahedron Lett.* 1981, 22, 2915; Smith III, A. B., et al., *Tetrahedron Lett.* 1987, 28, 3659; and Kigoshi, H., et al., *Tetrahedron Lett.* 1997, 38, 3235) rather than competitive O-alkylation and dihydrofuran formation.

Al—Hg amalgam (Et$_2$O—H$_2$O, 89%) (Meyers, A. I., et al., *J. Org. Chem.* 1975, 40, 2021.), and BOC protection of the free amine 12 (BOC$_2$O,>95%) provided 13, a key intermediate with which to examine the directed ortho metallation. Treatment of 13 with 3.5 equiv of n-BuLi and TMEDA at −20° C. (2 h) in THF, and reaction of the aryl lithium intermediate with 1-chloro-2-iodoethane provided 14 (46%) along with recovered starting material (41%). Although not extensively examined, this conversion was not improved through use of longer reaction times, different reaction temperatures or solvents, or additional amounts of n-BuLi. However, the conversion did allow the synthesis to proceed and, as detailed, this reaction proved much more effective in the iso-CBI series where it was more carefully optimized. N-Alkylation with allyl bromide (NaH, >95%) was followed by Bu$_3$SnH promoted 5-exo-trig free radical cyclization of 15 with in situ TEMPO trap of the resulting primary radical to provide 16 (91%). Subsequent reduction of the N—O bond (Zn, HOAc, 87%) without the competitive deprotection of either the MOM ether or the N-BOC protecting groups afforded the free alcohol 17 in excellent overall yield. Activation of the primary alcohol (MsCl, Et$_3$N, 94%) afforded the key intermediate 18, further detailed below.

In order to prepare N-BOC-iso-CI for direct comparison with prior agents, selective removal of the MOM group in the presence of the BOC group was required. Mild acid-catalyzed deprotection (HCl, i-PrOH/THF, 48%) provided seco-N-BOC-iso-CI (19) accompanied by 41% recovery of starting material. Although not optimized, this selective deprotection found greater success in the synthesis of N-BOC-iso-CBI where it was more closely examined. Exhaustive deprotection of the MOM ether and the BOC group (3.6 M HCl/EtOAc) followed by EDCI-promoted coupling with 5,6,7-trimethoxyindole-2-carboxylic acid (TMI-COOH)[10,31] provided 20 (55% overall). (EDCI=1-(3-dimethylaminopropyl)-3-ethylcarbodiimide hydrochloride; Boger, D. L., et al., *J. Org. Chem.* 1990, 55, 4499.) Consistent with expectations, spirocyclization of 19 to N-BOC-iso-CI (21)

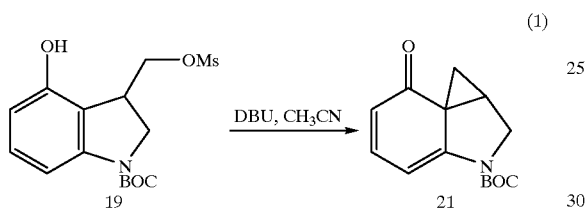

(1)

could be effected by treatment with DBU, but its exceptional reactivity precluded attempts to isolate and characterize the agent (eq 1).(Diagnostic $^1$H NMR (CD$_3$CN, 400 MHz) signals for 21 generated in situ: δ2.79 (dt, J=5.4, 7.8 Hz, 1H), 1.75 (dd, J=3.1, 7.8 Hz, 1H).) Sufficient for our considerations, the studies revealed that N-BOC-iso-CI is more reactive than its counterpart N-BOC-CI which, Scheme 3

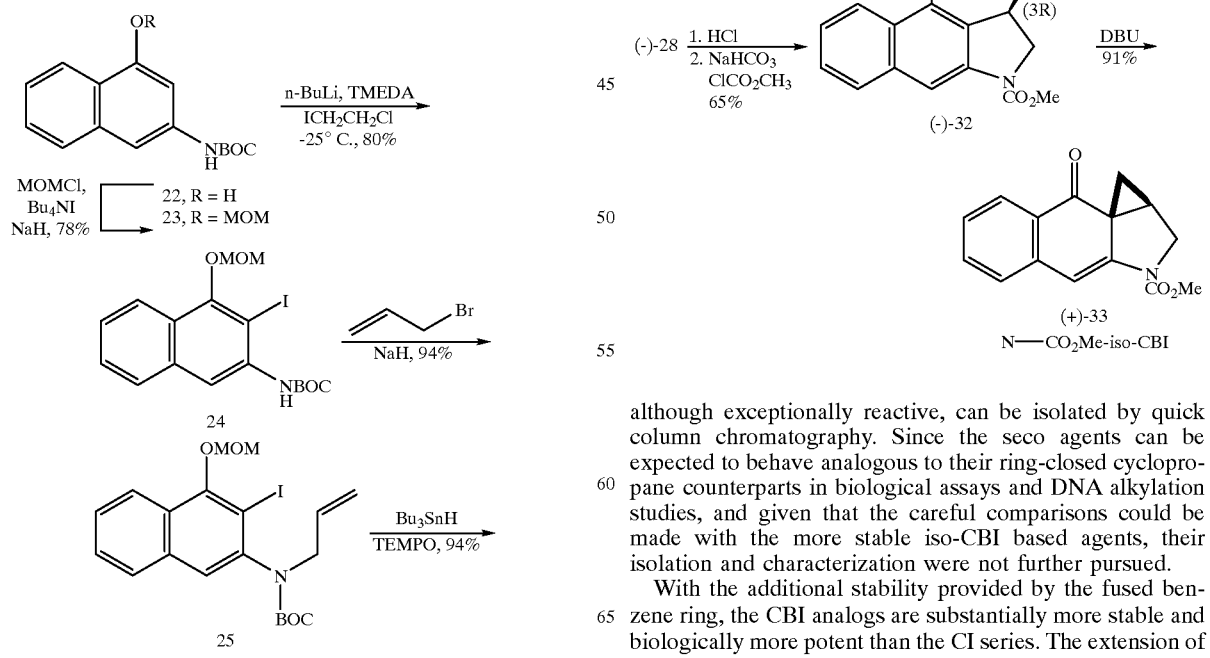

although exceptionally reactive, can be isolated by quick column chromatography. Since the seco agents can be expected to behave analogous to their ring-closed cyclopropane counterparts in biological assays and DNA alkylation studies, and given that the careful comparisons could be made with the more stable iso-CBI based agents, their isolation and characterization were not further pursued.

With the additional stability provided by the fused benzene ring, the CBI analogs are substantially more stable and biologically more potent than the CI series. The extension of this approach to the preparation of of the iso-CBI alkylation subunit is detailed in Scheme 3 and provided the opportunity to accurately document the effects of this deep-seated structural change. Starting with 22, available in two steps (70%) from commercially available 1,3-dihydroxynaphthalene, protection of the phenol (MOMCl, NaH, Bu$_4$NI, 78%) as the MOM ether provided the directed ortho metallation substrate 23. Treatment of 23 with 3.5 equiv of n-BuLi and TMEDA at −25° C. in THF for 2 h and reaction of the aryl lithium intermediate with 1-chloro-2-iodoethane gave the C2 iodide 24 in 80% yield, a substantial improvement over the iso-CI directed metallation. N-Alkylation (NaH, allyl bromide, 94%), 5-exo-trig free radical cyclization of 25 with in situ TEMPO trap (BU$_3$SnH, TEMPO, 94%), and N—O bond reduction of 26 (Zn, HOAc, 87%) provided the primary alcohol 27 in excellent overall yield. Conversion to the chloride 28 upon activation of the primary alcohol under Mitsunobu conditions (Ph$_3$P, CCl$_4$, 90%) provided a resolvable intermediate that served as a penultimate precursor to all analogs. A 5-exo-trig radical cyclization onto a tethered vinyl chloride was shown to provide the 5-membered ring with a suitable leaving group already in place. This concise strategy was adopted for the synthesis of iso-CBI (eq 2). Thus, N-alkylation of 25 with 1,3-dichloropropene proceeded in 96% yield providing the key radical cyclization precursor (29). Treatment with catalytic AIBN (0.1 equiv) and BU$_3$SnH (1.1 equiv) at 80° C. (C$_6$H$_6$) yielded the tricyclic core of iso-CBI (28) in 96% yield. This improved approach shortens the original synthesis by two steps, avoiding reductive removal of the TEMPO group and conversion to 28. With this improvement, the preparation of 28 requires 4 steps and proceeds in 58% yield overall. Removal of the MOM ether (HCl, i-PrOH/THF, 90%) without competitive N-BOC deprotection afforded seco-N-BOC-iso-CBI (30) in superb yield. Ortho spirocyclization (DBU, CH$_3$CN, 96%) provided N-BOC-iso-CBI (31) which could be purified by standard chromatography. Similarly, exhaustive deprotection of 28 (3.6 N HCl/EtOAc) followed by N-acylation with methyl chloroformate provided 32 (65%) and spirocyclization (DBU, CH$_3$CN, 25° C., 91%) afforded 33.

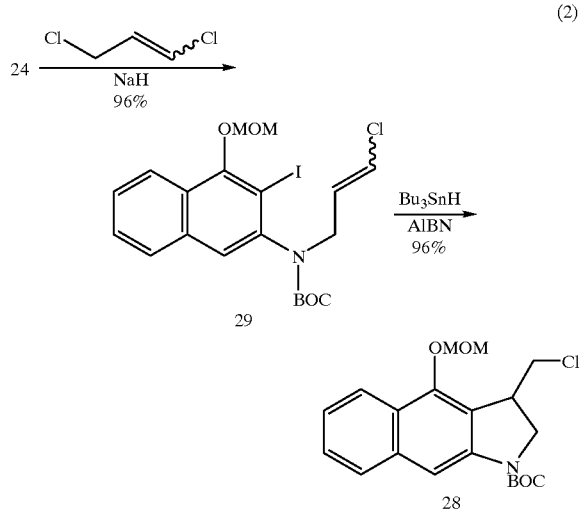

(2)

Initial attempts to synthesize iso-CBI (34) by exhaustive deprotection (3.6 M HCl/EtOAc) and subsequent ring closure (5% aqueous NaHCO$_3$/THF) conducted in the presence of air resulted in the isolation of the quinone 35 (Scheme 4). Presumably, adventious oxidation of the intermediate iso-CBI subsequent to spirocyclization provided 35 and an interesting further modification of the iso-CBI alkylation subunit. (Such agents may be subject to reductive activation.) Consistent Scheme 4

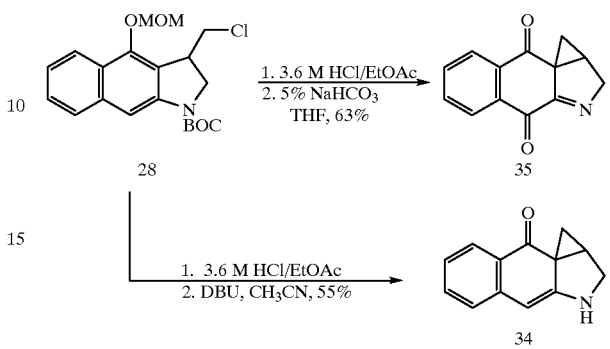

with this, spirocyclization conducted in an aprotic solvent under an inert atmosphere (2.2 equiv DBU, CH$_3$CN, 25° C., 20 min, Ar) provided the unstable iso-CBI (34, 55%) and subsequent exposure of 34 to air resulted in conversion to 35.

Exclusive spirocyclization with cyclopropane formation was observed, and no competitive O-alkylation leading to 36 was detected. However, prolonged exposure of neat 31 to ambient light at 25° C. (48 h) did lead to carbonyl-cyclopropane rearrangement to form 36 (eq 3). (Wong, H. N. C., et al., Chem. Rev. 1989, 89, 165.) An identical neat sample of 31 protected from light by foil remained unchanged after 48 h. Thus, the handling and storage of the iso-CBI based agents were conducted minimizing their exposure to light typically at subzero temperatures. Examination of the compounds over time showed no appreciable decomposition or rearrangement under these storage conditions.

(3)

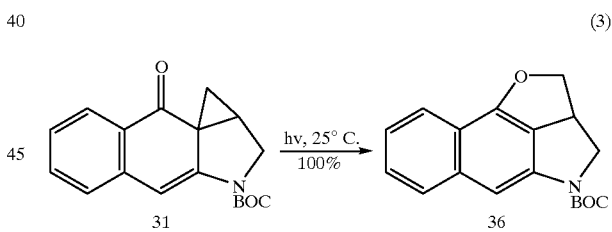

Resolution: In order to assess the properties of both enantiomers of the iso-CBI based agents, a direct chromatographic resolution of 28 on a semipreparative ChiralCel OD column (2×25 cm, 3% i-PrOH/hexane, α=1.24) was utilized. (Boger, D. L., et al., J. Am. Chem. Soc. 1994, 116, 7996.) This procedure provided both enantiomers (>99% ee) of an advanced intermediate and avoided diastereomeric derivatization, separation, and dederivatization. The assignment of absolute configuration was based on the conversion of the slower eluting enantiomer of 28 (t$_R$=35.8 min) to 32 and subsequent single-crystal X-ray structure determination which revealed the unnatural (3R)-configuration (Scheme 3). (The atomic coordinates for this structure have been deposited with the Cambridge Crystallographic Data Centre and may be obtained upon request from the Director, Cambridge Crystallographic Data Centre, 12 Union Road, Cambridge, CB2 1EZ, UK.) Consistent with this assignment, the agents derived from the (3S)-enantiomer analogous to the absolute stereochemistry found in the natural products 1–3 exhibited the more potent biological activity, the more effective DNA alkylation properties, and exhibited a DNA alkylation selectivity identical to the natural products.

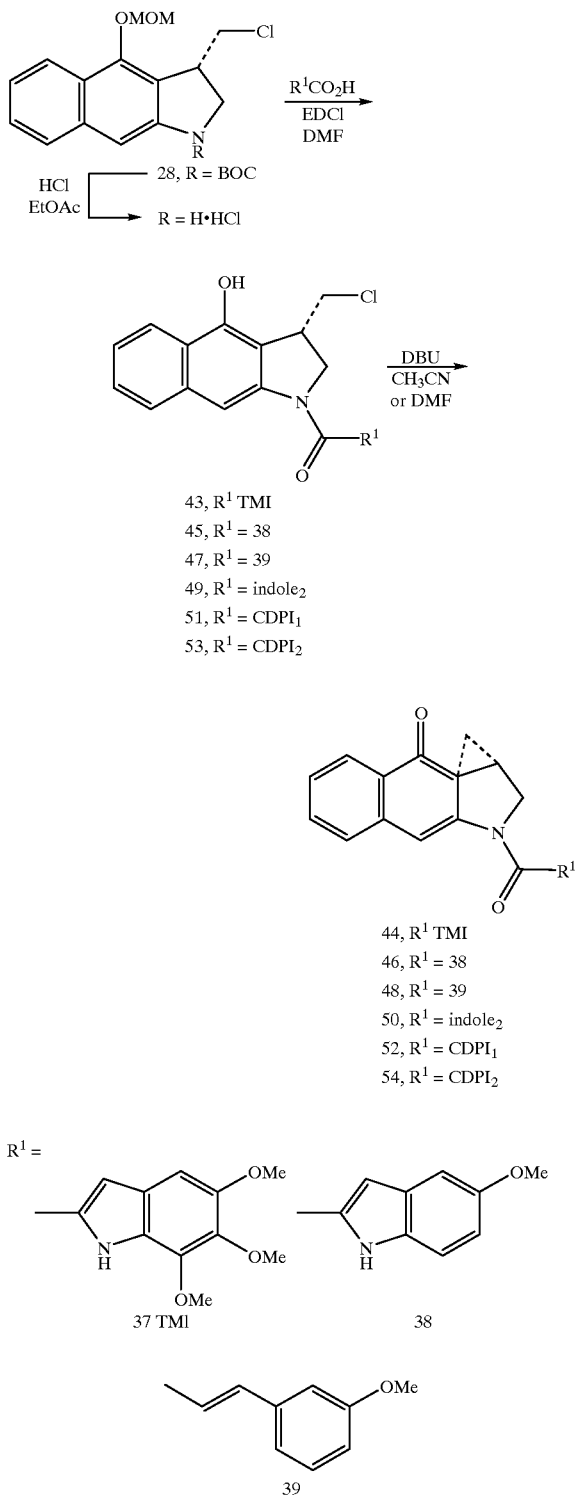

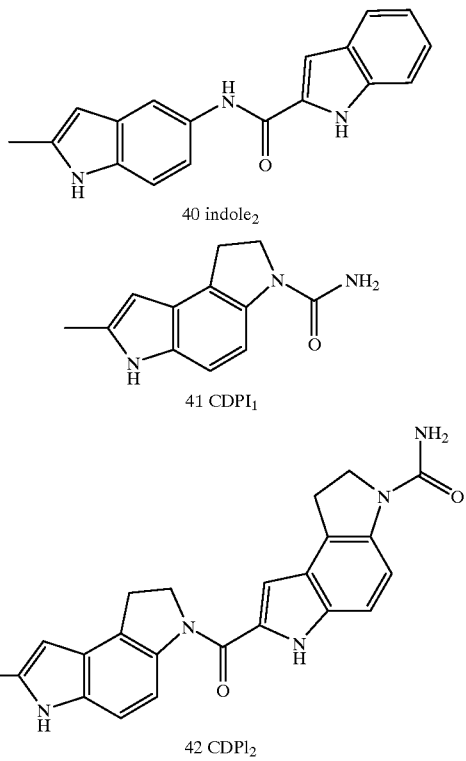

Synthesis of Duocarmycin and CC-1065 Analogs: The iso-CBI alkylation subunit was incorporated into CC-1065 and duocarmycin analogs as detailed in Scheme 5. Exhaustive deprotection of 28 (3.6 M HCl/EtOAc, 30 min) followed by immediate coupling (3 equiv of EDCI, DMF, 25° C.) of the amine hydrochloride salt with 5,6,7-trimethoxyindole-2-carboxylic acid (37, 3 h, 91%), 38 (3 h, 95%), 39 (3 h, 87%), indole$_2$ (40, 3 h, 74%), CDPI$_1$ (41, 9 h, 80%), and CDPI$_2$ (42, 12 h, 32%) provided 43, 45, 47, 49, 51 and 53, respectively. (Boger, D. L., et al., *Bioorg. Med. Chem.* 1995, 3, 1429; Boger, D. L., et al., *J. Org. Chem.* 1987, 52, 1521; and Boger, D. L., et al., *J. Org. Chem.* 1984, 49, 2240.) The poor solubility of CDPI$_2$ precluded efficient coupling and isolation, resulting in a lower yield. DBU (1.5 equiv, 25° C.) spirocyclization of 43 (CH$_3$CN, 30 min, 94%), 45 (CH$_3$CN, 30 min, 85%), 47 (CH$_3$CN, 30 min, 83%), 49 (DMF, 30 min, 88%), 51 (DMF, 60 min, 81%), and 53 (DMF, 60 min, 59%) afforded 44, 46, 48, 50, 52 and 54, respectively, in excellent conversions.

Solvolysis Reactivity and Regioselectivity: Two fundamental characteristics of the alkylation subunits have proven important in past studies. (Boger, D. L., et al., *Angew. Chem., Int. Ed. Engl.* 1996, 35, 1439.) The first is the stereoelectronically-controlled acid-catalyzed ring opening of the activated cyclopropane which dictates preferential addition of a nucleophile to the least substituted cyclopropane carbon. The second is the relative rate of acid-catalyzed solvolysis which has been found to accurately reflect the functional reactivity of the agents and to follow a direct relationship between solvolysis stability and in vitro cytotoxicity. While N-BOC-iso-BCI retains many of the structural characteristics of N-BOC-CBI, the isomeric modifications which may disrupt the vinylogous amide conjugation were anticipated to reduce the solvolytic stability of the agents. However, it was not clear what the magnitude of this effect might be nor whether solvolysis would still occur with the same high regioselectivity.

N-BOC-iso-CBI (31, $t_{1/2}$=27.6 h, k=6.97×10$^{-6}$ s$^{-1}$) and N—CO$_2$Me-iso-CBI (33, $t_{1/2}$=30.1 h, k=6.40×10$^{-6}$ s$^{-1}$) proved to be reasonably stable toward chemical solvolysis at pH 3 exhibiting a reactivity comparable to the CC-1065 alkylation subunit (N-BOC-CPI, 55, $t_{1/2}$=36.7 h), but more stable than the duocarmycin A alkylation subunit (N-BOC-DA, 56, $t_{1/2}$=11 h), Table 1. However,

TABLE 1

Solvolysis Reactivity and Regioselectivity

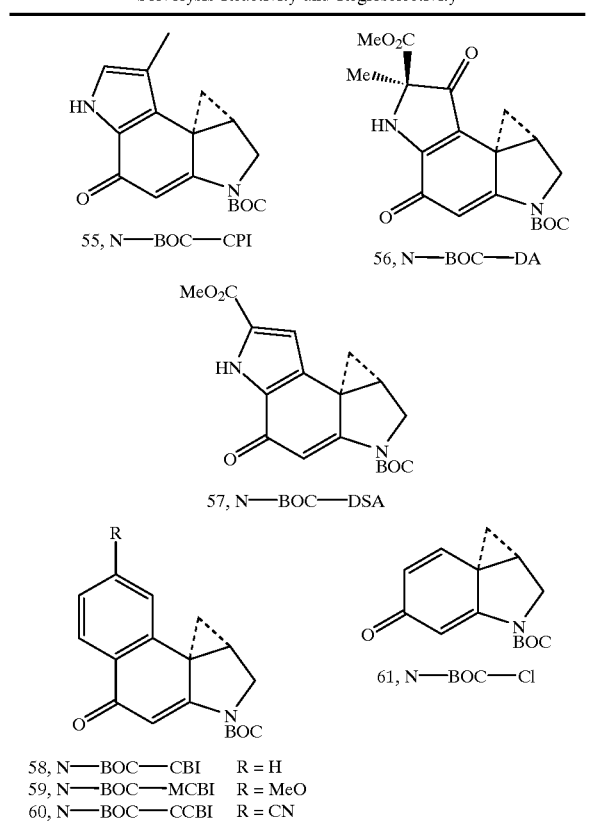

TABLE 1-continued

Solvolysis Reactivity and Regioselectivity

| Agent | k (s$^{-1}$, pH 3) | $t_{1/2}$ (h, pH 3) | Regioselectivity |
|---|---|---|---|
| 31 | 6.98 × 10$^{-6}$ | 28 h | 40:1 |
| 35 | 3.80 × 10$^{-5}$ | 5 h | nd |
| 55 | 5.26 × 10$^{-6}$ | 37 h | 4:1 |
| 56 | 1.75 × 10$^{-5}$ | 11 h | 3:2 |
| 57 | 1.08 × 10$^{-6}$ | 177 h | 6–4:1 |
| 58 | 1.45 × 10$^{-6}$ | 133 h | >20:1 |
| 59 | 1.75 × 10$^{-6}$ | 110 h | >20:1 |
| 60 | 0.99 × 10$^{-6}$ | 194 h | >20:1 |
| 61 | 1.98 × 10$^{-2}$ | 0.01 h | nd |

Figure 3A:
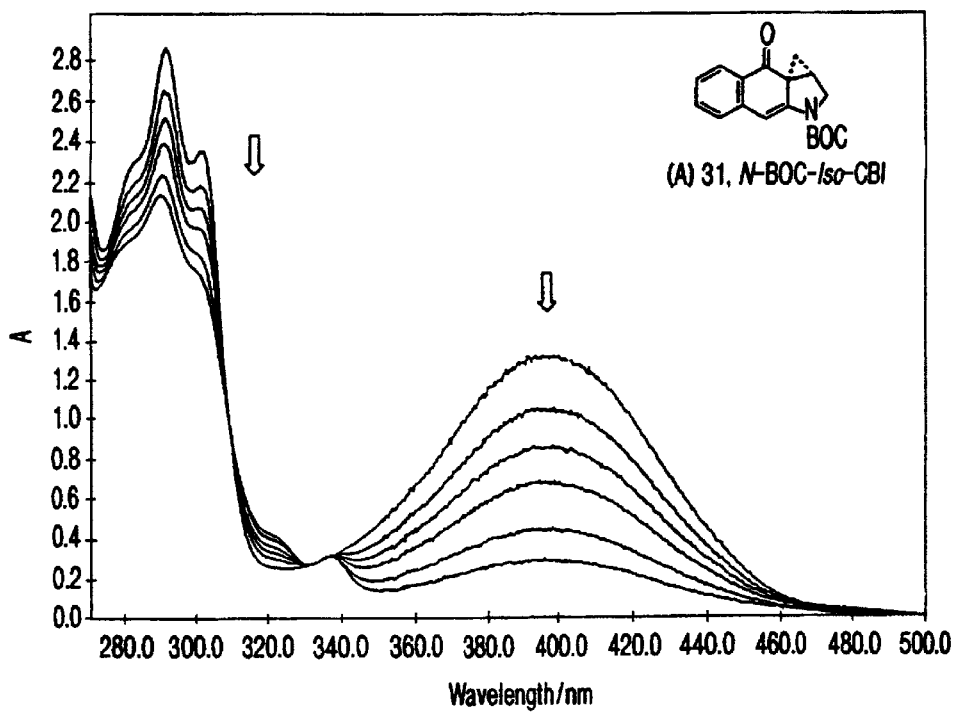
FIG. 3A illustrates data from a solvolysis study (UV spectra) of N-BOC-iso-CBI (31) in 50% CH$_3$OH-aqueous buffer (pH 3.0, 4:1:20) (v/v/v) 0.1 M citric acid, 0.2 M NaH$_2$PO$_4$, and H$_2$O. The spectra were recorded at 0, 10, 20, 28, 56, and 84 hours.
Figure 3B:
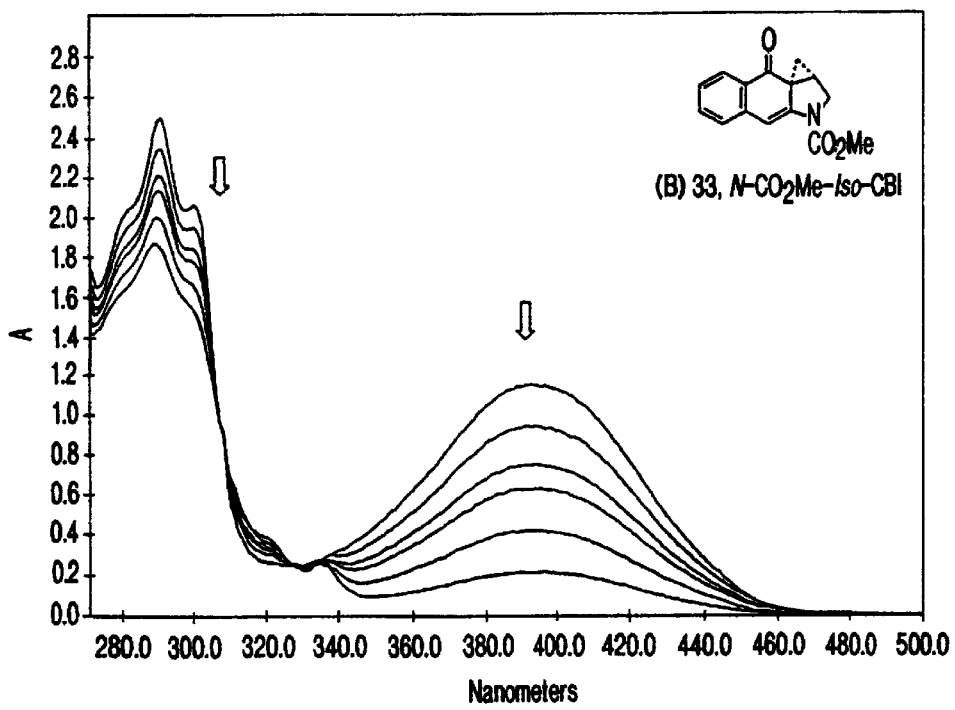
FIG. 3B illustrates data from a solvolysis study (UV spectra) of, N-CO$_2$Me-iso-CBI (33, middle) in 50% CH$_3$OH-aqueous buffer (pH 3.0, 4:1:20) (v/v/v) 0.1 M citric acid, 0.2 M NaH$_2$PO$_4$, and H$_2$O. The spectra were recorded at 0, 10, 21, 29, 57, and 86 hours.
Figure 3C:
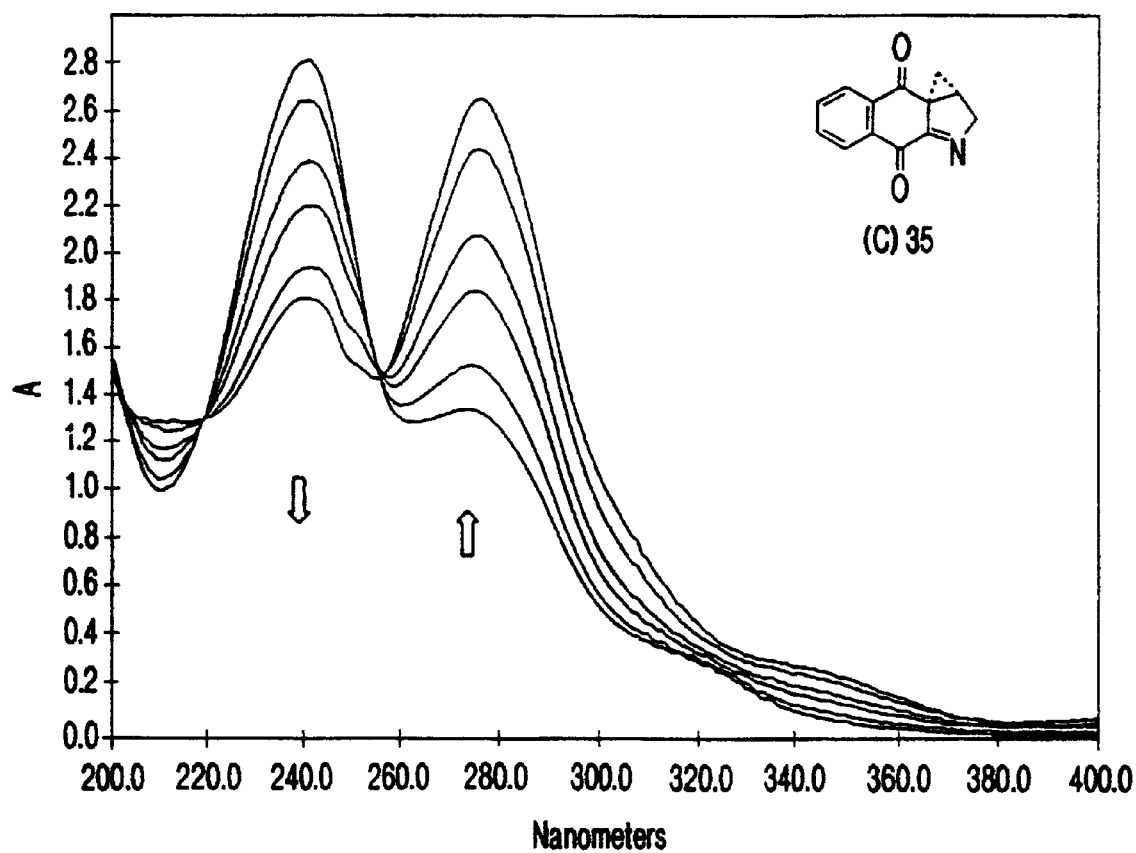
FIG. 3C illustrates data from a solvolysis study (UV spectra) of compound 35 in 50% CH₃OH-aqueous buffer (pH 3.0, 4:1:20) (v/v/v) 0.1 M citric acid, 0.2 M NaH₂PO₄, and H₂O. The spectra were recorded at 0, 1, 3, 5, 10, and 16 hours

N-BOC-iso-CBI was significantly less stable than N-BOC-DSA (57, $t_{1/2}$=177 h) and N-BOC-CBI (58, $t_{1/2}$=133 h). Thus, N-BOC-iso-CBI (31) proved to be 5× more reactive than its direct comparison analog N-BOC-CBI. The solvolysis was followed spectrophotometrically by UV with the disappearance of the long-wavelength absorption band of the iso-CBI chromophore (397 nm), FIG. 3. The reactivity of the quinone 35 was also examined at pH 3 ($t_{1/2}$5.1 h, k=3.80×10$^{-5}$ s$^{-1}$) and it proved to be 5–6× more reactive than 31 or 33.

The acid-catalyzed nucleophilic addition of CH$_3$OH to 31 was conducted on a preparative scale to establish the regioselectivity of addition, and confirmed by synthesis of the expected product 62 derived from nucleophilic addition to the least substituted cyclopropane carbon. Treatment of N-BOC-iso-CBI with 0.1 equiv of CF$_3$SO$_3$H in CH$_3$OH (25° C., 17 h) resulted in the clean solvolysis (94%) to provide a 40:1 mixture of 62 and 63 (Scheme 6). Consequently, the acid-catalyzed CH$_3$OH addition to 31 occurs with near exclusive regioselectivity (40:1) analogous to N-BOC-CBI (58, >20:1) which is much more selective than the natural alkylation subunits themselves (6-1.5:1). (Boger, D. L., et al., Bioorg. Med. Chem. Lett. 1996, 16, 1955; Boger, D. L., et al., J. Am. Chem. Soc. 1997, 119, 311.)

Scheme 6

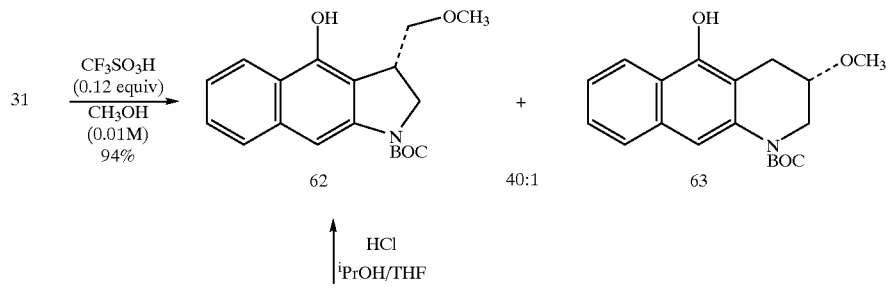

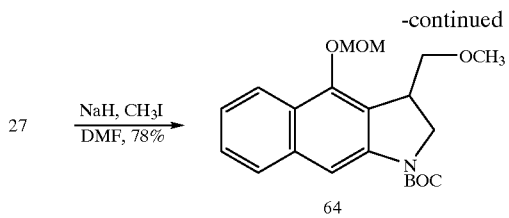

Figure 4A:
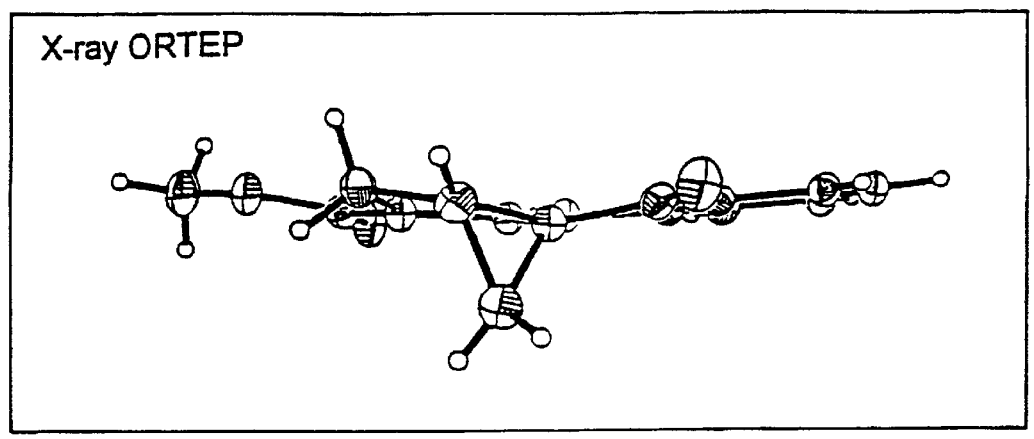
FIGS. 4A–4B illustrate stick models of the side view and 90° roatation view of the activated cyclopropane of N—CO₂Me-iso-CBI and N—CO₂Me-CBI, with data taken from the X-ray crystal structures and highlighting the stereoelectronic and geometric alignment of the cyclopropane with the cyclohexadienone π-system.
Figure 4A:
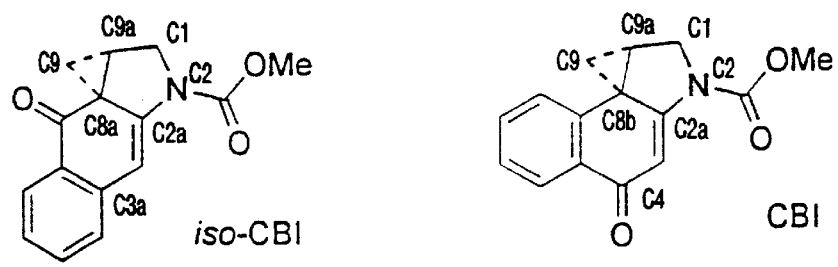
Figure 4B:
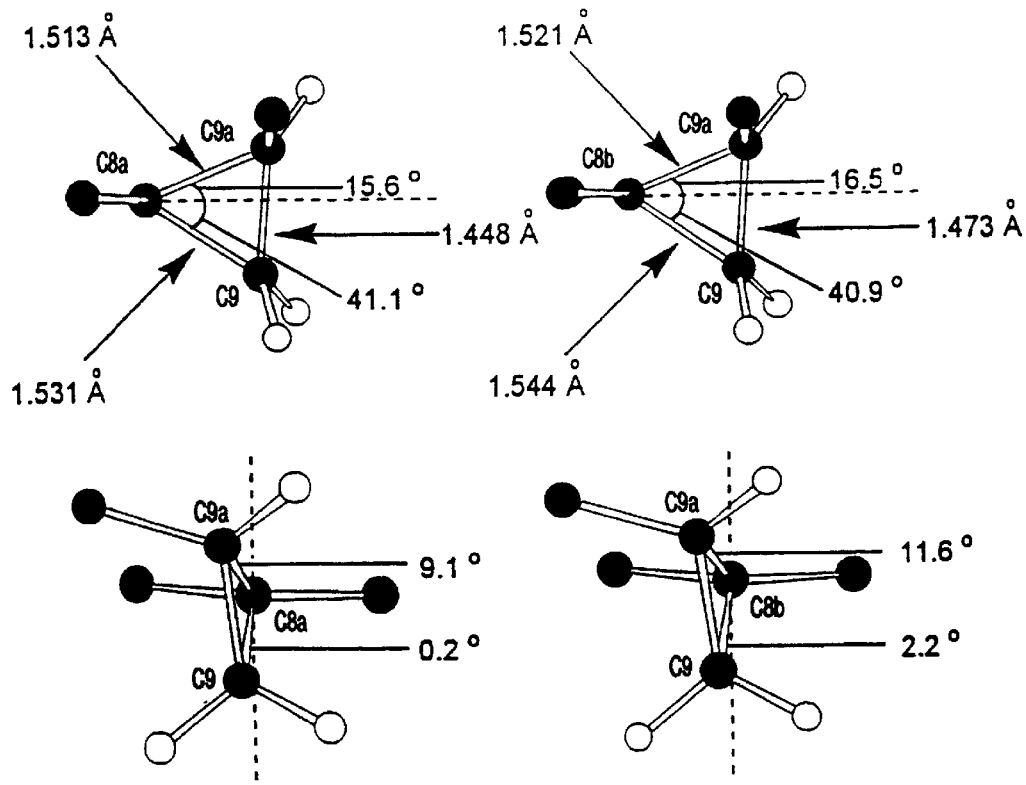

X-Ray Structure of N—CO₂Me-iso-CBI (33): Structural Correlation with Solvolysis Regioselectivity and Reactivity. The single-crystal X-ray structure determination of N—CO$_2$Me-iso-CBI (33) was conducted and by direct comparison with that of N—CO$_2$Me-CBI[42] established a structural basis for the observed properties (FIG. 4). (Boger, D. L.; Turnbull, P. *J. Org. Chem.* 1997, 62, 0000.) The first striking similarity between the two systems is the perpendicular orientation of the bent orbital of the cyclopropane bond extending to the least substituted C9 cyclopropane carbon. This idealized stereoelectronic alignment with the developing π-system of the solvolysis product phenol imposes a preference for nucleophilic addition to the less substituted C9 cyclopropane carbon. In contrast, the cyclopropane bond extending to the tertiary C9a carbon is nearly orthogonal to the π-system of the cyclohexadienone, and S$_N$2 addition to this carbon is disfavored stereoelectronically as well as sterically. The relative cyclopropane bond lengths of iso-CBI reflect this orientation and π conjugation in which the breaking C9—C8a cyclopropane bond (1.531 Å) is longer, and thus weaker, than the C9a—C8a bond (1.513 Å) extending to the more substituted carbon. Although the ring expansion solvolysis would place a developing positive charge on a preferred secondary versus primary carbon, this inherent preference is overridden by the stereoelectronic control of the reaction regioselectivity as well as the characteristics of a S$_N$2 reaction which prefer attack at the less substituted center.

In addition, the X-ray structures have provided insights into the origin of the difference in stability between CBI and iso-CBI. The stability of CC-1065, the duocarmycins and their analogs is a result of at least three structural features: the conjugative stability provided by the fused aromatic system, the non-ideal alignment of the cyclopropane, and the strong cross-conjugative stability provided by the vinylogous amide. The first of these features, the fused aromatic ring, is present in both iso-CBI and CBI. Like the CI/CBI comparison, the iso-CI/iso-CBI reactivity comparison reveals that the diminished aromatization driving force for iso-CBI relative to iso-CI contributes significantly to the stability. In addition, The cyclopropane alignments with the π-systems in N—CO$_2$Me-iso-CBI and N—CO$_2$Me-CBI are similar. Both are bisected by the plane of the cyclohexadienone nearly equally (41°/15° for iso-CBI and 41°/16° for CBI). In both, the cyclopropane is not only pulled down but also to the side by the constraints of the fused 5-membered ring (9° for iso-CBI and 12° for CBI). Thus, both benefit in stability from the non-ideal alignment and conjugation of the cyclopropane which is imposed by the fused 5-membered ring. The important distinction between the two systems is the direct cross-conjugated stability afforded the activated cyclopropane by the vinylogous amide. Diagnostic of this vinylogous amide conjugation is the shortened length of the $N^2$—$C^{2a}$ bond reflecting this resonance stabilization. As this cross-conjugated vinylogous amide stabilization decreases, the conjugation and inherent reactivity of the cyclopropane correspondingly increases. Consistent with this, N—CO$_2$Me-iso-CBI exhibits a $N^2$—$C^{2a}$ bond length (1.400 Å versus 1.426 Å for 32) indicative of a diminished but not eliminated vinylogous amide conjugation relative to N—CO$_2$Me-CBI (1.390 Å versus 1.416 Å for seco N—CO$_2$Me-CBI)[42] and that follows trends established in recent studies (Table 2).

TABLE 2

| agent | $N^2$—$C^{2a}$ bond length (Å) | t½(h, pH 3) |
|---|---|---|
| N-CO$_2$Me-CBI[42] | 1.390 | 133 |
| N-CO$_2$Me-iso-CBI | 1.400 | 28 |
| N-BOC-CBQ[43] | 1.415 | 2.1 |
| N-CO$_2$Me-CNA[42] | 1.428 | 0.03 |

DNA Alkylation Selectivity and Efficiency: The DNA alkylation properties of the agents were examined within w794 and w836 duplex DNA for which comparative results are available for related agents. (Boger, D. L., et al., *J. Am. Chem. Soc.* 1994, 116, 11335; Boger, D. L., etal., *J. Am. Chem. Soc.* 1994, 116, 6461; and Boger, D. L., et al., *J. Am. Chem. Soc.* 1995, 117, 11647) The alkylation site identification and the assessment of the relative selectivity among the available sites were obtained by thermally-induced strand cleavage of the singly 5' end-labeled duplex DNA after exposure to the agents. Following treatment of the end-labeled duplex DNA with a range of agent concentrations and temperatures in the dark, the unbound agent was removed by EtOH precipitation of the DNA. Redissolution of the DNA in aqueous buffer, thermolysis (100° C., 30 min) to induce strand cleavage at the sites of DNA alkylation, denaturing high-resolution polyacrylamide gel electrophoresis (PAGE) adjacent to Sanger dideoxynucleotide sequencing standards, and autoradiography led to identification of the DNA cleavage and alkylation sites. The full details of this procedure have been disclosed elsewhere. (Boger, D. L., et al., *Tetrahedron* 1991, 47, 2661.)

Figure 5:
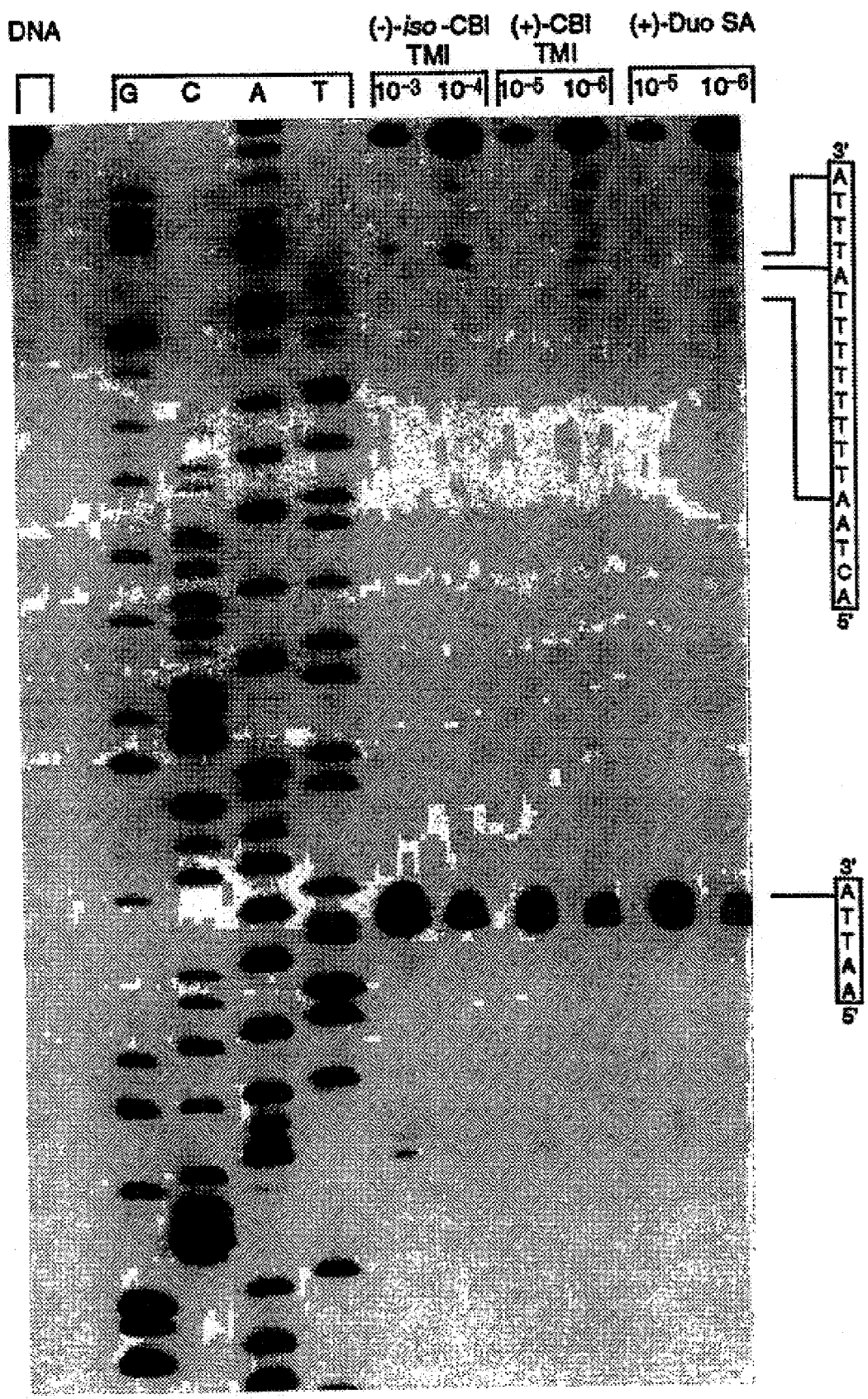
FIG. 5 illustrates thermally-induced strand cleavage of w794 DNA (SV40 DNA segment, 144 bp, nucleotide nos. 138–5238); DNA-agent incubation for 24 hours at 25° C., removal of unbound agent and 30 minutes of thermolysis (100° C.), followed by denaturing 8% PAGE and autoradiography; lane 1, control DNA; lanes 2–5, Sanger G, C, A, and T sequencing reactions; lanes 6–7 (−)-iso-CBI-TMI (1×10⁻³ and 1×10⁻⁴ M); lanes 8–9, (+)-CBI-TMI (1×10⁻⁵ and 1×10⁻⁶ M); lanes 10–11, (+)-duocarmycin SA (1×10⁻⁵ and 1×10⁻⁶).

A representative comparison of the DNA alkylation by (−)-iso-CBI-TMI (44) alongside that of (+)-duocarmycin SA and (+)-CBI-TMI is illustrated in FIG. 5. There are three important conclusions that can be drawn from these comparisons. First, (−)-iso-CBI-TMI alkylates DNA in a manner identical to (+)-duocarmycin SA and (+)-CBI-TMI exhibiting the same sequence selectivity. No new sites of alkylation were detected, and only adenine N3 alkylation was detected under the conditions of limiting agent and excess DNA. Notably, such sequencing studies only detect the higher affinity alkylation sites and minor sites of comparable affinities (1–0.01×). Under these conditions, the studies illustrate that iso-CBI-TMI, like duocarmycin SA and CBI-TMI, exhibits an exclusive preference for adenine versus guanine N3 alkylation. However, given the reactivity of iso-CBI-TMI, it is likely that a minor guanine alkylation could be expected at incubations carried out at higher agent-base pair ratios analogous to that observed with the more reactive agents including CC-1065 (Park, H.-J., et al., *J. Am. Chem. Soc.* 1997, 119, 629.) and duocarmycin A.[46] (Sugiyama, H., et al., *Tetrahedron Lett.* 1993, 34, 2179; Yamamoto, K., et al., *Biochemistry* 1993, 32, 1059; and Asai, A., et al., *J. Am. Chem. Soc.* 1994, 116, 4171.) Importantly, the identical behavior of (−)-iso-CBI-TMI and (+)-CBI-TMI illustrate that the position of the C-4 carbonyl does not influence the sequence selectivity of the DNA alkylation. This is inconsistent with the proposal of a sequence-dependent phosphate backbone protonation of the C-4 carbonyl for activation of the agent for DNA alkylation that controls the sequence selectivity. It is, however, fully consistent with the model in which it is controlled by the AT-rich noncovalent binding selectivity of the agents and their steric accessibility to the adenine N3 alkylation sites.

Secondly, although there are no distinctions in the sequence selectivity, there is a significant difference in the relative efficiencies of DNA alkylation. Consistent with its relative reactivity and cytotoxic potency, (−)-iso-CBI-TMI alkylated DNA 50–100× less efficiently than (+)-CBI-TMI and (+)-duocarmycin SA. Thus, (−)-iso-CBI-TMI was found to alkylate DNA with an efficiency comparable to duocarmycin A which has been shown to be ca. 10× less efficient than duocarmycin SA.[10,11] In addition and analogous to the observations made with the agents containing the more reactive alkylation subunits including duocarmycin A, but unlike the more stable agents, the alkylation efficiency of (−)-iso-CBI-TMI was found to increase as the incubation temperature was decreased from 25° C. to 4° C. This suggests that the differences may be attributed in part to the nonproductive solvolysis of iso-CBI-TMI which competes with alkylation and lowers the overall efficiency of DNA alkylation.

Thirdly, although the rate of DNA alkylation by 44 was not accurately quantitated, it is qualitatively similar to those of CBI-TMI and duocarmycin SA and much faster than agents we have examined which exhibited substantially diminished rates (e.g. reversed analogs of duocarmycin SA). Thus, the relocation of the C-4 carbonyl did not impact the rate of DNA alkylation in a manner that would be consistent with a phosphate backbone protonation (or cation Lewis acid complexation) required of catalysis in the alkylation site model.

Figure 6:
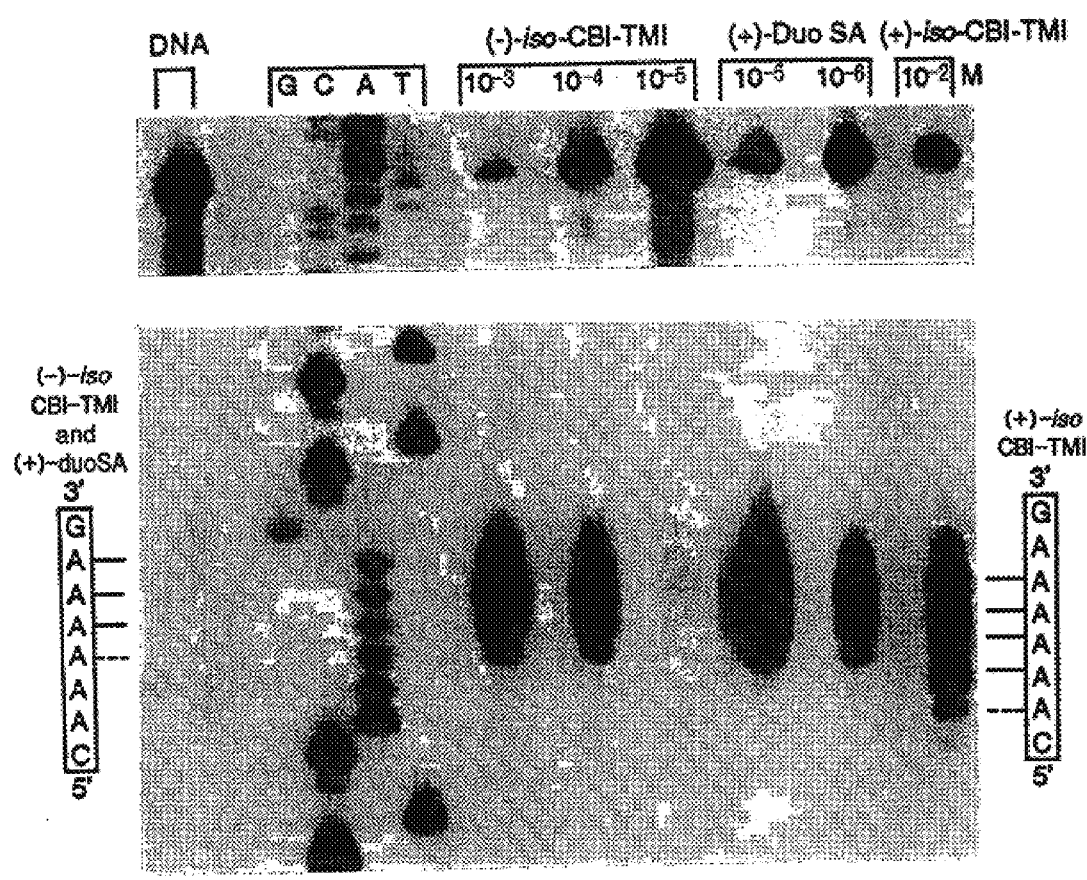
FIG. 6 illustsrates thermally-induced strand cleavage of w836 DNA (146 bp, nucleotide nos. 5189–91): DNA-agent incubation for 24 h ((−)-iso-CBI-TMI) at 25° C., removal of unbound agent and 30 min of thermolysis (100° C.), followed by denaturing 8% PAGE and autoradiography; lane 1, control DNA; lanes 2–5, Sanger G, C, A, and T sequencing reactions; lanes 6–8 (−)-iso-CBI-TMI (1×10³ to 1×10⁻⁵ M); lanes 9–10, (+)-duocarmycin SA (1×10⁻⁵ to 1×10⁻⁶ M); lanes 11–12, (+)-iso-CBI-TMI (1×10⁻² and 1×10⁻³).

Similar results were obtained within w836 DNA (FIG. 6). The natural enantiomer (−)-iso-CBI-TMI alkylated the same sites as (+)-duocarmycin SA but did so with a 50–100 fold lower efficiency. Within the segment illustrated, the two natural enantiomers alkylated the first three 3' adenines in the sequence 5'-AAA<u>AAA</u> and less effectively the fourth 3' adenine corresponding to alkylation and 3'→5' binding across a 3–4 base-pair AT-rich site (i.e., 5'-AAA<u>A</u>>5'-CAA A). Like the unnatural enenatiomer of CBI-TMI, the unnatural enantiomer, (+)-iso-CBI-TMI, alkylated DNA 50–100× less effectively than the natural enantiomer and did so with a selectivity identical to that of ent-(−)-duocarmycin SA. Within w836, this constitutes the central adenines within the sequence 5'-A<u>AAAA</u>A and corresponds to alkylation of 3–4 base-pair AT-rich sites with binding in the reverse 5'→3' direction. Because of the diastereomeric nature of the adducts, the unnatural enantiomer alkylates the second 5' base (adenine) within the sequence (ie., 5-A<u>A</u>AA >5'-C AAAA). This has been discussed in detail and illustrated elsewhere[4] and both enantiomers of iso-CBI-TMI conform nicely to the models. Thus, the relocation of the C-4 carbonyl from the outer face of a bound complex potentially proximal to the phosphate backbone to a position deep in the minor groove inaccessible to the phosphates had no impact on the DNA alkylation selectivity of either enantiomer.

Figure 7:
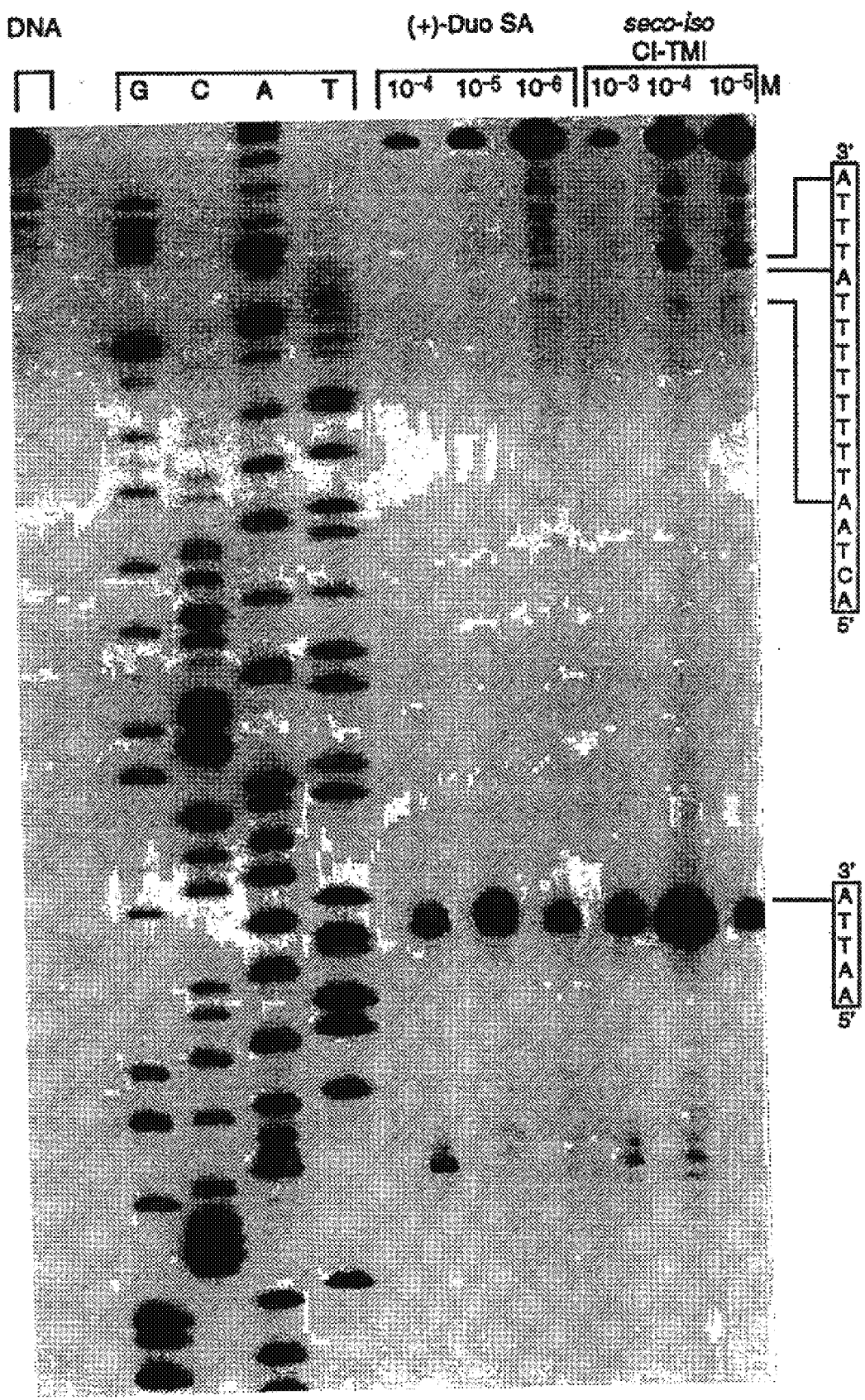
FIG. 7 illustrates thermally-induced strand cleavage of w794 DNA (SV40 DNA segment, 144 bp, nucleotide nos. 138–5238); DNA-agent incubation for 24 h at 25° C., removal of unbound agent and 30 min of thermolysis (100° C.), followed by denaturing 8% PAGE and autoradiography; lane 1, control DNA; lanes 2–5, Sanger G, C, A, and T sequencing reactions; lanes 6–8 (+)-duocarmycin SA (1×10⁻⁴ to 1×10⁻⁶ M); lanes 9–11, seco-iso-CI-TMI (1×10⁻³ to 1×10⁻⁵ M).
Figure 8A:
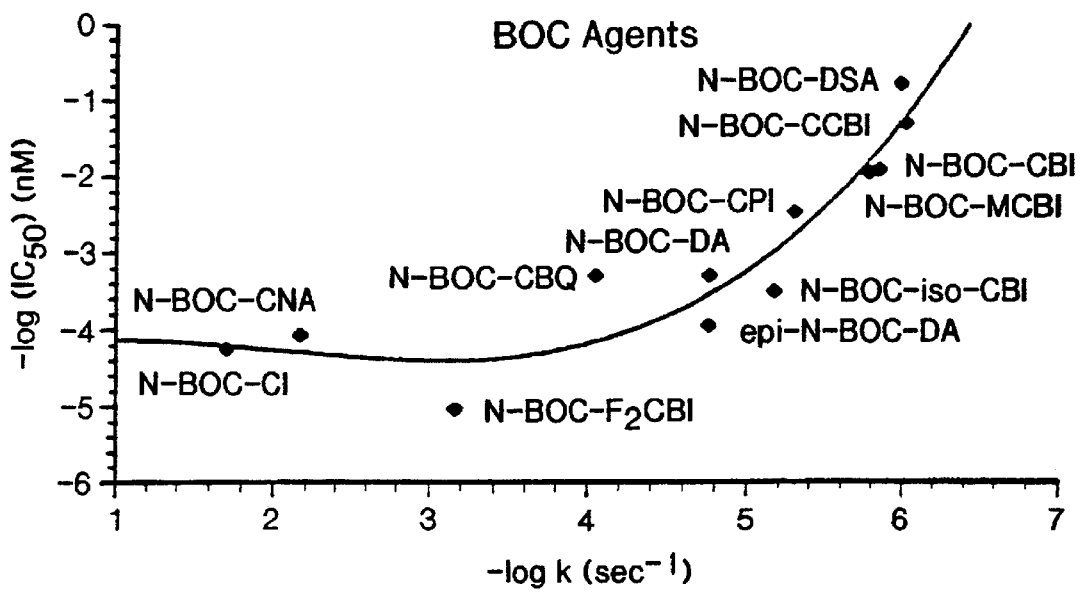
FIGS. 8A–8E illustrate IC₅₀ values for the indicated families of DNA alkylating agents.
Figure 8B:
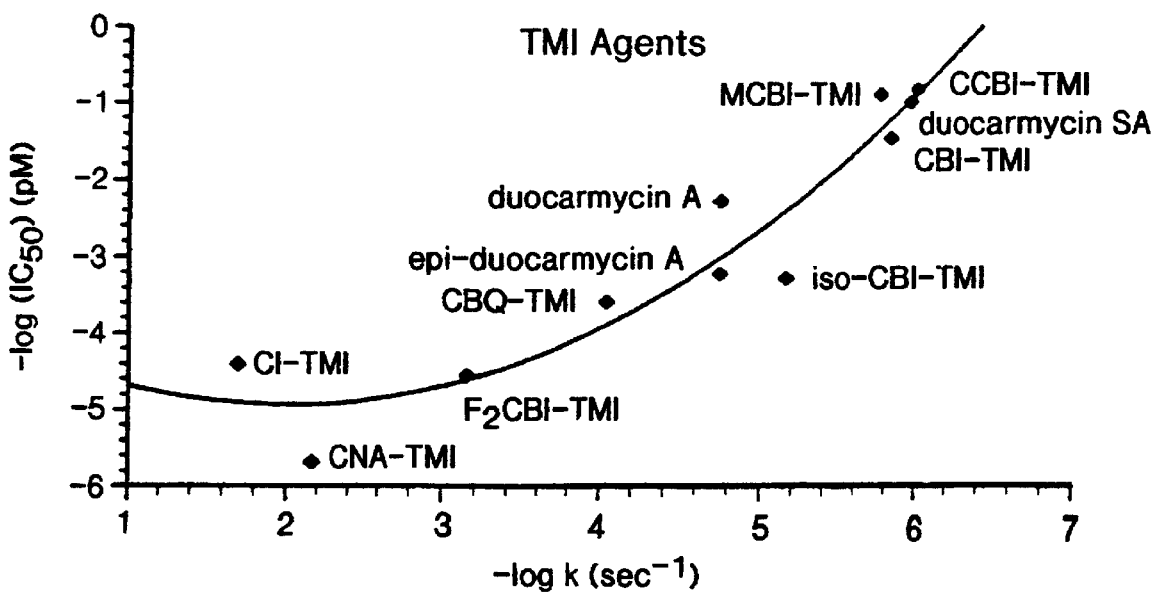
Figure 8C:
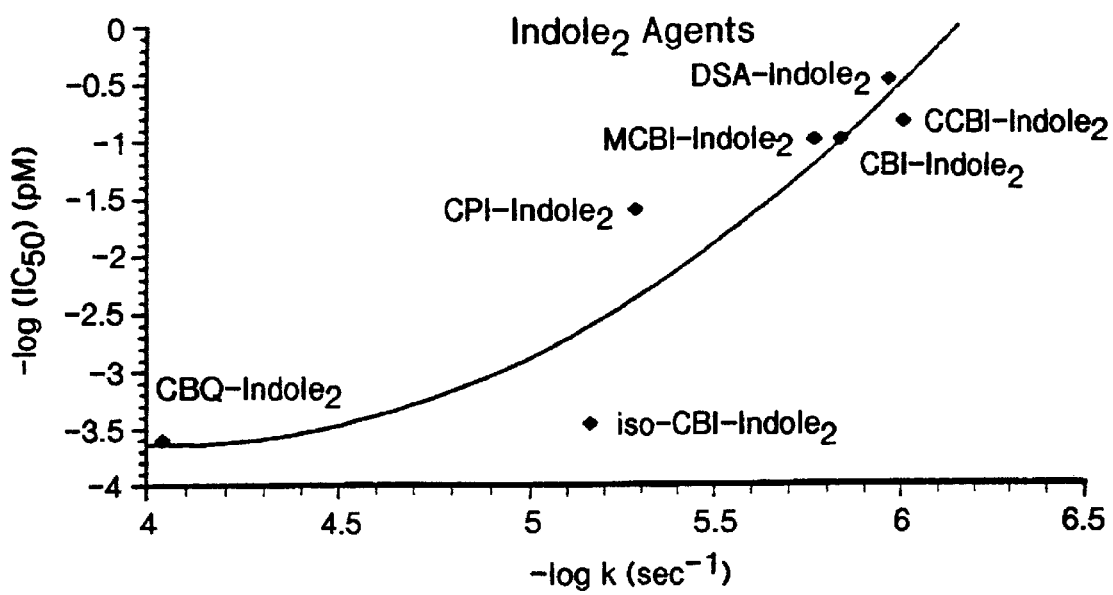
Figure 8D:
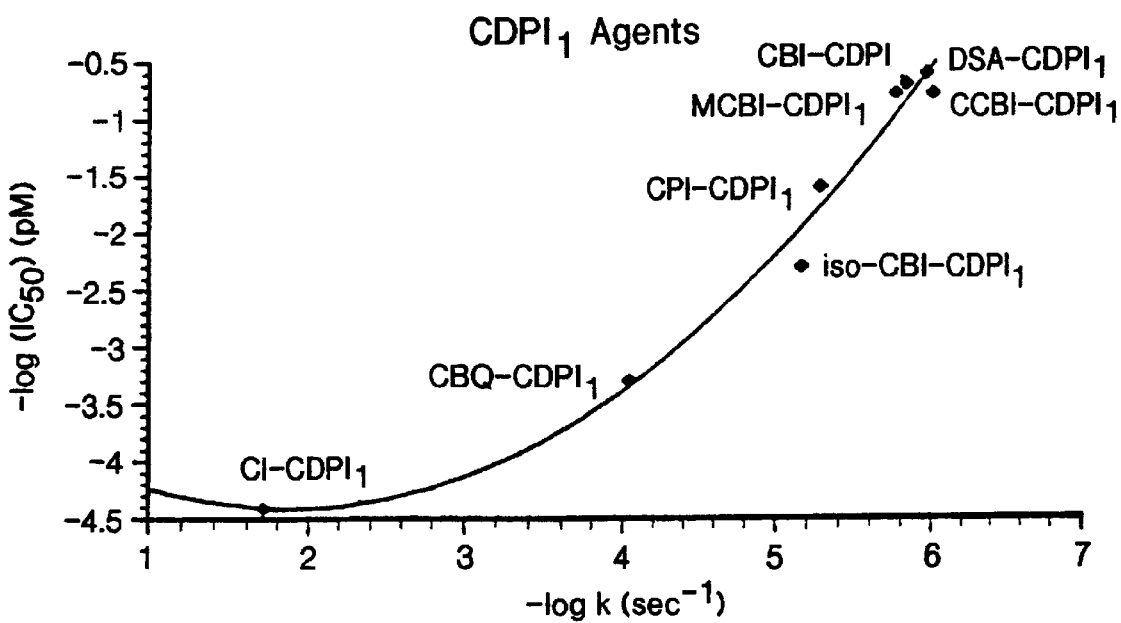
Figure 8E:
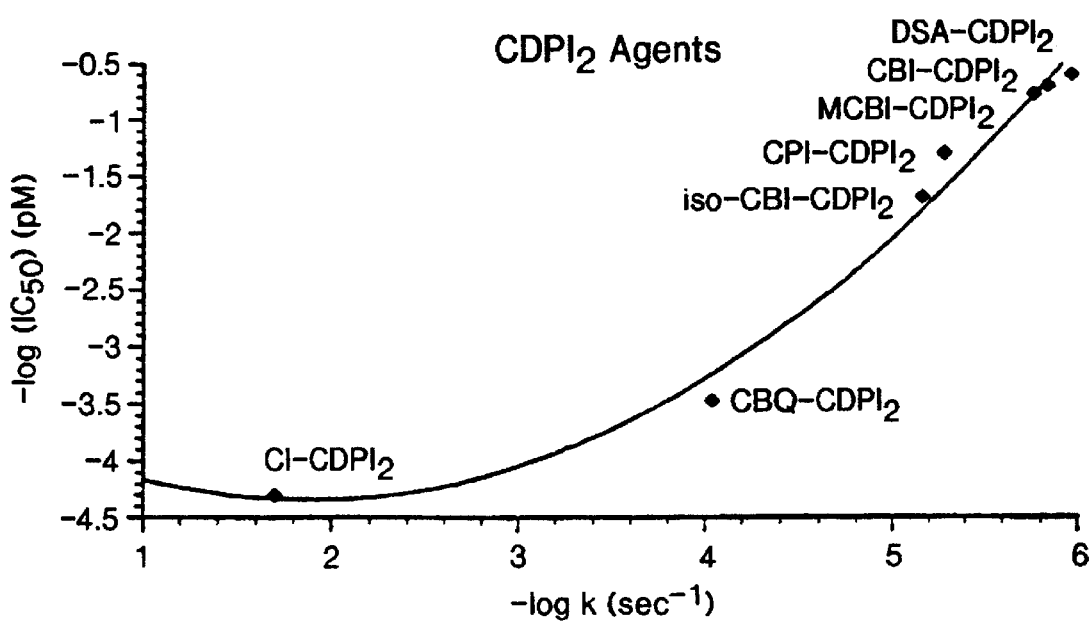

In addition, the DNA alkylation properties of 20, seco iso-CI-TMI, were examined alongside (+)-duocarmycin SA and a representative comparison is illustrated in FIG. 7 with w794 DNA. In past studies, such seco agents have behaved in a manner indistinguishable from their cyclopropane ring-closed counterparts exhibiting identical DNA alkylation selectivities, efficiencies, and cytotoxic activity indicating that ring closure is not limiting under the assay conditions. Since we were not able to isolate the ring closed iso-CI agents because of their exceptional reactivity, the examination was conducted with the seco precursor 20. Analogous to the observations made with iso-CBI-TMI, 44 alkylated DNA in a manner identical to duocarmycin SA alkylating only adenine and exhibiting the same sequence selectivity. Although no new sites of alkylation were detected, the relative selectivity among the available sites was slightly lower with 20. This is illustrated nicely in FIG. 7 where 20 alkylates the minor sites more prominently than does (+)-duocarmycin SA. Interestingly and importantly, 20 alkylated DNA only 10× less efficiently than (+)-duocarmycin SA being far more effective than the ring closed iso-CI-TMI might be projected to be. To date, this observation is unique to the iso-CI series and, as yet, has not been observed in the iso-CBI series or with other analogs incorporating modified alkylation subunits. Whether this stems from the use of the mesylate versus chloro seco precursor for 20 or is unique to the iso-CI series remains to be established. However, it does suggest that in selected instances the seco precursors may exhibit productive properties that exceed those of the corresponding cyclopropane ring-closed materials especially with the more reactive agents. Unlike the more stable agents which readily undergo cyclopropane ring closure, the ring closure of 20 to iso-CI-TIM under the conditions of the assay is unlikely. Rather, the DNA alkylation most likely occurs directly with 20 without the intermediate generation of the free cyclopropane agent. Thus, not only did the relocation of the C-4 carbonyl not alter the DNA alkylation selectivity, but its removal altogether may be possible providing a class of agents which, depending on the nature of the electrophile, also exhibit comparable DNA alkylation selectivities, efficiencies, and rates. This is consistent with early observations that related electrophiles that lack the capabilities for ring closure to an activated cyclopropane exhibit DNA alkylation selectivities identical to the corresponding natural products.

TABLE 3

Calf Thymus DNA Alkylation

| conditions | base-pair equiv | 66 | 65 | 44 | solvolysis |
|---|---|---|---|---|---|
| 4° C., 72 h | 75[a] | 94% | <5% | nd | nd |
| 4° C., 72 h | 150[a] | 95% | <5% | nd | nd |
| 4° C., 72 h | 150[b] | 92% | <5% | nd | nd |
| 4° C., 120 h | 150[b] | 95% | <5% | nd | nd |

[a]Analytical scale, HPLC separation and UV quantitation.
[b]Preparative scale, isolation and weight quantitation.
[c]nd = not detected.

Quantitation, Isolation, and Characterization of the (−)-iso-CBI-TMI

Adenine Adduct: The initial alkylation studies established that (−)-iso-CBI-TMI alkylated adenine within the minor groove in a manner identical to (+)-duocarmycin SA. The thermal cleavage of DNA used to identify the alkylation sites in these studies only detects adducts susceptible to thermal glycosidic bond cleavage (adenine N3, guanine N3, or guanine N7 alkylation), and potential alkylation events involving other nucleophilic centers in DNA may not be detected in this assay. In order to confirm that (−)-iso-CBI- TMI alkylates DNA in a manner identical to (+)-duocarmycin SA and in efforts that established the relative extent of adenine N3 versus alternative alkylation events, the quantitation of the adenine N3 alkylation reaction and confirmation of the structure of the product of the reaction were established through isolation and characterization of the thermally released adenine adduct.

This was addressed through a study of the alkylation of calf thymus DNA. Optimized conditions for the alkylation were established for (−)-44 on an analytical scale (100 μg of agent). For this purpose, the long-wavelength UV absorption of the agent and the adduct provided a useful quantitative measure of the adenine adduct, unreacted starting material and any side products (solvolysis or rearrangement), Table 3. Analytical HPLC analysis was used to confirm the identity of the products through correlation of retention times and UV spectral data with authentic materials. The preparative DNA alkylation reaction and subsequent isolation of (+)-66 was carried out under conditions determined to provide complete consumption of the agent in the presence of a large excess of DNA. Thus, extraction (EtOAc) of the aqueous buffer solution containing calf thymus DNA following alkylation (4° C., 72 h, 150 bp) afforded no recovered (−)-44, and only a small amount (<5%) of the rearranged product 65. Conducting the reaction at 4° C. in the presence of a large excess of DNA precluded competitive solvolysis. Thermal treatment of the alkylated DNA in aqueous 10 mM sodium phosphate buffer (100° C., 30 min, pH 7.0) followed by EtOAc extraction provided 66 in 90–95% conversion, ≧95% purity (by HPLC). Repeating this thermal treatment provided little or no additional adduct. No trace of a competing guanine adduct could be detected. This high conversion to a single adduct established that 44 participates exclusively in the adenine N3 alkylation reaction under the conditions examined.

Figure 10:
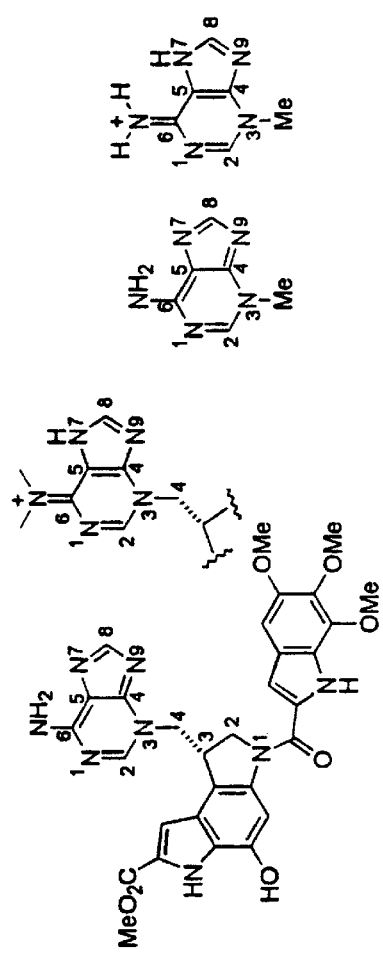
FIG. 10 provides ¹H and ¹³C NMR data of various adenine adducts.
Figure 10:
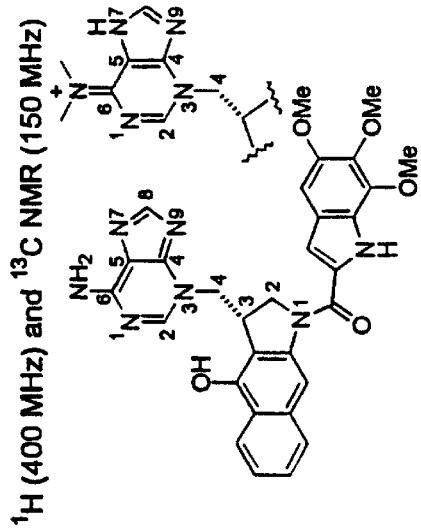

Full characterization of 66 unambiguously established its structure and the spectral characteristics showed strong homology to the duocarmycin SA[11] and A adenine N3 adducts and N3 methyl adenine (FIG. 10). In the $^1$H NMR, the C3—H of adduct 66 was observed as a single proton (1H) at a characteristic chemical shift of 4.36–4.37. The C3—H NMR signal for the benzylic center resulting from alternative adenine N3 addition to the more substituted cyclopropane carbon would be readily distinguishable appearing as two protons (3.5–3.6 ppm, 2H) with a large geminal coupling constant (19.5 Hz). Additionally diagnostic of the structure were the chemical shifts and coupling constants for C2—$H_2$ and C4—$H_2$. Characteristic of an adenine N3 alkylation product, the adenine C2—H and C8—H were readily distinguishable. The $^1$H NMR of the protonated base was taken in DMSO/1% TFA and again a strong correlation to the spectral data obtained for the duocarmycin SA adduct was observed. The two adenine C6—$NH_2$ protons were seen as separate signals indicating restricted rotation about the $^6$C=$NH_2^+$ bond as is present in protonated N-methyl adenine. In addition, a downfield shift as a result of protonation of both the adenine C8—H and adenine C2—H was also observed. The $^{13}$C NMR of 66 was also found to be in excellent agreement with that of the duocarmycin SA and A adducts. (Boger, D. L., et al., *J. Am. Chem. Soc.* 1991, 113, 6645.) The key distinguishing signals are found within or proximal to the fused five- versus six-membered ring with 66 exhibiting chemical shifts consistent only with the former, i.e. C3 at δ39.7 consistent with duocarmycin SA (δ41.1) and inconsistent with the six-membered ring in duocarmycin $B_1/C_1$ (δ33–34). Thus, the adenine N3 addition to the least substituted cyclopropane carbon of (−)-iso-CBI-TMI, as with (+)-duocarmycin SA, was found to account for 90–100% of the consumption of the agent in the presence of duplex DNA and confirmed that it binds and alkylates DNA in a manner identical to the natural products despite the relocation of the C-4 carbonyl.

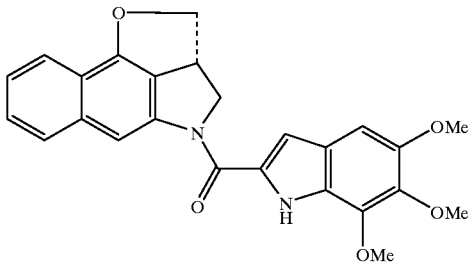

65

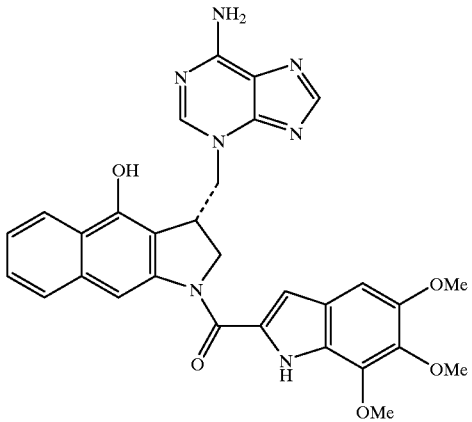

66

In Vitro Cytotoxic Activity: Past studies with agents in this class have defined a direct correlation between solvolysis stability and cytotoxic potency. Consistent with their relative reactivity, the iso-CBI based agents exhibited cytotoxic activity that closely followed this relationship in spite of the deep-seated structural modification (Table 5, FIG. 8). The results, which also follow trends established in the DNA alkylation studies, demonstrate that the (−)-enantiomer of the analogs possessing the (S)-configuration analogous to the natural products, is the more potent enantiomer by 10–50×. The exception to this generalization is N-BOC-iso-CBI where the two enantiomers were not readily distinguishable and the unnatural enantiomer was consistently slightly more potent (1–2×). The seco precursors, which lack the preformed cyclopropane but possess the capabilities of ring closure, were found to possess cytotoxic activity that was indistinguishable from the final ring-closed agents. Consistent with the unique importance of the C5 methoxy group of the duocarmycins, iso-CBI-TMI (44) and 46 were found to be equipotent illustrating that the C6 and C7 methoxy groups of 44 are not contributing to its cytotoxic potency. The cinnamate derivative 48 was found to be substantially less potent (40–50×) suggestive of the requirement for a rigid $N^2$ DNA binding subunit. Finally, the agents exhibited a smooth trend of increasing cytotoxic potency as the size and length of the DNA binding subunits increased with iso-CBI-$CDPI_1$ and iso-CBI-$CDPI_2$ displaying the most potent cytotoxic activity in the series exhibiting $IC_{50}$ values of 200 and 50 pM, respectively. (While we were unable to isolate N-BOC-iso-CI (21) and iso-CI-TMI for direct comparison, their seco precursors (±)-19 and (±)-20 exhibited surprisingly potent cytotoxic activity ($IC_{50}$, L1210=10 μM and 6 nM, respectively) that likely exceeds that of the ring closed materials themselves.)

Findings: iso-CI and iso-CBI were designed to test a key element of the different proposals for the origin of the DNA alkylation sequence with the duocarmycins and CC-1065. These agents were prepared by application of a directed ortho metallation and ortho spirocyclization in an improved synthetic scheme complementary to that reported for CI and CBI. Iso-CBI was found to be 5× less stable than CBI and possess a reactivity comparable with CC-1065 and duocarmycin A. In addition, nucleophilic addition occurred at the least substituted cyclopropane carbon with a regioselectivity (40:1 ) comparable to that of CBI but which exceeds that of the natural products themselves (6–1.5:1). Comparison of the X-ray structures of iso-CBI and CBI revealed the near identical non-ideal conjugation of the cyclopropanes and the exclusive stereoelectronic alignment of the cleaved cyclopropane bond. Consistent with recent observations, the lower stability of iso-CBI relative to CBI itself can be attributed to a diminished cross-conjugated vinylogous amide stabilization for which the $N^2$—$C^{2a}$ bond length is diagnostic.[7,42] Resolution and incorporation of iso-CBI into a full set of duocarmycin and CC-1065 analogs allowed for comparison of their properties and a further distinguishing test for the origin of the DNA alkylation sequence selectivity. The iso-CBI analogs were highly potent cytotoxic agents exhibiting picomolar $IC_{50}$'s which correlated with their relative stability. In addition to smoothly following this correlation, the analogs displayed a smooth trend of increasing cytotoxic potency with the increasing length in the DNA binding subunit. Analogous to the natural products, the (S)-enantiomer possessing the absolute configuration of 1–3, proved to be more potent (10–50×) than the (R)-enantiomer. DNA alkylation studies revealed a strong correlation between DNA alkylation efficiency and cytotoxic potency as (–)-iso-CBI-TMI was approximately 50–100×less efficient than (+)-CBI-TMI and (+)-duocarmycin SA. In addition, both the iso-CI and iso-CBI analogs, with the repositioned C-4 carbonyl, exhibited the identical sequence selectivity and alkylated the same sites as CBI-TMI and duocarmycin SA derived from adenine N3 addition to the least substituted cyclopropane carbon at comparable reaction rates. This is inconsistent with a proposal that the DNA alkylation selectivity is controlled by a sequence-dependent DNA backbone phosphate protonation of the C-4 carbonyl for activation of alkylation but is consistent with the noncovalent binding and steric accessibility model. Finally, this set of isomeric analogs contains the most significant structural modification to the alkylation subunit to date, yet remain effective DNA alkylating agents with properties comparable to the natural products themselves.

Synthesis of Materials 1-(tert-Butyloxycarbonyl)-4-hydroxy-3 [[(methanesulfonyl)oxy]methyl]-2,3-dihydroindole (19)

A solution of 18 (22 mg, 0.057 mmol) in 2 mL of 1:1 i-PrOH/THF was treated with 12 N HCl (33 μL, 0.4 mmol) and stirred for 48 h at 25° C. The reaction solution was concentrated under reduced pressure. Flash chromatography ($SiO_2$, 1.5×10 cm, 40% EtOAc/hexane) afforded recovered 18 (8 mg, 41%) and 19 (9.5 mg, 48%) as a white film: $^1$H NMR ($CDCl_3$, 400 MHz) δ7.43 (m, 1H), 7.07 (m, 1H), 6.39 (d, J=8.6 Hz, 1H), 5.44 (br s, 1H), 4.55 (dd, J=4.5, 9.8 Hz, 1H), 4.26 (dd, J=8.1, 9.8 Hz, 1H), 4.00 (m, 2H), 3.79 (m, 1H); IR (film) $v_{max}$ 3347, 2977, 1682, 1622, 1602, 1467, 1394, 1172, 1145, 948 $cm^{-1}$; FABHRMS (NBA/CsI) m/z 476.0156 ($C_{15}H_{21}NO_6S+Cs^+$ requires 476.0144).

4-Hydroxy-3[[(methanesulfonyl)oxy]methyl]-1-[5,6, 7-trimethoxyindol-2-yl)carbonyl]-2,3-dihydroindole (20)

A sample of 18 (9.0 mg, 0.023 mmol) was dissolved in 3.6 N HCl/EtOAc (2.4 mL) and the solution was stirred for 30 min at 25° C. The solvents were removed by a stream of $N_2$ and the residual salt was thoroughly dried under high vacuum. The salt was dissolved in anhydrous DMF (1.2 mL) and treated with 37 (7 mg, 0.028 mmol) and EDCI (13 mg, 0.07 mmol). The resulting solution was stirred at 25° C. for 3 h under Ar. The reaction mixture was then diluted with $H_2O$ (5 mL), and extracted with EtOAc (3×5 mL). The combined organic layer was dried ($Na_2SO_4$), and concentrated under reduced pressure. Flash chromatography ($SiO_2$, 1.5×10 cm, 50% EtOAc/hexane) yielded pure 20 (6.0 mg, 55%) as a white film: $^1$H NMR ($CDCl_3$, 400 MHz) δ9.33 (br s, 1H), 7.87 (d, J=8.0 Hz, 1H), 7.19 (m, 1H), 6.92 (d, J=2.4 Hz, 1H), 6.84 (s, 1H), 6.52 (dd, J=0.5, 8.0 Hz, 1H), 4.65 (dd, J=4.3, 10.1 Hz, 1H), 4.58 (dd, J=9.2, 10.8 Hz, 1H), 4.51 (dd, J=3.9, 10.8 Hz, 1H), 4.31 (dd, J=8.4, 10.1 Hz, 1H), 4.05 (s, 3H), 4.01 (m, 1H), 3.92 (s, 3H), 3.89 (s, 3H), 2.95 (s, 3H); IR (film) $v_{max}$ 3261, 2938, 1659, 1611, 1462, 1352, 1306, 1282, 1174, 1107 $cm^{-1}$; FABHRMS (NBA/CsI) m/z 609.0319 ($C_{22}H_{24}N_2O_8S+Cs^+$ requires 609.0308).

N-(tert-Butyloxycarbonyl)-4-(methoxymethoxy)-2-naphthylamine (23)

A solution of 22[22] (6.67 g, 25.0 mmol) in 125 mL of anhydrous DMF at 0° C. was treated with NaH (1.13 g, 28.0 mmol) in several portions over 5 min. After 10 min, $Bu_4NI$ (0.925 g, 2.5 mmol) was added followed by the dropwise addition of $ClCH_2OCH_3$ (2.9 mL, 38 mmol). The reaction mixture was stirred at 25° C. for 5 h before the reaction was quenched by the slow addition of 100 mL of $H_2O$. The aqueous layer was extracted with EtOAc (3×100 mL). The organic layers were combined, washed with 10% aqueous $NaHCO_3$ (100 mL), $H_2O$ (4×50 mL), dried ($Na_2SO_4$), and concentrated under reduced pressure. Flash chromatography ($SiO_2$, 4×15 cm, 0–15% EtOAc/hexane gradient) provided 23 (6.0 g, 78%) as a peach colored solid: mp 64–66° C.; $^1$H NMR ($CDCl_3$, 250 MHz) δ8.15 (d, J=7.8 Hz, 1H), 7.67 (m, 2H), 7.38 (m, 2H), 7.05 (d, J=1.9 Hz, 1H), 6.87 (br s, 1H), 5.34 (s, 2H), 3.51 (s, 3H), 1.54 (s, 9H); $^{13}$C NMR ($CDCl_3$, 100 MHz) δ153.3, 152.8, 136.0, 134.8, 127.0, 126.9, 123.7, 122.5, 121.6, 108.0, 101.8, 94.6, 80.5, 56.1, 28.2; IR (film) $v_{max}$ 3334, 2977, 1713, 1634, 1538, 1392, 1367, 1248, 1160, 1057 $cm^{-1}$; FABHRMS (NBA) m/z 303.1463 ($C_{17}H_{21}NO_4$ requires 303.1471).

Anal. Calcd for $C_{17}H_{21}NO_4$: C, 67.31; H, 6.98; N, 4.62. Found: C, 67.13; H, 7.18; N, 4.89.

N-(tert-Butyloxycarbonyl)-3-iodo-4-(methoxymethoxy)-2-naphthylamine (24)

A solution of 23 (0.435 g, 1.43 mmol) in 5.7 mL anhydrous THF was cooled to −25° C. and treated with TMEDA (0.758 mL, 5.0 mmol) followed by n-BuLi (2.29 mL of a 2.5 M solution in hexane, 5.0 mmol) in a slow dropwise manner. The resulting gold solution was stirred for 2 h at −25° C. The reaction mixture was treated with 1-chloro-2-iodoethane (0.37 mL, 5.0 mmol) and stirred for 15 min at 25° C. The reaction was diluted with $H_2O$ (40 mL), extracted with $Et_2O$ (3×20 mL), and the combined organic extracts were washed with saturated aqueous NaCl, dried ($Na_2SO_4$) and concentrated under reduced pressure. Flash chromatography ($SiO_2$, 2.5×15 cm, 0–7% EtOAc/hexane gradient) yielded 24 (490 mg, 80%) as a yellow oil: $^1$H NMR ($CDCl_3$, 400 MHz)

δ8.35 (s, 1H), 8.03 (d, J=12.8 Hz, 1H), 7.78 (d, J=12.5 Hz, 1H), 7.42 (m, 2H), 7.14 (br s, 1H), 5.20 (s, 2H), 3.74 (s, 3H), 1.56 (s, 9H); $^{13}$C NMR (CDCl$_3$, 100 MHz) δ154.7, 152.6, 135.1, 134.8, 127.6, 127.4, 125.1, 125.0, 122.2, 113.0, 100.5, 87.7, 81.1, 58.5, 28.4; IR (film) $v_{max}$ 3391, 2977, 2933, 1732, 1524, 1367, 1340, 1276, 1228, 1157 cm$^{-1}$; FABHRMS (NBA/NaI) m/z 430.0507 (C$_{17}$H$_{20}$INO$_4$+H$^+$ requires 430.0515).

2-[[N-(tert-Butyloxycarbonyl)-N-(2-propen-1-yl) amino]-3-iodo-4-(methoxymethoxy)naphthalene (25)

A solution of 24 (0.490 g, 1.1 mmol) in 36 mL anhydrous DMF was cooled to −10° C., and treated with NaH (69 mg, 1.7 mmol) in small portions. The resulting suspension was stirred 15 min and treated with neat allyl bromide (0.49 mL, 5.7 mmol) in a slow dropwise manner. The reaction mixture was warmed to 25° C. and stirred for 1 h. The reaction mixture was quenched with the addition of 5% aqueous NaHCO$_3$ (50 mL), and the aqueous layer was extracted with EtOAc (3×20 mL). The combined organic extracts were washed with H$_2$O (5×10 mL) dried (Na$_2$SO$_4$), and condensed under reduced pressure to yield 25 as a 2:1 mixture of amide rotamers as a yellow oil. Flash chromatography (SiO$_2$, 2.5×15 cm, 10% EtOAc/hexane) yielded 25 (503 mg, 94%) as a colorless oil: $^1$H NMR (CDCl$_3$, 250 MHz) δ8.16 (m, 1H), 7.77 (m, 1H), 7.50 (m, 3H), 5.97 (m, 1H), 5.23 (m, 2H), 5.07 (m, 2H), 4.56 (m, 1H), 3.80 (m, 1H), 3.72 (s, 3H), 1.55 and 1.33 (s, 9H); $^{13}$C NMR (CDCl$_3$, 100 Mz) δ155.6 and 155.4, 154.1 and 153.9, 141.3 and 141.1, 133.8 and 133.5, 127.7 and 127.6, 127.1, 126.8, 125.2, 124.5, 122.4, 117.8 and 117.3, 100.6, 95.7, 80.6 and 80.3, 58.3, 53.6, 52.4, 28.3 and 28.2; IR (film) $v_{max}$ 2975, 2930, 1703, 1581, 1566, 1385, 1366, 1159, 1047 cm$^{-1}$; FABHRMS (NBA/CsI) m/z 601.9825 (C$_{20}$H$_{24}$INO$_4$+CS$^+$ requires 601.9804).

1-(tert-Butyloxycarbonyl)-4-(methoxymethoxy)-3-[[(2',2',6',6'-tetramethyl-piperidino)oxy]methyl]-2,3-dihydro-1H-benzo[f]indole (26)

A solution of 25 (470 mg, 1.00 mmol) and TEMPO (468 mg, 3.0 mmol) in 43 mL anhydrous benzene was treated with Bu$_3$SnH (0.283 mL, 1.05 mmol). The solution was warmed at 50° C. and an additional 1.05 equiv of Bu$_3$SnH (0.283 mL, 1.05 mmol) was added twice during the next 30 min. Another 3.0 equiv of TEMPO (468 mg, 3.0 mmol) was added in 10 mL anhydrous benzene, along with an additional 1.05 equiv of Bu$_3$SnH added twice during the next 45 min. After 1.5 h total, the solution was cooled to 25° C., and the volatiles were removed under reduced pressure. Flash chromatography (SiO$_2$, 2.5×15 cm, 0–12% EtOAc/hexane gradient) provided 26 (470 mg, 94%) as a yellow oil: $^1$H NMR (CDCl$_3$, 250 MHz) δ8.05 (br s, 1H), 7.97 (d, J=8.0 Hz, 1H), 7.74 (d, J=7.7 Hz, 1H), 7.36 (m, 2H), 5.24 (d, J=5.9 Hz, 1H), 5.16 (d, J=5.9 Hz, 1H), 4.26 (m, 1H), 4.15 (m, 1H), 4.01 (m, 1H), 3.81 (m, 2H), 3.63 (s, 3H), 1.61 (s, 9H), 1.23 (s, 3H), 1.17 (s, 3H), 1.04 (s, 3H), 1.04 (s, 3H), 0.99 (s, 3H), 1.48–0.89 (m, 6H); $^{13}$C NMR (CDCl$_3$, 62.5 MHz) δ152.0, 149.3, 141.1, 135.3, 127.2, 125.7, 124.4, 123.4, 122.6, 121.0, 107.0, 99.1, 80.2, 76.0, 59.3, 57.1, 51.2, 39.1, 32.6, 27.9, 19.6, 16.6; IR (film) $v_{max}$ 2974, 2931, 1709, 1634, 1446, 1374, 1352, 1332, 1147cm$^{-1}$; FABHRMS (NBA/CsI) m/z 631.2168 (C$_{29}$H$_{42}$N$_2$O$_5$+Cs$^+$ requires 631.2148).

1-(tert-Butyloxycarbonyl)-3-(hydroxymethyl)-4-(methoxymethoxy)-2,3-dihydro-1H-benzo[f]indole (27)

A solution of 26 (220 mg, 0.44 mmol) in 15 mL 3:1:1 HOAc/H$_2$O/THF was treated with Zn powder (1.15 g, 17.6 mmol) and the resulting suspension was warmed at 70° C. under a reflux condenser and with vigorous stirring for 1 h. The reaction mixture was cooled to 25° C., and the Zn was removed by filtration through Celite with a 25 mL CH$_2$Cl$_2$ wash. The volatiles were removed under reduced pressure, and the resulting residue was dissolved in 25 mL of EtOAc and filtered. The solution was concentrated under reduced pressure. Flash chromatography (SiO$_2$, 2.5×10 cm, 30–40% EtOAc/hexane gradient) provided 27 (138 mg, 87%) as a colorless oil: $^1$H NMR (CDCl$_3$, 250 MHz) δ8.05 (br s, 1H), 7.91 (d, J=8.0 Hz, 1H), 7.72 (d, J=7.5 Hz, 1H), 7.36 (m, 2H), 5.23 (d, J=6.0 Hz, 1H), 5.16 (d, J=6.0 Hz, 1H), 4.10 (m, 1H), 3.94–3.78 (m, 4H), 3.63 (s, 3H), 2.04 (d, J=8.4 Hz, 1H), 1.58 (s, 9H); $^{13}$C NMR (CDCl$_3$, 125 MHz) δ152.5, 149.7, 142.0, 136.0, 127.9, 126.4, 124.6, 124.1, 123.1, 121.3, 107.8, 100.0, 81.1, 65.1, 57.8, 51.3, 40.7, 28.3; IR (film) $v_{max}$ 3447, 2975, 1704, 1634, 1447, 1353, 1336, 1149 cm$^{-1}$; FABHRMS (NBA) m/z 360.1821 (C$_{20}$H$_{25}$NO$_5$+H$^+$ requires 360.1811).

1-(tert-Butyloxycarbonyl)-3-chloromethyl-4-(methoxymethoxy)-2,3-dihydro-1H-benzo[f]indole (28)

From 27: A solution of 27 (55 mg, 0.16 mmol) in 3 mL anhydrous CH$_2$Cl$_2$ was treated with CCl$_4$ (155 μL, 1.6 mmol) and Ph$_3$P (212 mg, 0.81 mmol) and the mixture was stirred at 25° C. for 2 h. The solution was concentrated in vacuo. Flash chromatography (SiO$_2$, 1.5×15 cm, 0–12% EtOAc/hexane gradient) provided 28 (52 mg, 90%) as a white solid: mp 99–101° C.; $^1$H NMR (CDCl$_3$, 250 MHz) δ8.03 (br s, 1H), 7.89 (d, J=8.1 Hz, 1H), 7.72 (d, J=7.6 Hz, 1H), 7.37 (m, 2H), 5.24 (d, J=6.1 Hz, 1H), 5.15 (d, J=6.1 Hz, 1H), 4.06 (m, 4H), 3.65 (s, 3H), 3.51 (app t, J=10.1 Hz, 1H), 1.59 (s, 9H); $^{13}$C NMR (CDCl$_3$, 100 MHz) δ152.3, 150.5, 141.1, 136.2, 127.9, 126.6, 124.6, 124.1, 122.4, 121.4, 107.7, 100.0, 81.2, 57.5, 52.1, 45.9, 40.8, 28.4; IR (film) $v_{max}$ 2976, 1704, 1634, 1449, 1336, 1147, 1055, 983 cm$^{-1}$; FABHRMS (NBA) m/z 378.1463 (C$_{20}$H$_{24}$ClNO$_4$+H$^+$ requires 378.1472).

Anal. Calcd for C$_{20}$H$_{24}$INO$_4$: C, 63.75; H, 6.40; N, 3.71. Found: C, 63.42; H, 6.11; N, 3.41.

From 29: A solution of 29 (500 mg, 1.0 mmol) in 10 mL anhydrous benzene was treated with AIBN (15.7 mg, 0.1 mmol) and Bu$_3$SnH (295 μL, 1.1 mmol) and warmed at 80° C. for 2 h. The reaction mixture was concentrated under reduced pressure and flash chromatography (SiO$_2$, 2.5×15 cm, 0–20% EtOAc/hexanes gradient) yielded 28 (360 mg, 96%) as a white solid identical to that described above.

Resolution of (28). A sample of 28 (4.0 mg) in 0.9 mL of 5% i-PrOH/hexane was resolved on a semipreparative Daicel Chiralcel OD column (10 μm, 2×25 cm, 7.0 mL/min flow rate, 3% i-PrOH/hexane). The effluent was monitored at 254 nm and the enantiomers eluted with retention times of 29.0 and 35.8 min (α=1.25). The first enantiomer (S) was found to be >99% enantiomerically pure. The second fraction (R) was reinjected in order to obtain a sample of >99% ee. The fractions containing the separated enantiomers were collected and concentrated to afford (+) and (−)-28.(+)-(3S)-28: [α]$_D^{25}$ +29(c 0.50,CH$_2$Cl$_2$); (−)-(3R)-28:[α]$_D^{25}$ −30 (c0.5,CH$_2$Cl$_2$).

2-[[N-(tert-Butyloxycarbonyl)-N-(3-chloro-2-propen-1-yl)]amino-3-iodo-4-(methoxymethoxy) naphthalene (29)

A solution of 24 (0.480 g, 1.1 mmol) in 11 mL anhydrous DMF was cooled to 0° C., and treated with NaH (67 mg, 2.2 mmol) in small portions. The resulting suspension was stirred 15 min and treated with neat 1,3-dichloropropene (0.52 mL, 5.5 mmol) in a slow dropwise manner, followed by catalytic Bu$_4$NI (40 mg, 0.1 mmol). The reaction mixture was warmed to 25° C. and stirred for 12 h. The reaction mixture was quenched with the addition of 5% aqueous NaHCO$_3$ (50 mL), and the aqueous layer was extracted with EtOAc (3×20 mL). The combined organic extracts were washed with H$_2$O(5×10 mL), dried (Na$_2$SO$_4$), and concentrated under reduced pressure to yield 29 as a mixture of rotamers and E and Z alkenes as a yellow oil. Flash chromatography (SiO$_2$, 2.5×15 cm, 0–20% EtOAc/hexanes gradient) yielded 29 (540 mg, 96%) as a yellow oil: $^1$H NMR (CDCl$_3$, 250 MHz) δ8.16 (m, 1H), 7.80 (m, 1H), 7.55 (m, 2H), 7.44 (s, 1H), 6.11 (m, 2H), 5.25 (d, J=5.6 Hz, 1H), 5.20 (d, J=5.6 Hz, 1H), 4.51 (m, 1H), 3.75 (m, 1H), 3.73 (s, 3H), 1.55 and 1.31 (s, 9H); $^{13}$C NMR (CDCl$_3$, 62.5 MHz) δ156.2, 153.9, 140.7, 134.0, 128.7, 127.9, 127.7, 127.4, 127.1, 124.7, 122.5, 121.7, 100.7, 80.8, 77.2, 58.5, 49.5, 28.2; IR (film) $v_{max}$ 2975, 1699, 1565, 1387, 1366, 1328, 1294, 1254, 1162 cm$^{-1}$; FABHRMS (NBA/NaI) m/z 504.0424 (C$_{20}$H$_{23}$ClINO$_4$+H$^+$requires 504.0439).

1-(tert-Butyloxycarbonyl)-3-chloromethyl-4-hydroxy-2,3-dihydro-1H-benzo[f]indole (30)

A solution of 28 (18 mg, 47.5 μmol) in 1.5 mL of 1:1 i-PrOH/THF was treated with 12 N HCl (0.20 mL, 0.38 mmol) and the mixture was stirred at 25° C. for 6 h before the volatiles were removed in vacuo. Flash chromatography (SiO$_2$, 1.5×15 cm, 0–20% EtOAc/hexane gradient) provided 30 (14.5 mg, 90%) as a pale yellow oil: $^1$H NMR (CDCl$_3$, 250 MHz) δ7.85 (d, J=8.0 Hz, 1H), 7.71 (d, J=7.8 Hz, 1H), 7.43–7.30 (m, 2H), 5.67 (s, 1H), 4.09–3.86 (m, 4H), 3.65 (dd, J=8.0, 10.0 Hz, 1H), 1.59 (s, 9H);$^{13}$C NMR (CDCl$_3$, 6.25 MHz) δ147.9, 135.8, 132.7, 128.8, 128.0, 126.6, 123.7, 121.2, 119.5, 119.5, 104.4, 77.2, 52.6, 46.4, 34.7, 28.5; IR (film) $v_{max}$3368, 2976, 1668, 1477, 1450, 1369, 1145, 978, 746 cm$^{-1}$; FABHRMS (NBA/CsI) m/z 466.0197 (C$_{18}$H$_{20}$ClNO$_3$+Cs$^+$requires 466.0186). (−)-(3S)-30: [α]$_D^{25}$ −54 (c 0.25, CH$_3$OH); (+)-(3R)-30: [α]$_D^{25}$+51 (c 0.30, CH$_3$OH).

2-(tert-Butyloxycarbonyl)-1,2,9,9a-tetrahydrocyclopropa[c]benzo [f]indol-8-one (N-BOC-iso-CBI, 31)

A solution of 30 (5.0 mg, 0.015 mmol) in 0.6 mL CH$_3$CN was treated with DBU (2.7 μL, 0.018 mmol) and the mixture was stirred at 25° C. for 15 min. Flash chromatography (SiO$_2$, 1.5×10 cm, 10% EtOAc/hexane) afforded 31 (4.3 mg, 96%) as a light golden oil: $^1$H NMR (CDCl$_3$, 400 MHz) δ7.98 (d, J=7.8 Hz, 1H), 7.50 (dt, J=1.4, 7.8 Hz, 1H), 7.28 (d, J=7.8 Hz, 1H), 7.21 (dt, J=1.1, 7.8 Hz, 1H), 6.97 (br s, 1H), 3.88 (br d, J=11.2 Hz, 1H), 3.81 (dd, J =4.9, 11.1 Hz, 1H), 2.88 (dt, J=5.5, 7.8 Hz, 1H), 1.87 (dd, J=3.2, 7.8 Hz, 1H), 1.53 (s, 9H), 1.41 (dd, J=3.2, 5.5 Hz, 1H); $^1$H NMR (C$_6$D$_6$, 400 MHz) δ8.34 (dd, J=0.6, 7.8 Hz, 1H), 7.10 (m, 2H), 6.92 (m, 1H), 3.18 (br m, 1H), 2.32 (m,1H), 1.49 (dd, J=3.1, 7.8 Hz, 1H), 1.39 (s, 9H), 0.66 (dd, J=3.1, 5.4 Hz, 1H);$^{13}$C NMR (CDCl$_3$, 62.5 MHz) δ194.7, 154.3, 142.0, 134.3, 127.7, 127.3, 125.9, 125.2, 103.2, 77.2, 51.5, 46.1, 32.0, 28.2, 25.7; IR (film) $v_{max}$2973, 2927, 1716, 1670, 1635, 1472, 1410, 1324, 1143, 1009 cm$^{-1}$; UV (THF) λ$_{max}$(ε) 387 (2700), 302 (6000 sh), 293 (6900), 250 (20400) nm; FABHRMS (NBA/NaI) m/z 298.1450 (C$_{18}$H$_{19}$NO$_3$+H$^+$requires 298.1443).(−)-(8aS, 9aS)-31: [α]$_D^{25}$−172 (c0.08,CH$_3$OH); (+)-(8aR,9aR)-31: [α]$_D^{25}$+179 (c 0.12, CH$_3$OH).

3-Chloro-4-hydroxy- 1-(methoxycarbonyl)-2,3-dihydro-1H-benzo[f]indole (32)

A solution of 28 (11 mg, 29.1 μmol) was treated with 1.0 mL of 3.6 N HCl/EtOAc and the resulting solution was stirred for 30 min at 25° C. The solvent was removed by a stream of N$_2$ and the residual salt was dried under vacuum. This salt was suspended in 0.6 mL of anhydrous THF and treated with NaHCO$_3$ (5.4 mg, 64.1 μmol, 2.2 equiv) and ClCO$_2$CH$_3$ (4.5 μL, 58.2 μmol, 2.0 equiv) and the mixture was stirred for 3 h at 25° C. Upon completion, the reaction mixture was diluted with 10 mL of H$_2$O extracted with EtOAc (3×10 mL), dried (Na$_2$SO$_4$) and concentrated in vacuo. Flash chromatography (SiO$_2$, 1.5×15 cm, 0–40% EtOAc/hexane gradient) provided pure 32 (5.5 mg, 65%) as a white solid: $^1$H NMR (CDCl$_3$, 400 MHz ) δ7.86 (d, J=8.2 Hz, 1H), 7.86 (br s, 1H), 7.73 (d, J=8.0 Hz, 1H), 7.42 (m, 1H), 7.35 (m, 1H), 5.80 (s, 1H), 4.11 (m, 2H), 4.01–3.87 (m, 5H), 3.63 (app t, J=9.4 Hz, 1H); IR (film) $v_{max}$3379, 2956, 1673, 1435, 1372, 1283, 1218 cm$^{-1}$; FABHRMS (NBA/NaI) m/z 291.0656 (M$^+$, C$_{15}$H$_{14}$ClNO$_3$ requires 291.0662).

The structure and absolute configuration of (3R)-32 derived from the slower eluting enantiomer of 28 (t$_R$=35.8 min, [α]$_D^{25}$−9 (c 0.10, CH$_3$OH)) was obtained from a single-crystal X-ray structure determination conducted on prisms grown from EtOAc/hexane.

2-(Methoxycarbonyl)-1,2,9,9a-tetrahydrocyclopropa[c]benzo[f]indol-8-one (N-CO$_2$Me-iso-CBI, 33)

A solution of 32 (5.0 mg, 0.017 mmol) in 0.5 mL of CH$_3$CN was treated with DBU (3.9 μL, 0.025 mmol) and the mixture was stirred at 25° C. for 15 min. Flash chromatography (SiO$_2$, 1.5×10 cm, 0–40% EtOAc/hexane gradient) afforded 33 (4.0 mg, 91%) as a pale yellow solid: $^1$H NMR (C$_6$D$_6$, 400 MHz) δ8.33 (d, J=6.0 Hz, 1H), 7.40 (br s, 1H)7.10 (app t, J=6.0 Hz, 1H), 7.03 (d, J=6.0 Hz1H), 6.91 (m, 1H), 3.36 (s, 3H), 3.17 (m, 1H), 2.93 (m, 1H), 2.30 (dt, J=4.0, 6.0 Hz, 1H), 1.49 (dd, J=2.4, 6.4 Hz, 1H), 0.64 (dd, J=2.8, 4.4 Hz, 1H); IR (film)$v_{max}$2954, 1731, 1633, 1445, 1323, 1196, 1018cm$^{-1}$; UV (THF) λ$_{max}$(ε)(386 (2300), 302 (4500 sh), 293 (5100), 250 (18000) nm; FABHRMS (NBA/NaI) m/z 255.0901 (M$^+$, C$_{15}$H$_{13}$NO$_3$ requires 255.0895). (+)-(8aR,9aR)-33: [α]$_D^{25}$+31 (c 0.07, CH$_3$OH).

The structure of 33 was confirmed with a single-crystal X-ray structure determination conducted on plates grown from EtOAc/hexane.[37]

1,2,9,9a-Tetrahydrocyclopropa[c]benzo [f]indol-8-one (iso-CBI, 34)

A solution of 28 (10.6 mg, 28.1 μmol) was treated with 3.6 M HCl/EtOAc and the mixture was stirred at 25° C. for 30 min. The volatiles were removed by a stream of N$_2$ and the residual salt was suspended in 1.0 mL of degassed CH$_3$CN. The suspension was treated with DBU (9.3 μL, 61.8 μmol, 2.2 equiv) and stirred under Ar for 20 min at 25° C. in the dark. Flash chromatography (SiO$_2$, 1.5×15 cm, 40% EtOAc/ hexane) provided pure 34 (3.0 mg, 55%) as an unstable bright yellow oil: $^1$H NMR (C$_6$D$_6$, 400 MHz) δ8.38 (d, J=8.0 Hz, 1H), 7.18 (m, 1H), 6.99 (d, J=8.0 Hz, 1H), 6.87 (m, 1H), 5.27 (s, 1H), 2.60 (m, 1H), 2.52 (m, 1H), 2.45 (m, 1H), 1.70 (m, 1H), 1.00 (m, 1H); IR (film) $v_{max}$ 3358, 1682, 1594, 1470, 1284, 1262, 1223 cm$^{-1}$; FABHRMS (NBA/NaI) m/z 198.0926 (C$_{13}$H$_{11}$NO+H$^+$requires 198.0919).

9,9a-1H-Dihydrocyclopropa[c]benzo[f]indol-3,8-dione (35)

A solution of 28 (10.6 mg, 28.1 μmol) was treated with 4 M HCl/EtOAc and the mixture was stirred at 25° C. for 30 min. The volatiles were removed by a stream of $N_2$ and the residual salt was suspended in 1.0 mL of THF. The suspension was treated with 1.0 mL of 5% aqueous $NaHCO_3$ and stirred exposed to the air for 2 h at 25° C. The bright orange solution was extracted with EtOAc (3×5 mL), washed with $H_2O$(2×5 mL) dried ($Na_2SO_4$), and concentrated in vacuo. Flash chromatography ($SiO_2$, 1.5×15 cm, 60% EtOAc/hexane) provided pure 35 (3.5 mg, 63%) as an orange film: $^1$H NMR ($C_6D_6$, 400 MHz) δ8.14 (m, 1H), 8.05 (m, 1H), 7.00 (m, 2H), 3.62 (dd, J=6.2, 19.4 Hz, 1H), 3.52 (ddt, J=0.6, 2.2, 19.4 Hz, 1H), 2.55 (ddt, J=2.2, 6.0, 8.3 Hz, 1H), 1.54 (ddd, J=0.6, 3.3, 8.4 Hz, 1H), 0.30 (dd, J=3.3, 5.8 Hz, 1H); $^{13}$C NMR ($CDCl_3$, 100 MHz) δ191.6, 182.0, 168.9, 135.8, 135.6, 135.0, 134.6, 128.4, 127.0, 63.8, 49.7, 35.0, 30.4; IR (film) $v_{max}$ 2923, 1692, 1680, 1585, 1361, 1262, 1223, 1082 cm$^{-1}$; UV ($CH_3OH$)$\lambda_{max}$(ε) 271 (5200), 239 (13300) nm; FABHRMS (NBA/NaI) m/z 212.0715 ($C_{13}H_9NO_2$+H$^+$ requires 212.0712).

4-(tert-Butyloxycarbonyl)-1,2,2a,3-tetrahydrofurano [4,3,2-c,d]benzo[f]indole (36)

A neat sample of 31 (6.0 mg, 15 μmol) was allowed to sit under room light at 25° C. for 48 h to yield 36 (6.0 mg, 100%): $^1$H NMR ($CD_3CN$, 500 MHz) δ7.80 (d, J=8.0 Hz, 1H), 7.67 (d, J=7.7 Hz, 1H), 7.35 (m, 1H), 7.29 (m, 1H), 7.05 (br s, 1H), 5.22 (dd, J=8.0, 8.5 Hz, 1H), 4.64 (dd, J =9.0, 11.0 Hz, 1H), 4.40 (dd, J=8.5, 10.5 Hz, 1H), 4.22 (m, 1H), 3.88 (m, 1H), 1.55 (br s, 9H); IR (film) $v_{max}$ 2975, 2932, 1699, 1475, 1456, 1418, 1353, 1166, 1132 cm$^{-1}$; FABHRMS (NBA/NaI) m/z 297.1451 (M$^+$, $C_{18}$, $H_{19}NO_3$ requires 297.1365).

3-Chloromethyl-4-hydroxy- 1-[(5,6,7-trimethoxyindol-2-yl)carbonyl]-2,3-dihydro-1H-benzo[f]indole (43)

A sample of 28 (8.4 mg, 0.022 mmol) was treated with 1.0 mL of 3.6 N HCl/EtOAc and the resulting solution was stirred for 30 min at 25° C. The solvent was removed by a stream of $N_2$ and the residual salt was dried under vacuum. This salt was dissolved in 0.9 mL of anhydrous DMF and treated with 5,6,7-trimethoxyindole-2-carboxylic acid$^{10}$ (6.8 mg, 0.026 mmol) and EDCI (12.7 mg, 0.067 mmol) and the mixture was stirred for 3 h at 25° C. Upon completion, the reaction mixture was diluted with 20 mL of EtOAc, washed with $H_2O$ (5×3 mL), dried ($Na_2SO_4$), and concentrated in vacuo. Flash chromatography ($SiO_2$, 1.5×15 cm, 0–40% EtOAc/hexane gradient) provided 43 (11.2 mg, 91%) as a white solid: $^1$H NMR ($CDCl_3$, 400 MHz) δ9.41 (s, 1H), 8.35 (s, 1H), 7.88 (d, J=8.4 Hz, 1H), 7.82 (d, J=7.8 Hz, 1H), 7.45 (m, 1H), 7.41 (m, 1H), 6.96 (d, J=2.3 Hz, 1H), 6.85 (s, 1H), 5.95 (br s, 1H), 4.58 (m, 2H), 4.07 (m, 2H), 4.07 (s, 3H), 3.94 (s, 3H), 3.90 (s, 3H), 3.64 (dd, J=10.3, 12.0 Hz, 1H); $^{13}$C NMR (acetone-$d_6$, 400 MHz) δ193.6, 161.1, 151.0, 149.7, 143.4, 141.5, 136.7, 131.6, 128.8, 127.3, 126.5, 124.7, 124.5, 124.0, 121.9, 115.3, 107.6,107.2, 99.0, 61.44, 61.37, 56.4, 54.9, 46.6, 41.7; IR (film) $v_{max}$3405, 3301, 2937, 1594, 1446, 1312, 1228, 1106 cm$^{-1}$; FABHRMS (NBA/CsI) m/z 467.1358 ($C_{25}H_{23}ClN_2O_5$+H$^+$requires 467.1374). (−)-(3S)-43: [α]$_D^{25}$ −4 (c 0.22, CHCl$_3$);(+)-(3R)-43: [α]$_D^{25}$+4(c 0.35, CHCl$_3$).

2-[(5,6,7-Trimethoxyindol-2-yl)carbonyl]-1,2,9,9a-tetrahydrocyclo-propa[c]benzo [f]indol-8-one (iso-CBI-TMI, 44)

A solution of 43 (5.7 mg, 0.012 mmol) in 0.5 mL of $CH_3CN$ was treated with DBU (2.2 μL, 0.015 mmol) and stirred at 25° C. for 15 min. Flash chromatography (SiO1.5×10 cm, 50% EtOAc/hexane) provided pure 44 (4.2 mg, 94%) as a light golden oil: $^1$H NMR ($C_6D_6$, 400 MHz) δ9.65 (s, 1H), 8.36 (m, 1H), 7.76 (s, 1H), 7.10 (m, 1H), 7.03 (m, 1H), 6.94 (m, 1H), 6.77 (s, 1H), 6.45 (d, J=2.2 Hz, 1H), 3.78 (s, 3H), 3.70 (s, 3H), 3.54 (s, 3H), 3.52 (d, J=9.9 Hz, 1H), 3.26 (dd, J=5.2, 9.9 Hz, 1H), 2.43 (m, 1H), 1.57 (dd, J=3.3, 7.8 Hz, 1H), 0.70 (dd, J=3.3, 5.4 Hz, 1H); $^{13}$C NMR (adetone-$d_6$, 400MHz) δ194.5, 191.8, 161.7, 151.4, 147.1, 143.1, 142.0, 140.4, 135.6, 131.3, 129.4, 128.9, 127.3, 126.9, 126.7, 125.0, 112.7, 108.1, 107.6, 99.3, 63.7, 63.6, 57.0, 54.3, 40.6; IR (film) $v_{max}$ 3295, 2934, 1667, 1651, 1409, 1306, 1279, 1109 cm$^{-1}$; UV ($CH_3OH$) $\lambda_{max}$ 390 (ε7100), 332 (ε14100), 245 nm (ε19100); FABHRMS (NBA/NaI) m/z 431.1615 ($C_{25}H_{22}N_2O_5$+H$^+$requires 431.1607). (−)-(8aS,9aS)-44: [α]$_D^{25}$−41 (c 0.13, $CH_3OH$); (+)-(8aR,9aR)-44:[α]$_D^{25}$+38 (c 0.08, $CH_3OH$).

3-Chloromethyl-4-hydroxy-1-[(5-methoxyindol-2-yl) carbonyl]-2,3-dihydro-1H-benzo[f]indole (45)

Flash chromatography ($SiO_2$, 1.5×10 cm, 0–40% EtOAc/hexane gradient) afforded pure 45 (95%) as a clear oil: $^1$H NMR ($CDCl_3$, 400 MHz) δ9.38 (br s, 1H), 8.35 (s, 1H), 7.93 (d, J =7.6 Hz, 1H), 7.82 (d, J=7.9 Hz, 1H), 7.41 (m, 2H), 7.36 (d, J=9.0 Hz, 1H), 7.11 (d, J=2.2 Hz, 1H), 7.01 (m, 2H), 6.43 (s,1H), 4.63 (d, J=5.4 Hz, 2H), 4.11 (m, 2H), 3.86 (s, 3H), 3.64 (m, 1H); IR (film) $v_{max}$3287, 2927, 1665, 1596, 1518, 1445, 1402, 1389, 1290, 1231, 1167 cm$^{-1}$; FABHRMS (NBA/NaI) m/z 406.1071 ($C_{25}H_{19}ClN_2O_3$ requires 406.1084). (−)-(3S)-45: [α]$_D^{25}$−26 (c 0.07, $CH_3OH$); (+)-(3R)−45:[α]$_D^{25}$+25(c 0.04, $CH_3OH$).

2-[(5-Methoxyindol-2-yl)carbonyl]-1,2,9,9a-tetrahydrocyclopropa[c]benzo[f]indol-8-one (46)

Flash chromatography ($SiO_2$, 1.5×5 cm, 40% EtOAc/hexane) afforded 46 (85%) as a light golden oil: $^1$H NMR ($C_6D_6$, 400 MHz) δ9.15 (s, 1H), 8.38 (m, 1H), 7.80 (s, 1H), 7.12–7.05 (m, 4H), 6.94 (ddd, J=1.6, 6.8, 8.3 Hz, 1H), 6.85 (app dt, J=0.8, 8.6 Hz, 1H), 6.39 (d, J=1.6 Hz, 1H), 3.51 (s, 3H), 3.48 (d, J=10.0 Hz, 1H), 3.21 (dd, J=5.2, 10.0 Hz, 1H), 2.42 (dt, J=5.3, 7.8 Hz, 1H), 1.56 (dd, J=3.3, 7.8 Hz, 1H), 0.68 (dd, J=3.3, 5.3 Hz, 1H); IR (film) $v_{max}$ 3303, 2927, 1667, 1643, 1597, 1518, 1408, 1277, 1030, 1013 cm$^{-1}$; FABHRMS (NBA/NaI) m/z 371.1388 ($C_{23}H_{18}N_2O_3$+H$^+$ requires 371.1396). (−)-(8aS, 9aS) -46: [α]$_D^{25}$−66 (c 0.04, $CH_3OH$); (+)-(8aR,9aR)-46:[α]$_D^{25}$+71 (c0.03, $CH_3OH$).

3-Chloromethyl-4-hydroxy1-[((E)-3-(2-methoxyphenyl)propenyl)carbonyl]-2,3-dihydro-1H-benzo[f]indole (47)

Flash chromatography ($SiO_2$, 1.5×10 cm, 00% EtOA c/hexane gradient) afforded 47 (87%) as a pale yellow solid: $^1$H NMR ($CDCl_3$, 400 MHz) δ8.40 (br s, 1H), 7.87 (m, 3H), 7.40 (m, 2H), 7.31 (m, 1H), 7.22 (m, 1H), 7.20 (s, 1H), 6.93 (m, 2H), 5.81 (m, 1H), 4.36 (m, 2H), 4.09 (m, 2H), 3.85 (s, 3H), 3.65 (m, 1H); IR (film) $v_{max}$3266, 2963, 1659, 1598, 1445, 1377, 1269,1158, 1048 cm$^{-1}$; FABHRMS (NBA/NaI) m/z 394.1217 ($C_{25}H_{20}ClNO_3$+H$^+$requires 3 94.1210). (−)-(3S)-47: [α]$_D^{25}$−18(c0.15, $CH_3OH$); (+)-(3R)-47: 8 α]$_D^{25}$+ 22 (c 0.04, $CH_3OH$).

2-[((E)-3-(2-Methoxyphenyl)propenyl)carbonyl]-1,2, 9,9a-tetrahydrocyclo-propa[c]benzo[f]indol-8-one (48)

Flash chromatography ($SiO_2$, 1.5×5 cm, 40% EtOAc/hexane) afforded 48 (83%) as a light golden oil: $^1$H NMR ($C_6D_6$, 400 MHz) rotamers δ8.39 (d, J=7.5Hz, 1H), 8.09 (d, J=15.4 Hz, 1H), 7.15–6.95 (m, 8H), 6.76 (ddd, J=1.0, 2.5, 8.1 Hz, 1H), 3.70–3.50 (m, 1H), 3.31 (s, 3H), 3.00–2.80 (m, 1H), 2.35 (m, 1H), 1.63 (m, 1H), 0.73 (m, 1H); IR (film) $v_{max}$2929, 1673, 1626, 1471, 1408, 1383, 1265, 1156, 1092, 1044, 1009 cm$^{-1}$; FABHRMS (NBA/NaI) m/z 357.1360 (M$^+$, $C_{25}H_{19}NO_3$ requires 357.1365). (−)-(8aS,9aS)-48: $[α]_D^{25}$ −21 (c 0.08, $CH_3OH$); (+)-(8aR,9aR)-48: $[α]_D^{25}$ +23 (c0.03, $CH_3OH$).

3-Chloromethyl-4-hydroxy-1-{[5-[N-(indol-2-yl) carbonyl]aminoindol-2-yl]carbonyl}-2,3-dihydro- 1H-benzo [f]indole (49)

Flash chromatography (SiO$_2$, 1.5×10 cm, 40–80% EtOAc/hexane gradient) afforded 49 (74%) as a light brown solid: $^1$H NMR(DMF-d$_7$, 400 MHz) δ11.76 (s, 2H), 10.30 (s, 1H), 10.28 (s, 1H), 8.41 (s, 1H), 8.29 (s, 1H), 8.25 (d, J=8.0 Hz, 1H), 7.81 (d, J=8.4 Hz, 1H), 7.71 (dd, J=2.8, 9.2 Hz, 1H), 7.69 (d, J=9.6 Hz, 1H), 7.59 (d, J=8.6 Hz, 2H), 7.52 (s, 1H), 7.46 (m, 1H), 7.40 (m, 1H), 7.30 (d, J=1.6 Hz,1H), 7.25 (m, 1H), 7.09 (m, 1H), 4.83 (m, 1H), 4.70 (dd, J=2.4, 10.4 Hz, 1H), 4.30 (m, 1H), 4.16 (dd, J=2.8, 11.2 Hz, 1H), 3.98 (dd, J=8.8, 11.2 Hz, 1H); IR (film) $v_{max}$3280, 2929, 1660, 1650, 1594, 1519, 1443, 1389, 1314, 1250, 1098, 749 cm$^{-1}$; FABHRMS (NBA/CsI) m/z 667.0529 ($C_{31}H_{23}ClN_4O_3$ +Cs$^+$ requires 667.0513). (−)-(3S)-49: $[α]_D^{25}$ −18 (c 0.10, $CH_3OH$); (+)-(3R)-49: $[α]_D^{25}$ +21 (c 0.06, $CH_3OH$).

2-{[5-[N-(indol-2-yl)carbonyl]aminoindol-2-yl] carbonyl}-1,2,9,9a-tetrahydrocyclopropa[c]benzo[f] indol-8-one (iso-CBI-indole$_2$, 50)

Flash chromatography (SiO$_2$, 1.5×10 cm, 10% DMF/ toluene) afforded 50 (88%) as a light golden solid: $^1$H NMR (DMF-d$_7$, 400 MHz) δ6 11.75 (s, 1H), 11.72 (s, 1H), 10.28 (s, 1H), 8.37 (s, 1H), 7.96 (d, J=7.9 Hz, 1H), 7.73–7.64 (m, 3H), 7.58 (t, J=8.1 Hz, 2H), 7.50 (m, 2H), 7.35 (m, 2H), 7.23 (m, 2H), 7.08 (t, J=7.3 Hz, 1H), 4.57 (m, 2H), 3.09 (dt, J=5.5, 7.7 Hz, 1H), 1.86 (dd, J=3.1, 7.7 Hz, 1H), 1.77 (dd, J=3.2, 5.5 Hz, 1H); IR (film) $v_{max}$ 3289, 2927, 1668, 1652, 1557, 1520, 1409, 1313 cm$^{-1}$; FABHRMS (NBA/CsI) m/z 499.1752 ($C_{31}H_{22}N_4O_3$+H$^+$requires 499.1770). (−)-(8aS, 9aS)-50: $[α]_D^{25}$−21 (c 0.10, DMF); (+)-(8aR,9aR)-50:$[α]_D^{25}$+21 (c 0.06, DMF).

1-[(3-Carbamoyl-1,2-dihydro-3H-pyrrolo[3,2-e] indol-7-yl)carbonyl]-3-chloromethyl-4-hydroxy-2,3- dihydro-1H-benzo[f]indole (51)

Flash chromatography (SiO$_2$, 1.5×10 cm, 10–50% DMF/ toluene gradient) afforded pure 51 (80%) as a yellow solid: $^1$H NMR (DMF-d$_7$, 400 MHz) δ11.64 (s, 1H), 10.32 (s, 1H), 8.28 (s, 1H), 8.25 (d, J=8.4 Hz, 1H), 8.16 (d, J=8.9 Hz, 1H), 7.81 (d,J=8.1 Hz, 1H), 7.46 (m, 1H), 7.39 (m, 2H), 7.15 (d, J=1.7 Hz, 1H), 6.13 (s, 2H), 4.82 (m, 1H), 4.68 (dd, J=2.7, 10.8 Hz, 1H), 4.30 (m, 1H), 4.15 (m, 3H), 3.97 (dd, J=8.3, 10.8 Hz, 1H), 3.39 (m, 2H); IR (film) $v_{max}$ 3337, 2924, 1662, 1652, 1513, 1456, 1441, 1400, 1344, 1272 cm$^{-1}$; ESIMS m/z 461 (M+H$^+$, $C_{25}H_{21}ClN_4O_3$ requires 461). (−)-(3S)-51: $[α]_D^{25}$−21 (c 0.18, DMF); (+)-(3R)-51: $[α]_D^{25}$+22 (c 0.13, DMF).

2-[(3-Carbamoyl-1,2-dihydro-3H-pyrrolo[3,2-e] indol-7-yl)carbonyl]-1,2,9,9a-tetrahydrocyclopropa [c]benzo[f]indol-8-one (iso-CBI-CDPI$_1$, 52)

Flash chromatography (SiO$_2$, 1.5×10 cm, 30–50% DMF/ toluene gradient) afforded 52 (81%) as a brown solid: $^1$H NMR (DMF-d$_7$, 400 MHz) δ11.60 (s, 1H), 8.15 (d, J=8.8 Hz, 1H), 7.95 (d, J=7.6 Hz, 1H), 7.66 (t, J=7.4 Hz, 1H), 7.49 (d, J=7.8 Hz, 1H), 7.35 (m, 3H), 7.10 (s, 1H), 6.13 (s, 2H), 4.55 (m, 2H), 4.13 (t, J=8.8 Hz, 2H), 3.36 (t, J=9.1 Hz, 2H), 3.09 (m, 1H), 1.85 (dd, J=2.9, 7.6 Hz, 1H), 1.76 (dd, J=3.3, 5.4 Hz, 1H); IR (film) $v_{max}$ 3346, 2927, 1667, 1651, 1505, 1435, 1408, 1343, 1279, 1098 cm$^{-1}$; ESIMS m/z 425 (M+H$^+$, $C_{25}H_{20}N_4O_3$ requires 425). (−)-(8aS,9aS)-52: $[α]_D^{25}$−13 (c 0.06, DMF); (+)-(8aR,9aR)-52: $[α]_D^{25}$+12 (c 0.07, DMF).

1-{[3-[N-(3-Carbamoyl-1,2-dihydro-3H-pyrrolo[3,2- e]indol-7-yl)carbonyl]-1,2-dihydro-3H-pyrrolo[3,2- e]indol-7-yl]carbonyl}-3-chloromethyl-4-hydroxy-2, 3-dihydro-1H-benzo[f]indole (53)

Flash chromatography (SiO$_2$, 1.5×15 cm, 10–50% DMF/ toluene gradient) afforded pure 53 (32%) as a red solid: $^1$H NMR (DMF-d$_7$, 400 MHz) δ11.85 (s, 1H), 11.54 (s, 1H), 10.33 (s, 1H), 8.39 (m, 1H), 8.30 (s, 1H), 8.26 (d, J=8.4 Hz, 1H), 8.13 (d, J=8.9 Hz, 1H), 7.82 (d, J=8.0 Hz, 1H), 7.48 (m, 2H), 7.38 (m, 2H), 7.31 (s, 1H), 7.08 (s, 1H), 6.10 (s, 2H), 4.86 (m, 1H), 4.73 (m, 3H), 4.31 (m, 1H), 4.15 (m, 3H), 3.99 (dd, J=8.2, 10.7 Hz, 1H), 3.55 (m, 2H), 3.39 (m, 2H); IR (film) $v_{max}$ 3338, 2956, 2927, 1727, 1659, 1650, 1604, 1510, 1402, 1365, 1286 cm$^{-1}$; ESIMS m/z 645/647 (M+H$^+$, $C_{36}H_{29}ClN_6O_4$ requires 645/647). (−)-(3S)-53: $[α]_D^{25}$−19 (c 0.10, DMF); (+)-(3R)-53: $[α]_D^{25}$+21 (c 0.08, DMF).

2-{[3-[N-(3-Carbamoyl-1,2-dihydro-3H-pyrrolo[3,2- e]indol-7-yl)carbonyl]-1,2-dihydro-3H-pyrrolo[3,2- e]indol-7-yl]carbonyl}-1,2,9,9a- tetrahydrocyclopropa[c]benzo[f]indol-8-one (iso- CBI-CDPI$_2$, 54)

Flash chromatography (SiO$_2$, 1.5×10 cm, 50% DMF/ toluene) afforded 53 (59%) as a brown solid: $^1$H NMR (DMF-d$_7$, 400 MHz) δ11.80 (s, 1H), 11.53 (s, 1H), 8.37 (m, 1H), 8.13 (d, J=8.9 Hz, 2H), 7.65 (m, 1H), 7.49 (d, J=7.8 Hz, 1H), 7.47 (d, J=9.1 Hz, 1H), 7.36 (m, 3H), 7.24 (d, J=1.5 Hz, 1H), 7.07 (s, 1H), 6.12 (s, 2H), 4.74 (t, J=8.4 Hz, 2H), 4.58 (m, 2H), 4.14 (t, J=8.9 Hz, 2H), 3.52 (m, 2H), 3.38 (t, J=8.8 Hz, 2H), 3.11 (m, 1H), 1.87 (dd, J=3.1, 7.8 Hz, 1H), 1.78 (dd, J=3.1, 5.5 Hz, 1H); IR (film) $v_{max}$ 3293, 2926, 1665, 1612, 1581, 1503, 1431, 1409, 1363, 1344, 1278, 1185 cm$^{-1}$; ESIMS m/z 607 (M−H$^+$, $C_{36}H_{28}N_6O_4$ requires 607). (−)-(8aS,9aS)-54: $[α]_D^{25}$−34 (c 0.05, DMF); (+)-(8aR,9aR)- 54: $[α]_D^{25}$+33 (c 0.03, DMF).

Solvolysis Regioselectivity: 1-(tert- Butyloxycarbonyl)-4-hydroxy-3-(methoxymethyl)-2, 3-dihydro-1H-benzo[f]indole (62)

A solution of 31 (7.7 mg, 0.026 mmol) in 2.5 mL of $CH_3OH$ was cooled to 0° C., and $CF_3SO_3H$ in $CH_3OH$ (311 μL, 0.01 N, 0.12 equiv) was added. After slowly warming to 25° C. over 17 h, the reaction was quenched by the addition of $NaHCO_3$ (2.1 mg), filtered through Celite and concentrated under reduced pressure. Flash chromatography (SiO$_2$, 1.5×15 cm, 0–40% EtOAc/hexane gradient) yielded the major isomer 62 (8.0 mg, 94%) as a white film: $^1$H NMR (CDCl$_3$, 400 MHz) δ9.05 (s, 1H), 8.12 (d, J=6.4 Hz, 1H), 7.80 (m, 1H), 7.65 (s, 1H), 7.37 (m, 1H), 7.29 (m, 1H), 4.17 (m, 1H), 3.83 (m, 1H), 3.77 (dd, J=2.8, 6.4 Hz, 1H), 3.60 (dd, J=6.8, 8.8 Hz, 1H), 3.54 (s, 3H), 3.49 (m, 1H), 1.56 (s, 9H); IR (film) $v_{max}$ 3233, 2975, 1704, 1644, 1435, 1348, 1148, 1026, 956 cm$^{-1}$; FABHRMS(NBA/NaI) m/z 352.1535 ($C_{19}H_{23}NO_4$+Na$^+$ requires 352.1525).

For the minor isomer 63 (<2% by $^1$H NMR of the crude reaction mixture): $^1$H NMR (CDCl$_2$, 500 MHz) δ8.10 (m, 1H), 7.95 (d, J=6.5 Hz, 1H), 7.73 (m, 1H), 7.38 (m, 1H), 7.33 (m, 1H), 7.24 (m, 1H), 4.13 (m, 1H), 3.98 (s, 3H), 3.92 (m, 1H), 3.81 (m, 2H), 3.50 (m, 1H), 1.57 (s, 9H); FAB-HRMS (NBA/NaI) m/z 352.1534 ($C_{19}H_{23}NO_4+Na^+$ requires 352.1525).

Preparation of Authentic 62: A solution of 27 (17.3 mg, 0.05 mmol) in 1.6 mL anhydrous DMF was treated with NaH (4.3 mg, 0.14 mmol) in small portions and the resulting suspension was stirred for 15 min at 0° C. Methyl iodide (18 μL, 0.29 mmol) was added neat and the resulting mixture warmed to 25° C. over 2 h. The reaction mixture was quenched with the addition of 5% aqueous $NaHCO_3$ (10 mL), and the aqueous layer was extracted EtOAc (3×5 mL). The combined organic extracts were washed with $H_2O$ (5×5 mL), dried ($Na_2SO_4$) and concentrated under reduced pressure. The crude mixture was subjected to flash chromatography ($SiO_2$, 1.5×15 cm, 10% EtOAc-hexanes) to yield the intermediate methyl ether 64 (14.0 mg, 78%) as a colorless oil. 64 was subjected to the selective MOM deprotection reaction and purification as detailed for 30 to yield the major solvolysis product 62, identical in all aspects.

Figure 9A:
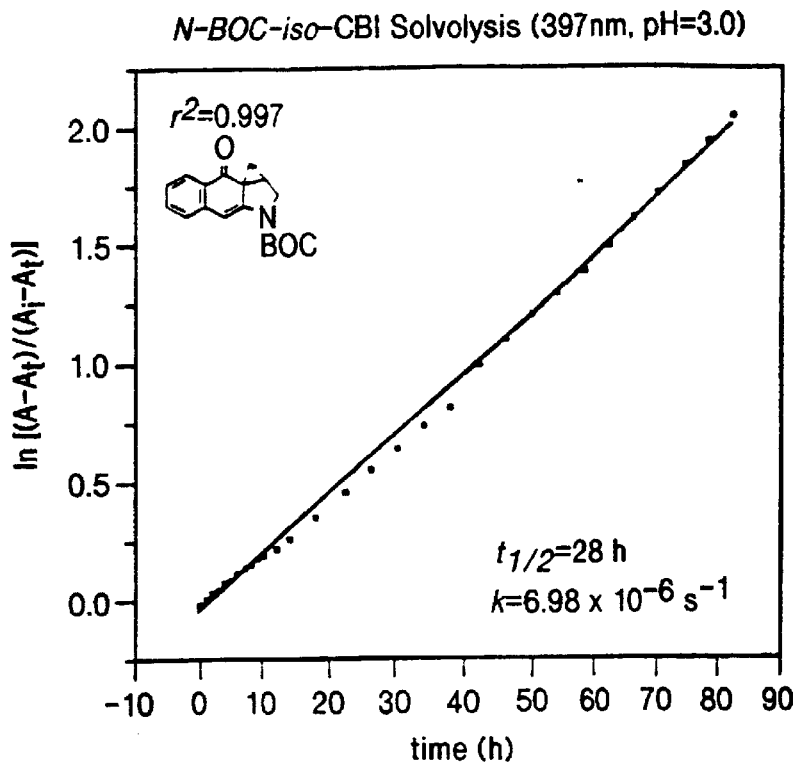
FIGS. 9A–9C illustrate solvolysis data for the indicated compounds.
Figure 9B:
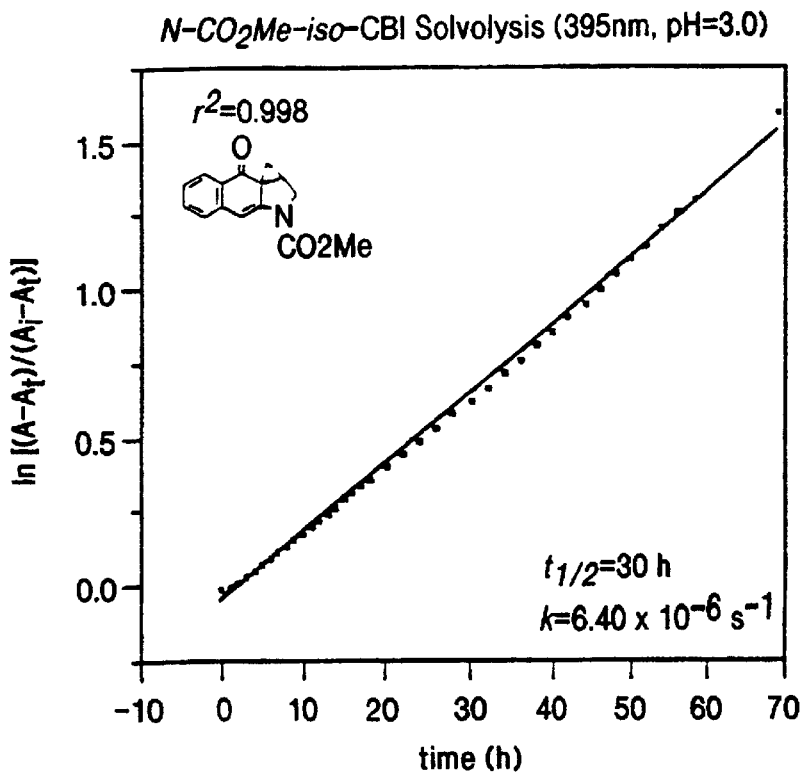
Figure 9C:
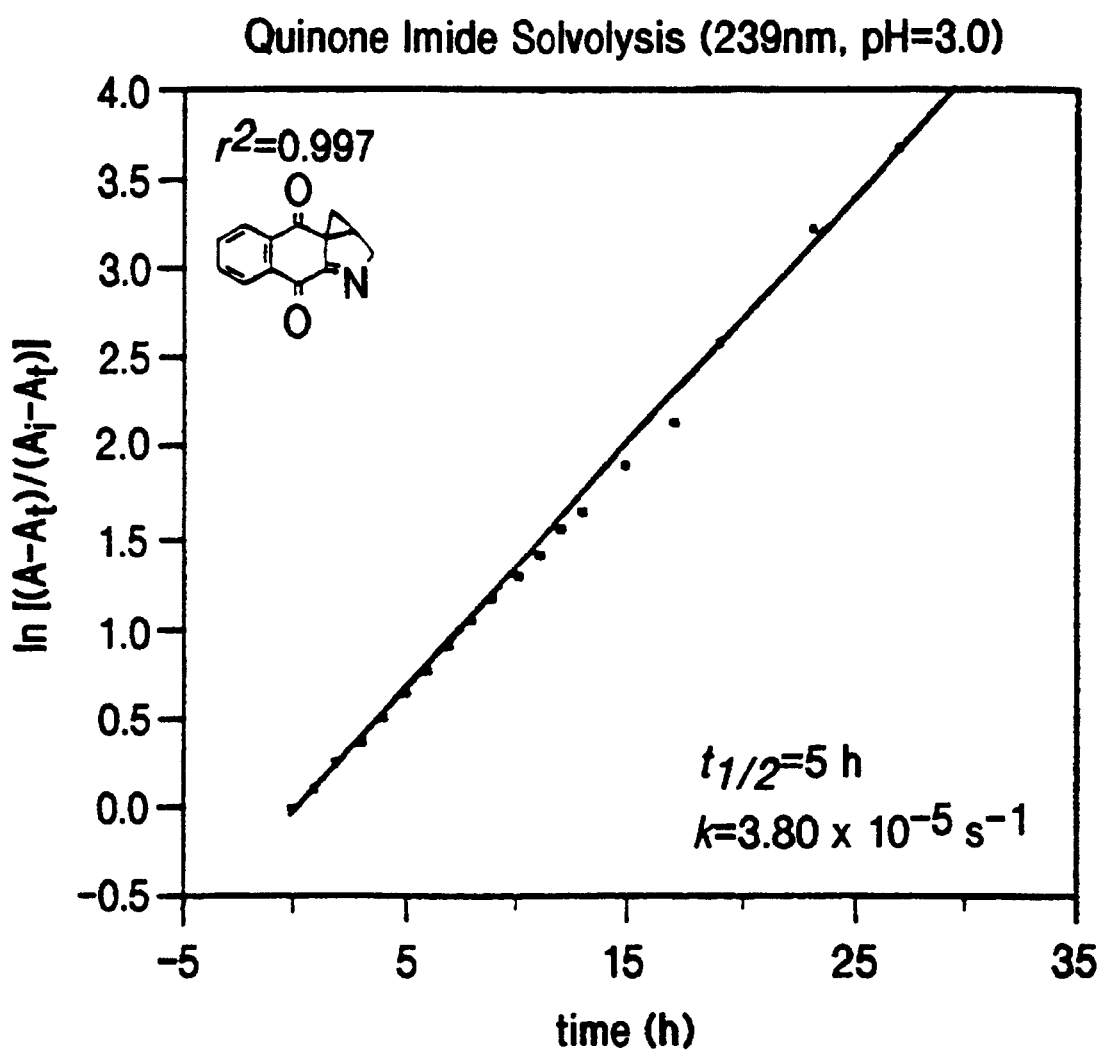

Solvolysis Reactivity: N-BOC-iso-CBI (31, 0.2 mg) was dissolved in $CH_3OH$ (1.5 mL) and mixed with pH 3 aqueous buffer (1.5 mL). The buffer contained 4:1:20 (v/v/v) 0.1 M citric acid, 0.2 M $Na_2HPO_4$, and $H_2O$, respectively. The solvolysis solution was sealed and kept at 25° C. protected from light. The UV spectrum was measured at regular intervals every 1 h during the first 24 h, every 4 during the next 72 h, and every 12 h for an additional week. The decrease in the long wavelength absorption at 397 nm was monitored, FIG. 3. The solvolysis rate constant (k=6.98× $10^{-6}$ $s^{-1}$) and the half-life ($t_{1/2}$=28 h) were calculated from data recorded at the long wavelength from the least-squares treatment (r=0.99) of the slope of the plot of time versus $\ln[(A_f-A_i)/(A_f-A)]$ (FIG. 9).

Similarly, N-$CO_2$Me-iso-CBI (33, 0.2 mg) was dissolved in $CH_3OH$ (1.5 mL) and mixed with pH 3 aqueous buffer (1.5 mL). The solvolysis solution was sealed and kept at 25° C. protected from light. The UV spectrum was measured at regular intervals every 1 h during the first 24 h, every 4 h during the next 72 h, and every 12 h for an additional week. The decrease in the long wavelength absorption at 395 nm was monitored, FIG. 3. The solvolysis rate constant (k=6.40×$10^{-6}$ $s^{-1}$) and the half-life ($t_{1/2}$=30 h) were determined as detailed above (r=0.99).

Similarly, 35 (0.2 mg) was dissolved in $CH_3OH$ (1.5 mL) and mixed with pH 3 aqueous buffer (1.5 mL). The solvolysis solution was sealed and kept at 25° C. protected from light. The UV spectrum was measured at regular intervals every 1 h during the first 12 h, every 2 h for the next 24 h, and every 4 h for an additional day. The decrease in the short wavelength absorption at 239 nm was monitored, FIG. 9. The solvolysis rate constant (k=3.80×$10^{-5}$ $s^{-1}$) and the half-life ($t_{1/2}$=5 h) were determined as detailed above (r=0.99).

Isolation, Characterization and Quantitation of the Thermally Released (−)-iso-CBI-TMI Adenine Adduct 66

(−)-iso-CBI-TMI (44, 1.0 mg, 2.32 μmol) in 500 μL of DMSO was added to a solution of calf thymus DNA (Sigma, 220 mg, ca. 150 bp) in 10 mM sodium phosphate buffer (13 mL, pH 7.0) in 50 mL centrifuge tube. The mixture was cooled at 4° C. for 72 h, and then extracted with EtOAc (3×10 mL) to remove hydrolyzed, rearranged (65) or unreacted 44. UV and HPLC assay of the EtOAc extracts revealed no unreacted 44 (0%) and <5% rearranged 65. The centrifuge tube containing the aqueous DNA layer was sealed with Teflon tape and warmed at 100° C. for 30 min. The resulting solution was cooled to 25° C. and extracted with EtOAc (3×10 mL). The combined organic layer was dried ($Na_2SO_4$) and concentrated under reduced pressure to afford a yellow solid. Chromatography ($SiO_2$, 0.5×3 cm, 0–7% $CH_3OH/CHCl_3$ gradient elution) afforded (+)-66 as a pale yellow solid (1.25 mg, 1.31 mg theoretical, 95%, 90–95% in four runs) contaminated with a small impurity (<5% by HPLC). For 66: $[\alpha]_D^{23}$+28 (c 0.06, $CH_3OH$); $R_f$=0.3 ($SiO_2$, 10% $CH_3OH/CHCl_3$); $^1$H NMR (acetone-$d_6$, 400 MHz) δ10.37 (s, 1H, N1'—H), 8.58 (s, 1H, ArOH), 8.31 (d, J=7.9 Hz, 1H, Ar—H), 8.22 (s, 1H, Ade-C8—H), 8.07 (s, 1H, Ade-C2—H), 7.78 (d, J=7.9 Hz, 1H, Ar—H), 7.49 (br s, 1H, Ar—H), 7.45 (ddd, J=1.3, 6.8, 7.9 Hz, 1H, Ar—H), 7.38 (ddd, J=1.3, 6.8, 7.9 Hz, 1H, Ar—H), 7.10 (d, J=2.3 Hz, 1H, C3'—H), 6.93 (s, 1H, C5'—H), 4.92 (dd, J=10.6, 1.9 Hz, 1H, CHH-Ade), 4.89 (dd, J=14.5, 7.0 Hz, 1H, CHHNCO), 4.74 (dd, J=14.5, 7.6 Hz, 1H, CHHNCO), 4.73 (dd, J=10.8, 2.2 Hz, 1H, CHH-Ade), 4.37 (m, 1H, $CH_2CHCH_2$), 4.04 (s, 3H, $OCH_3$), 3.87 (s, 3H, $OCH_3$), 3.86 (s, 3H, $OCH_3$); $^1$H NMR (DMSO-$d_6$+1% d-TFA, 400 MHz) δ11.40 (s, 1H, N1'—H), 9.28 (br s, 1H, NHH), 8.78 (br s, 1H, NHH), 8.45 (s, 1H, Ade-C8—H), 8.40 (s, 1H, Ade-C2—H), 8.07 (d, J=7.2 Hz, 1H, Ar—H), 8.05 (br s, 1H, ArOH), 7.76 (d, J=7.2 Hz, 1H, Ar—H), 7.43 (dd, J=6.4, 6.4 Hz, 1H, Ar—H), 7.35 (dd, J=6.4, 6.4 Hz, 1H, Ar—H), 6.95 (s, 1H, C3'—H), 6.90 (s, 1H, C5'—H), 4.72 (dd, J=10.8, 5.6 Hz, 1H, CHH-Ade), 4.68 (dd, J=10.8, 5.6 Hz, 1H, CHH-Ade), 4.55 (dd, J=9.0, 9.0 Hz, 1H, CHHNCO), 4.54 (br d, J=9.0 Hz, 1H, CHHNCO), 4.36 (m, 1H), 3.93 (s, 3H, $OCH_3$), 3.80 (s, 3H, $OCH_3$), 3.79 (s, 3H, $OCH_3$); $^{13}$C NMR (150 MHz, acetone-$d_6$) δ170.5, 161.0, 156.9, 152.2, 151.2, 151.0, 150.0, 143.9, 142.9, 141.4, 140.0, 136.7, 131.8, 128.4, 127.2, 126.4, 124.7, 124.6, 124.1, 123.0, 114.2, 107.3, 106.1, 98.9, 61.5, 61.4, 57.5, 56.5, 56.4, 39.8; IR (film) $v_{max}$ 3251, 2911, 2850, 1684, 1647, 1458, 1312, 1200, 1024 $cm^{-1}$; UV ($CH_3OH$) $\lambda_{max}$ 331 (ε12400), 300 (ε12600), 240 nm (ε17700); FAB-HRMS (NBA) m/z 566.2074 (M+H$^+$, $C_{30}H_{27}N_7O_5$ requires 566.2083).

HPLC $t_R$ (4×250 nm column, 1.0 mL/min, 35% $CH_3CN$/ 0.05 N aqueous $HCO_2NH_4$) were 44 (21.6 min), 65 (39.0 min), solvolysis product (24.0 min), and 66 (17.5 min).

Methoxymethyl 3-Nitrophenyl Ether (11)

A solution of 3-nitrophenol (5.00 g, 36 mmol) in 100 mL of anhydrous DMF at 0° C. was treated with NaH (2.16 g, 54 mmol) in several portions over 5 min. After 10 min, $Bu_4NI$ (1.33 g, 3.6 mmol) was added and followed by dropwise addition of $ClCH_2OCH_3$ (4.1 mL, 54 mmol). The reaction mixture was stirred at 25° C. for 21 h before being quenched with the slow addition of 100 mL of $H_2O$. The aqueous layer was extracted with EtOAc (3×100 mL). The organic layers were combined, washed with 10% aqueous $NaHCO_3$ (100 mL), $H_2O$ (4×50 mL), dried $Na_2SO_4$), and concentrated under reduced pressure. Flash chromatography ($SiO_2$, 4×15 cm, 10% EtOAc/hexane) provided 11 (5.83 g, 89%) as a pale yellow solid: $^1$H NMR ($CDCl_3$, 250 MHz) δ7.86 (m, 2H), 7.34 (m, 2H), 5.22 (s, 2H), 3.46 (s, 3H); $^{13}$C NMR ($CDCl_3$, 62.5 MHz) δ157.5, 148.9, 129.9, 122.6, 116.5, 110.9, 94.4, 56.1; IR (film) $v_{max}$ 3099, 2959, 2829, 1619, 1584, 1537, 1349, 1237, 1153, 1081 $cm^{-1}$; FAB-HRMS (NBA/NaI) m/z 206.0430 ($C_8H_9NO_4+Na^+$ requires 206.0429).

Anal. Calcd for $C_8H_9NO_4$: C, 52.46; H, 4.95; N, 7.65. Found: C, 52.37; H, 4.89; N, 7.61.

3-Aminophenyl Methoxymethyl Ether (12)

A solution of 11 (5.68 g, 31 mmol) in 310 mL moist ether (8:2:1 $Et_2O$/EtOH/$H_2O$) was cooled to 0° C., and treated with freshly prepared Al—Hg (5.2 g Al, 217 mmol) in small 1×1 cm pieces. The reaction mixture was stirred vigorously for 0.5 h at 0° C., and 1 h at 25° C. The reaction mixture was filtered through Celite, and the Celite was washed thoroughly with $Et_2O$ (5×50 mL). The filtrate was washed with saturated aqueous NaCl (300 mL), dried ($Na_2SO_4$), and concentrated under reduced pressure to afford 12 (4.23 g, 89%) as a golden oil, which was immediately carried on to the next step without further purification. For 12: $^1H$ NMR (CDCl$_3$, 250 MHz) δ7.05 (t, J=8.0 Hz, 1H), 6.38 (m, 3H), 5.12 (s, 2H), 3.70 (br s, 2H), 3.46 (s, 3H); $^{13}C$ NMR (CDCl$_3$, 250MHz) 158.2, 147.7, 129.9, 108.7, 106.0, 102.9, 94.0, 55.7;IR (film) $v_{max}$ 3452, 3367, 2955, 2900, 1623, 1601, 1494, 1287, 1147, 1074, 1009 cm$^{-1}$; FABHRMS (NBA/NaI) m/z 153.0786 ($C_8H_{11}NO_2$ requires 153.0790).

[N-(tert-Butyloxycarbonyl)amino]-3-(methoxymethoxy)benzene (13)

A solution of crude 12 (4.13 g, 27 mmol) in 135 mL anhydrous THF was treated with BOC$_2$O (12.14 g, 54 mmol) and the reaction mixture was warmed at reflux (65° C.) for 18 h. The solvents were removed under reduced pressure, and flash chromatography (SiO$_2$, 4×15 cm, 20% EtOAc/hexane) provided pure 13 (6.83 g, 100%) as a yellow oil: $^1H$ NMR (CDCl$_3$, 250 MHz) δ7.15 (m, 2H), 6.94 (m, 1H), 6.68 (m, 1H), 6.58 (br s, 1H), 5.13 (s, 2H), 3.44 (s, 3H), 1.50 (s, 9H); $^{13}C$ NMR (CDCl$_3$, 62.5 MHz) δ157.7, 152.5, 139.5, 129.6, 111.9, 110.7, 106.6, 94.2, 80.5, 55.9, 28.2; IR (film) $v_{max}$ 3337, 2977, 1728, 1605, 1537, 1236, 1153, 1015 cm$^{-1}$; FABHRMS (NBA/NaI) m/z 276.1203 ($C_{13}H_{19}NO4+Na^+$ requires 276.1212)

[N-(tert-Butyloxycarbonyl)amino]-2-iodo-3-(methoxymethoxy)benzene (14)

A solution of 13 (124 mg, 0.49 mmol) in 2.0 mL anhydrous THF was cooled to –20° C. and treated with TMEDA (0.26 mL, 1.71 mmol) followed by n-BuLi (0.69 mL of a 2.5 M solution in hexanes, 1.71 mmol) in a slow dropwise manner. The resulting gold solution stirred for 4 h at –20° C. The reaction mixture was treated with 1-chloro-2-iodoethane (0.126 mL, 1.71 mmol) and stirred for 15 min at 25° C. The reaction was diluted with $H_2O$ (30 mL), extracted with $Et_2O$ (3×20 mL), and the combined organic extracts were washed with saturated aqueous NaCl, dried Na$_2$SO$_4$) and concentrated under reduced pressure. Flash chromatography (SiO$_2$, 2.5×10 cm, 0–10% EtOAc/hexane gradient) yielded recovered 13 (51.8 mg, 41%) and 14 (85.5 mg, 46%) as a white solid: mp 82–84° C.; $^1H$ NMR (CDCl$_3$, 400 MHz) δ7.72 (d, J=8.2 Hz, 1H), 7.21 (t, J=6.0 Hz, 1H), 7.01 (br s, 1H), 6.72 (dd, J=1.2, 8.2 Hz, 1H), 5.21 (s, 2H), 3.47 (s, 3H), 1.49 (s, 9H);$^{13}C$ NMR (CDCl$_3$, 100 MHz) δ156.0, 152.5, 140.1, 129.5, 113.4, 108.9, 94.8, 82.4, 80.9, 54.4, 28.3; IR (film) $v_{max}$ 3388, 2977, 1736, 1592, 1515, 1465, 1406, 1252, 1226, 1153, 1005 cm$^{-1}$; FABHRMS (NBA/CsI) m/z 511.9351 ($C_{13}H_{18}INO_4+Cs^+$ requires 511.9335).

Anal. Calcd for $C_{13}H_{18}INO_4$: C, 41.18; H, 4.78; N, 3.69. Found: C, 41.19; H, 5.11;N, 3.79.

[N-(tert-Butyloxycarbonyl)-N-(2-propen-1-yl)amino]-2-iodo-3-(methoxymethoxy)benzene (15)

A solution of 14 (141 mg, 0.37 mmol) in 12 mL anhydrous DMF was cooled to –10° C., and treated with NaH (22.3 mg, 0.55 mmol) in small portions. The resulting suspension was stirred for 15 min and treated with neat allyl bromide (0.16 mL, 1.56 mmol) in a slow dropwise manner. The reaction mixture was warmed to 25° C. and stirred for 1 h. The reaction mixture was quenched with the addition of 5% aqueous NaHCO$_3$ (20mL), and the aqueous layer was extracted with EtOAc (3×10 mL). The combined organic extracts were washed with $H_2O$ (5×10 mL), dried (Na$_2$SO$_4$), and condensed under reduced pressure to yield 15 as a 2:1 mixture of amide rotamers as a yellow oil. Flash chromatography (SiO$_2$, 2.5×10 cm, 10% EtOAc/hexane) yielded 15 (149 mg, 96%) as a colorless oil:$^1H$ NMR (CDCl$_3$, 250 MHz) δ7.17 (m, 1H), 6.95–6.78 (m, 2H), 5.98–5.84 (m, 1H), 5.21 (s, 2H), 5.09–5.03 (m, 2H), 4.46 (m, 1H), 3.50 (s, 3H), 1.50 and 1.31 (s, 9H);$^{13}C$ NMR (CDCl$_3$, 100 MHz) δ157.5 and 157.0, 153.7, 146.1 and 145.7, 133.8 and 133.6, 129.5 and 129.0, 123.6 and 123.5, 117.6 and 117.1, 113.5 and 113.2, 95.0 and 94.1, 80.5 and 80.1, 56.4, 53.1, 51.9, 28.3 and 28.1; IR (film) $v_{max}$ 2975, 1688, 1582, 1463, 1381, 1253, 1154, 1065, 990 cm$^{-1}$; FABHRMS (NBA/NaI) m/z 420.0663 ($C_{16}H_{22}INO_4+H^+$ requires 420.0672).

1-(tert-Butyloxycarbonyl)-4-(methoxymethoxy)-3-[[(2',2',6',6'-tetramethyl-piperidino)oxy]methyl]-2,3-dihydroindole (16)

A solution of 15 (142 mg, 0.33 mmol) and TEMPO (160 mg, 1.0 mmol) in 14.3 mL anhydrous benzene was treated with Bu$_3$SnH (96 μL, 0.35 mmol). The solution was warmed at 50° C. and an additional 1.05 equiv of Bu$_3$SnH (96 μL, 0.35 mmol) was added twice during the next 30 min. Another 3.0 equiv of TEMPO (160 mg, 1.0 mmol) was added in 3 mL anhydrous benzene, and an additional 1.05 equiv of Bu$_3$SnH added twice during the next 45 min. After 1.5 h total, the solution was cooled to 25° C., and the volatiles were removed under reduced pressure. Flash chromatography (SiO$_2$, 2.5×10 cm, 0–8% EtOAc/hexane gradient) provided 16 (138 mg, 91%) as a yellow oil: $^1H$ NMR (CDCl$_3$, 250 MHz) δ7.51 (br s, 1H), 7.11 (m, 1H), 6.67 (d, J=8.7 Hz, 1H), 5.16 (s, 2H), 4.13 (dd, J=3.3, 11.4 Hz, 1H), 4.07 (m, 1H), 3.93 (m, 1H), 3.76 (m, 1H), 3.54 (m, 1H), 3.46 (s, 3H), 1.55 (s, 9H), 1.47–0.76 (m, 18H); $^{13}C$ NMR (C$_6$D$_6$, 100 MHz) δ154.2, 152.2, 145.4, 129.8, 119.0, 109.6, 108.1, 94.4, 79.8, 77.3, 60.0, 55.7, 52.4, 39.9, 33.3, 28.3, 20.1, 17.4; IR (film) $v_{max}$ 2974, 2931, 1707, 1609, 1462, 1389, 1250, 1154, 1009 cm$^{-1}$; FABHRMS (NBA/CsI) m/z 581.1977 ($C_{25}H_{40}N_2O_5+H^+$ requires 581.1992).

1-(tert-Butyloxycarbonyl)-3-(hydroxymethyl)-4-(methoxymethoxy)-2,3-dihydroindole (17)

A solution of 16 (135 mg, 0.30 mmol) in 10 mL 3:1:1 HOAc/H$_2$O/THF was treated with Zn powder (780 mg, 12.0 mmol) and the resulting suspension was warmed at 70° C. under a reflux condenser and with vigorous stirring for 2 h. The reaction mixture was cooled to 25° C., and the Zn was removed by filtration through Celite (CH$_2$Cl$_2$ wash). The volatiles were removed under reduced pressure, and the resulting residue was dissolved in 15 mL EtOAc and filtered. The solution was concentrated under reduced pressure and subjected to flash chromatography (SiO$_2$, 2.5×10 cm, 30–40% EtOAc/hexane gradient) to provide 16 (84 mg, 87%) as a colorless oil: $^1H$ NMR (CDCl$_3$, 400 MHz) δ7.53 (br s, 1H), 7.11 (m, 1H), 6.67 (d, J=8.8 Hz, 1H), 5.18 (d, J=8.6 Hz, 1H), 5.16 (d, J=8.6 Hz, 1H), 4.02 (dd, J=10.1, 11.5 Hz, 1H), 3.84 (m, 2H), 3.71 (dd, J=5.9 10.4 Hz, 1H), 3.61 (m, 1H), 3.46 (s, 3H), 1.53 (s, 9H);$^{13}C$ NMR (CDCl$_3$, 100 MHz) δ153.6, 152.3, 129.7, 110.9, 110.0, 109.0, 107.8, 106.6, 94.2, 64.7, 56.2, 51.3, 41.0, 28.3; IR (film) v$_{max}$ 3444, 2975, 1704, 1608, 1463, 1392, 1252, 1153, 1004 cm$^{-1}$; FABHRMS (NBA/CsI) m/z 442.0642 (C$_{16}$H$_{23}$NO$_5$+Cs$^+$ requires 442.0631).

1-(tert-Butyloxycarbonyl)-4-(methoxymethoxy)-3
[[(methanesulfonyl)oxy]methyl]-2,3-dihydroindole
(18)

A solution of 17 (80 mg, 0.26 mmol) in 5 mL anhydrous CH$_2$Cl$_2$ was cooled to 0° C. and treated with Et$_3$N (79 µL, 0.57 mmol). After 10 min, MsCl (40 µL, 0.52 mmol) was added and the reaction mixture was subsequently warmed to 25° C. and stirred for 3 h. The reaction solution was concentrated under reduced pressure. Flash chromatography (SiO$_2$, 2.5×10 cm, 30% EtOAc/hexane) yielded pure 18 (94 mg, 94%) as a colorless oil: $^1$H NMR (CDCl$_3$, 250 MHz) δ7.49 (m, 1H), 7.15 (m, 1H), 6.68 (d, J=9.0 Hz, 1H), 5.19 (d, J=8.8 Hz, 1H), 5.17 (d, J=8.8 Hz, 1H), 4.58 (dd, J=3.6, 9.7 Hz, 1H), 4.21 (app t, J=8.9 Hz, 1H), 4.00 (m, 2H), 3.79 (m, 1H), 3.46 (s, 3H), 2,71 (s, 3H), 1.54 (s, 9H); $^{13}$C NMR (CDCl$_3$, 100 MHz) δ153.9, 152.1, 130.5, 110.2, 108.8, 107.7, 103.9, 94.4, 81.0, 69.9, 56.2, 51.1, 37.9, 37.2, 28.2; IR (film) v$_{max}$ 2976, 1703, 1610, 1479, 1463, 1391, 1355, 1254, 1175, 1154, 1061, 952 cm$^{-1}$; FABHRMS (NBA/CsI) m/z 520.0388 (C$_{17}$H$_{25}$NO$_7$S+Cs$^+$ requires 520.0406).

DNA Alkylation Studies: Selectivity and Efficiency: Eppendorf tubes containing singly $^{32}$P 5'-end-labeled double-stranded DNA (9 µL) (Boger, D. L., et al., *Tetrahedron* 1991, 47, 2661.) in TE buffer (10 mM Tris, 1 mM EDTA, pH 7.5) were treated with the agents in DMSO (1 µL, at the specified concentrations). The solutions were mixed by vortexing and brief centrifugation and subsequently incubated at 4° C., 25° C. or 37° C. for 24–72 h. The covalently modified DNA was separated from unbound agent by EtOH precipitation of the DNA. The EtOH precipitations were carried out by adding t-RNA as a carrier (1 µL, 10 µg/µL), 3 M NaOAc (0.1 volume) and –20° C. EtOH (2.5 volumes). The solutions were mixed and chilled at –78° C. in a REVCO freezer for 1 h or longer. The DNA was reduced to a pellet by centrifugation at 4° C. for 15 min and washed with –20° C. 70% EtOH (in TE containing 0.2 M NaCl). The pellets were dried in a Savant Speed Vac concentrator and resuspended in TE buffer (10 µL). The solutions of alkylated DNA were warmed at 100° C. for 30 min to induce cleavage at the adenine N3 alkylation sites. After brief centrifugation, formamide dye solution (5 µL) was added. Prior to electrophoresis, the samples were denatured by warming at 100° C. for 5 min, placed in an ice bath, centrifuged briefly, and the supplement (2.8 µL) was loaded onto a gel. Sanger dideoxynucleotide sequencing reactions were run as standards adjacent to the agent treated DNA reaction samples. Polyacrylamide gel electrophoresis (PAGE) was run on a 8% sequencing gel under denaturing conditions (19:1 acrylamide: N,N-methylenebisacrylamide, 8 M urea) in TBE buffer (100 mM Tris, 100 mM boric acid, 0.2 mM Na$_2$EDTA). PAGE was pre-run for 30 min with formamide dye solution prior to loading the samples. Autoradiography of dried gels was carried out at –78° C. using Kodak O-Omat AR film and Picker Spectra™ intensifying screen.

What is claimed:

1. A DNA alkylating compound comprising a DNA alkylating subunit and a DNA binding subunit covalently linked said DNA binding subunit, said DNA alkylating compound being represented by the following structure:

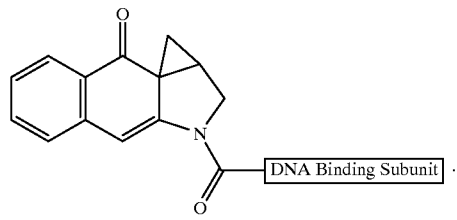

2. A DNA alkylating compound as described in claim 1 wherein said DNA binding subunit is a radical represented by the following structure:

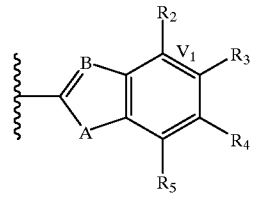

wherein:

A is selected from the group consisting of NH and O;

B is selected from the group consisting of C and N;

R$_2$ is selected from the group consisting of hydrogen, hydroxyl, O-alkyl (C1–C6), N-alkyl (C1–C6)$_3$ and a first N-substituted pyrrolidine ring;

R$_3$ is selected from the group consisting of hydrogen, hydroxyl, O-alkyl (C1–C6), N-alkyl (C1–C6)$_3$, the first N-substituted pyrrolidine ring;

R$_4$ is selected from the group consisting of hydrogen, hydroxyl, O-alkyl (C1–C6), and N-alkyl (C1–C6)$_3$;

R$_5$ is selected from the group consisting of hydrogen, hydroxyl, O-alkyl (C1–C6), and N-alkyl (C1–C6)$_3$; and V$_1$ represents a first vinylene group between R$_2$ and R$_3$;

with the following provisos:
if R$_2$ participates in the first N-substituted pyrrolidine ring, then R$_3$ also particlates in the first N-substituted pyrrolidine ring;
if R$_3$ participates in the first N-substituted pyrrolidine ring, then R$_2$ also particlates in the first N-substituted pyrrolidine ring;
if R$_2$ and R$_3$ participate in the first N-substituted pyrrolidine ring, then R$_4$ and R$_5$ are hydrogen;
if R$_2$ is hydrogen, then R$_4$ and R$_5$ are hydrogen and R$_3$ is N-alkyl (C1–C6)$_3$; and wherein the first N-substituted pyrrolidine ring is fused to the first vinylene group between R$_2$ and R$_3$ and is represented by the following structure:

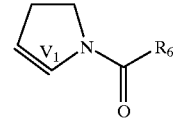

wherein:

V$_1$ represents the first vinylene group between R$_2$ and R$_3$;

R$_6$ is selected from the group consisting of —CH$_2$CH$_3$ (alkyl), —NHCH$_3$ (—N-alkyl), —OCH$_3$ (O-alkyl), —NH$_2$, —NHNH$_2$, —NHNHCO$_2$$^t$Bu, and a radical represented by the following structure:

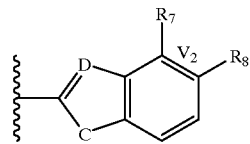

wherein:

C is selected from the group consisting of NH and O;

D is selected from the group consisting of C and N;

$R_7$ is selected from the group consisting of hydrogen, hydroxyl, O-alkyl (C1–C6), N-alkyl (C1–C6)$_3$, and a second N-substituted pyrrolidine ring;

$R_8$ is selected from the group consisting of hydrogen, hydroxyl, O-alkyl (C1–C6), N-alkyl (C1–C6)$_3$, the second N-substituted pyrrolidine ring;

$V_2$ represents the second vinylene group between $R_7$ and $R_8$;

with the following provisos:
   if $R_7$ participates in the N-substituted pyrrolidine ring, then $R_8$ also particlates in the N-substituted pyrrolidine ring;
   if $R_8$ participates in the N-substituted pyrrolidine ring only if $R_7$ also particlates in the N-substituted pyrrolidine ring; and wherein the second N-substituted pyrrolidine ring is fused to the second vinylene group between $R_7$ and $R_8$ and is represented by the following structure:

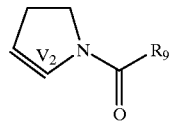

wherein:

$V_2$ represents the second vinylene group between $R_7$ and $R_8$;

$R_9$ is selected from the group consisting of —CH$_2$CH$_3$ (alkyl), —NHCH$_3$ (—N-alkyl), —OCH$_3$ (O-alkyl), —NH$_2$, —NHNH$_2$, and —NHNHCO$_2$$^t$Bu.

3. A DNA alkylating compound as described in claim 2 represented by the following structure:

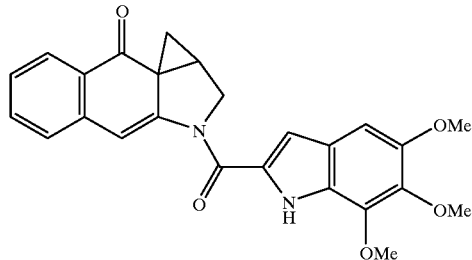

4. A DNA alkylating compound as described in claim 2 represented by the following structure:

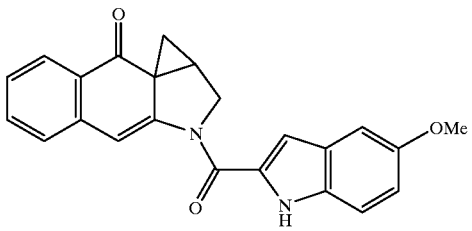

5. A DNA alkylating compound as described in claim 2 represented by the following structure:

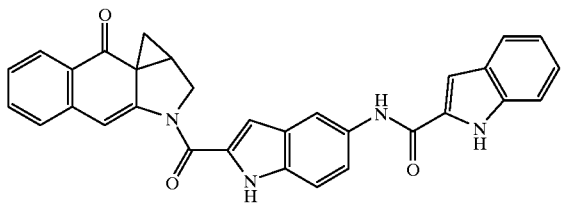

6. A DNA alkylating compound as described in claim 2 represented by the following structure:

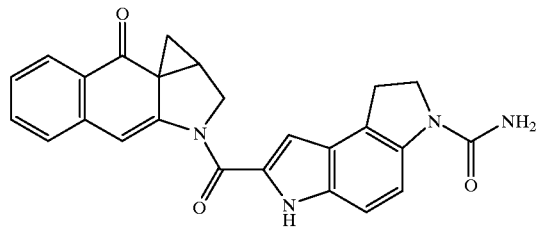

7. A DNA alkylating compound as described in claim 2 represented by the following structure:

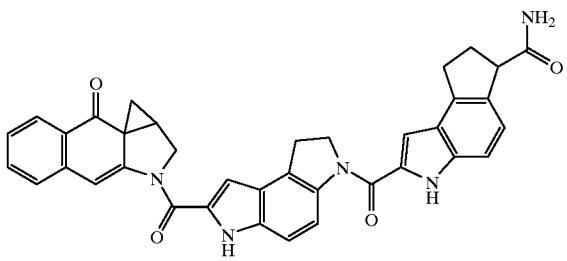

8. A DNA alkylating compound represented by the following structure:

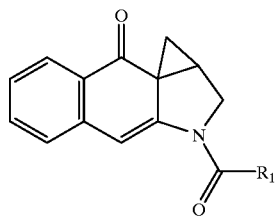

wherein $R_1$ is selected from the group consisting of —C1–C6 alkyl, —NHCH$_3$ (—N-alkyl), —OCH$_3$ (O-alkyl), —NH₂, —NHNH₂, —NHNHCO₂ᵗBu, and a radical represented by the following structure:

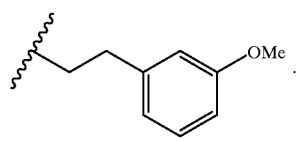

9. A DNA alkylating compound as described in claim 8 represented by the following structure:

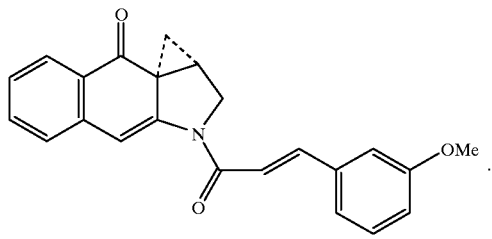

10. A chemical intermediate represented by the following structure:

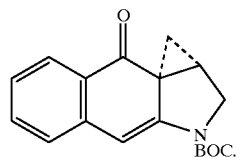

11. A chemical intermediate represented by the following structure:

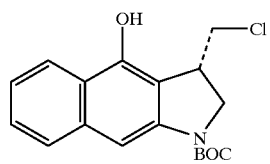

12. A DNA alkylating compound comprising a DNA alkylating subunit and a DNA binding subunit covalently linked said DNA alkylating subunit, said DNA alkylating compound being represented by the following structure:

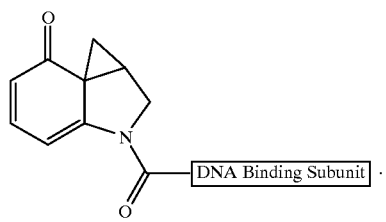

13. A DNA alkylating compound as described in claim 12 wherein said DNA binding subunit is a radical represented by the following structure:

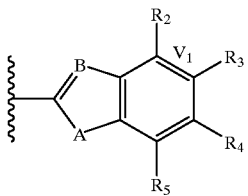

wherein:
A is selected from the group consisting of NH and O;
B is selected from the group consisting of C and N;
$R_2$ is selected from the group consisting of hydrogen, hydroxyl, O-alkyl (C1–C6), N-alkyl (C1–C6)₃ and a first N-substituted pyrrolidine ring;
$R_3$ is selected from the group consisting of hydrogen, hydroxyl, O-alkyl (C1–C6), N-alkyl (C1–C6)₃, the first N-substituted pyrrolidine ring;
$R_4$ is selected from the group consisting of hydrogen, hydroxyl, O-alkyl (C1–C6), and N-alkyl (C1–C6)₃;
$R_5$ is selected from the group consisting of hydrogen, hydroxyl, O-alkyl (C1–C6), and N-alkyl (C1–C6)₃; and
$V_1$ represents a first vinylene group between $R_2$ and $R_3$;
with the following provisos:
if $R_2$ participates in the first N-substituted pyrrolidine ring, then $R_3$ also particlates in the first N-substituted pyrrolidine ring;
if $R_3$ participates in the first N-substituted pyrrolidine ring, then $R_2$ also particlates in the first N-substituted pyrrolidine ring;
if $R_2$ and $R_3$ participate in the first N-substituted pyrrolidine ring, then $R_4$ and $R_5$ are hydrogen;
if $R_2$ is hydrogen, then $R_4$ and $R_5$ are hydrogen and $R_3$ is N-alkyl (C1–C6)₃; and
wherein the first N-substituted pyrrolidine ring is fused to the first vinylene group between $R_2$ and $R_3$ and is represented by the following structure:

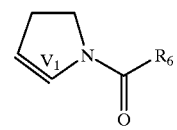

wherein:
$V_1$ represents the first vinylene group between $R_2$ and $R_3$;
$R_6$ is selected from the group consisting of —CH₂CH₃ (alkyl), —NHCH₃ (—N-alkyl), —OCH₃ (O-alkyl), —NH₂, —NHNH₂, —NHNHCO₂ᵗBu, and a radical represented by the following structure:

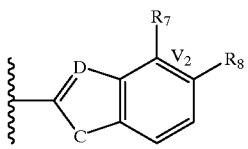

wherein:
C is selected from the group consisting of NH and O;
D is selected from the group consisting of C and N;
$R_7$ is selected from the group consisting of hydrogen, hydroxyl, O-alkyl (C1–C6), N-alkyl (C1–C6)₃, and a second N-substituted pyrrolidine ring;

R₈ is selected from the group consisting of hydrogen, hydroxyl, O-alkyl (C1–C6), N-alkyl (C1–C6)₃, the second N-substituted pyrrolidine ring;

V₂ represents the second vinylene group between R₇ and R₈; with the following provisos:
  if R₇ participates in the N-substituted pyrrolidine ring, then R₈ also particlates in the N-substituted pyrrolidine ring;
  if R₈ participates in the N-substituted pyrrolidine ring only if R₇ also particlates in the N-substituted pyrrolidine ring; and
  wherein the second N-substituted pyrrolidine ring is fused to the second vinylene group between R₇ and R₈ and is represented by the following structure:

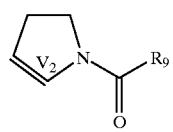

wherein:
  V₂ represents the second vinylene group between R₇ and R₈;
  R₉ is selected from the group consisting of —CH₂CH₃ (alkyl), —NHCH₃ (—N-alkyl), —OCH₃ (O-alkyl), —NH₂, —NHNH₂, and —NHNHCO₂ᵗBu.

14. A DNA alkylating compound as described in claim 13 represented by the following structure:

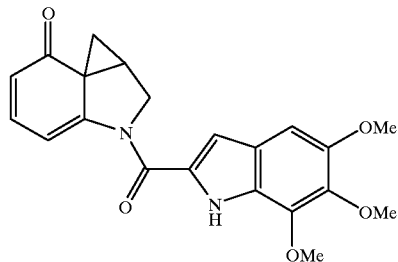

15. A DNA alkylating compound as described in claim 13 represented by the following structure:

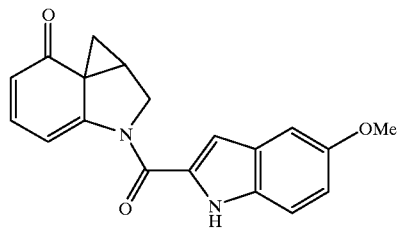

16. A DNA alkylating compound as described in claim 13 represented by the following structure:

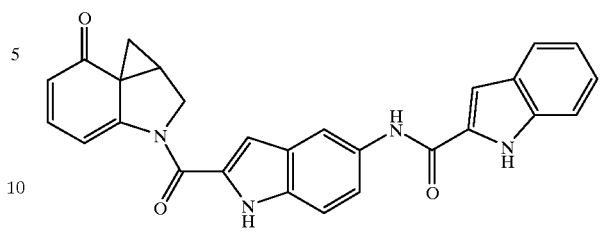

17. A DNA alkylating compound as described in claim 13 represented by the following structure:

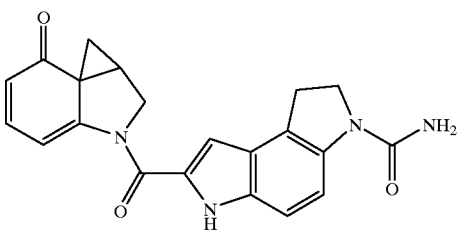

18. A DNA alkylating compound as described in claim 13 represented by the following structure:

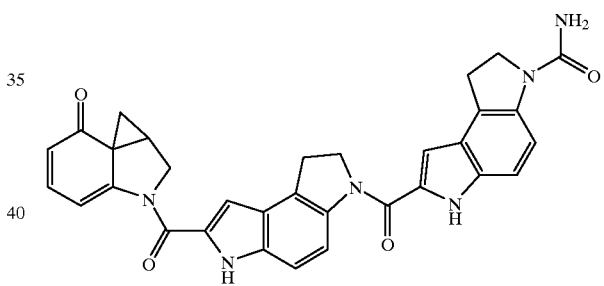

19. A DNA alkylating compound represented by the following structure:

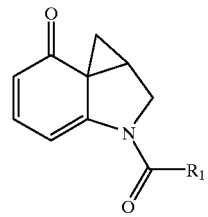

wherein R₁ is selected from the group consisting of —C1–C6 alkyl, —NHCH₃ (—N-alkyl), —OCH₃ (O-alkyl), —NH₂, —NHNH₂, —NHNHCO₂ᵗBu, and a radical represented by the following structure:

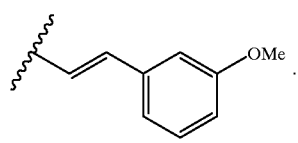
20. A DNA alkylating compound as described in claim 19 represented by the following structure:
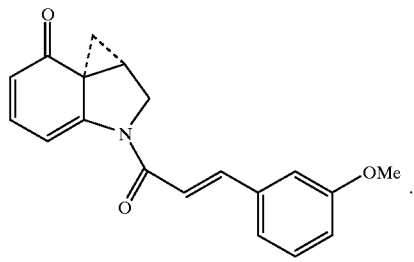
21. A chemical intermediate represented by the following structure:
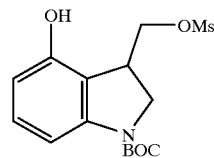
22. A chemical intermediate represented by the following structure:
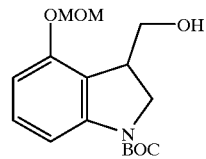
* * * * *